(12) United States Patent
Wang et al.

(10) Patent No.: US 7,459,303 B2
(45) Date of Patent: Dec. 2, 2008

(54) IMPEDANCE BASED APPARATUSES AND METHODS FOR ANALYZING CELLS AND PARTICLES

(75) Inventors: Xiaobo Wang, San Diego, CA (US); Xiao Xu, San Diego, CA (US)

(73) Assignee: ACEA Biosciences, San Diego, CA (US)

( * ) Notice: Subject to any disclaimer, the term of this patent is extended or adjusted under 35 U.S.C. 154(b) by 689 days.

(21) Appl. No.: 10/705,615

(22) Filed: Nov. 10, 2003

(65) Prior Publication Data
US 2004/0152067 A1 Aug. 5, 2004

Related U.S. Application Data

(63) Continuation of application No. PCT/US03/22537, filed on Jul. 18, 2003.

(60) Provisional application No. 60/469,572, filed on May 9, 2003, provisional application No. 60/435,400, filed on Dec. 20, 2002, provisional application No. 60/397,749, filed on Jul. 20, 2002.

(51) Int. Cl.
*C12M 1/34* (2006.01)
(52) U.S. Cl. ............... 435/287.1; 435/32; 435/401; 435/288.5; 435/297.5
(58) Field of Classification Search ............... 435/288.4, 435/297.5, 297.1
See application file for complete search history.

(56) References Cited

U.S. PATENT DOCUMENTS

| | | |
|---|---|---|
| 2,656,508 A | 10/1953 | Coulter |
| 3,259,842 A | 7/1966 | Coulter et al. |
| 3,743,581 A | 7/1973 | Cady et al. |
| 3,890,201 A | 6/1975 | Cady |
| 4,072,578 A | 2/1978 | Cady et al. |
| 4,225,410 A | 9/1980 | Pace |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |

(Continued)

FOREIGN PATENT DOCUMENTS

EP 1 138 758 A1 4/2001

(Continued)

OTHER PUBLICATIONS

Bieberich and Guiseppi-Elie, Biosensors and Bioelectronics, 19:923-931 (2004).

(Continued)

*Primary Examiner*—William H Beisner
(74) *Attorney, Agent, or Firm*—David R. Preston & Associates, APC

(57) ABSTRACT

A device for monitoring the migration or invasion of a biological particle such as a cell is disclosed. The device includes an upper chamber adapted to receive and retain a cell sample, a lower chamber having at least two electrodes, and a biocompatible porous membrane having a porosity sufficient to allow cells to migrate therethrough. The membrane is disposed in the device so as to separate the upper and lower chambers from one another. Migration of cells through the porous membrane permits contact between the migrating cells and one or more electrodes of the lower chamber. The contact provides a detectable change in impedance between or among the electrodes.

48 Claims, 31 Drawing Sheets

U.S. PATENT DOCUMENTS

| | | | |
|---|---|---|---|
| 5,187,096 | A | 2/1993 | Giaever et al. |
| 5,218,312 | A | 6/1993 | Moro |
| 5,247,827 | A * | 9/1993 | Shah .......................... 73/28.01 |
| 5,278,048 | A | 1/1994 | Parce et al. |
| 5,284,753 | A | 2/1994 | Goodwin |
| 5,514,555 | A * | 5/1996 | Springer et al. ............ 435/7.24 |
| 5,563,067 | A | 10/1996 | Sugihara et al. |
| 5,601,997 | A * | 2/1997 | Tchao .......................... 435/29 |
| 5,622,872 | A | 4/1997 | Ribi |
| 5,626,734 | A | 5/1997 | Docoslis et al. |
| 5,643,742 | A | 7/1997 | Malin et al. |
| 5,766,934 | A | 6/1998 | Guiseppi-Elie |
| 5,801,055 | A | 9/1998 | Henderson |
| 5,810,725 | A | 9/1998 | Sugihara et al. |
| 5,851,489 | A | 12/1998 | Wolf et al. |
| 5,981,268 | A | 11/1999 | Kovacs et al. |
| 6,051,422 | A | 4/2000 | Kovacs et al. |
| 6,132,683 | A | 10/2000 | Sugihara et al. |
| 6,169,394 | B1 | 1/2001 | Frazier et al. |
| 6,232,062 | B1 | 5/2001 | Kayyem et al. |
| 6,235,520 | B1 | 5/2001 | Malin et al. |
| 6,280,586 | B1 | 8/2001 | Wolf et al. |
| 6,288,527 | B1 | 9/2001 | Sugihara et al. |
| 6,368,795 | B1 | 4/2002 | Hefti |
| 6,368,851 | B1 | 4/2002 | Baumann et al. |
| 6,376,233 | B1 | 4/2002 | Wolf et al. |
| 6,440,662 | B1 | 8/2002 | Gerwen et al. |
| 6,448,030 | B1 | 9/2002 | Rust et al. |
| 6,448,794 | B1 | 9/2002 | Cheng et al. |
| 6,461,808 | B1 | 10/2002 | Bodner et al. |
| 6,472,144 | B2 | 10/2002 | Malin et al. |
| 6,485,905 | B2 | 11/2002 | Hefti |
| RE37,977 | E | 2/2003 | Sugihara et al. |
| 6,566,079 | B2 | 5/2003 | Hefti |
| 6,573,063 | B2 | 6/2003 | Hochman |
| 6,596,499 | B2 | 7/2003 | Jalink |
| 6,626,902 | B1 | 9/2003 | Kucharczyk et al. |
| 6,627,461 | B2 | 9/2003 | Chapman et al. |
| 6,630,359 | B1 | 10/2003 | Caillat |
| 6,637,257 | B2 * | 10/2003 | Sparks .......................... 73/38 |
| RE38,323 | E | 11/2003 | Sugihara et al. |
| 6,686,193 | B2 | 2/2004 | Maher et al. |
| 6,716,620 | B2 | 4/2004 | Bashir et al. |
| 6,723,523 | B2 * | 4/2004 | Lynes et al. ................ 435/7.21 |
| 7,192,752 | B2 | 3/2007 | Xu et al. |
| 2002/0032531 | A1 | 3/2002 | Mansky et al. |
| 2002/0076690 | A1 | 6/2002 | Miles et al. |
| 2002/0086280 | A1 | 7/2002 | Lynes et al. |
| 2002/0090649 | A1 | 7/2002 | Chan et al. |
| 2002/0110847 | A1 | 8/2002 | Baumann et al. |
| 2002/0150886 | A1 | 10/2002 | Miles et al. |
| 2003/0032000 | A1 | 2/2003 | Liu et al. |
| 2003/0072549 | A1 | 4/2003 | Facer et al. |
| 2003/0116447 | A1 | 6/2003 | Surridge et al. |
| 2003/0143625 | A1 | 7/2003 | Martin et al. |
| 2003/0157587 | A1 | 8/2003 | Gomez et al. |
| 2003/0166015 | A1 | 9/2003 | Zarowitz et al. |
| 2004/0091397 | A1 * | 5/2004 | Picard .......................... 422/99 |
| 2004/0146849 | A1 | 7/2004 | Huang et al. |
| 2005/0014130 | A1 | 1/2005 | Liu et al. |

FOREIGN PATENT DOCUMENTS

| | | |
|---|---|---|
| EP | 1195432 B1 | 9/2004 |
| WO | 96/01836 | 1/1996 |
| WO | 99/66329 | 12/1999 |
| WO | 00/71669 | 11/2000 |
| WO | 01/25769 | 4/2001 |
| WO | 01/038873 | 5/2001 |
| WO | 02/04943 | 1/2002 |
| WO | 02/42766 | 5/2002 |
| WO | 03/016887 | 2/2003 |
| WO | 05/005979 | 1/2005 |

OTHER PUBLICATIONS

Burnett et al., J. Biomo. Screening, 8 (6) :660-667 (2003).
Ciambrone et al., J. Biomo. Screening, 9 (6) :467-480 (2004).
Ehret et al., Med. Biol. Eng. Comput. 36 :365-370 (1998).
Ehret et al., Biosensors and Bioelectronics, 12 (1) :29-41 (1996).
Gutmann et al., Pharmaceutical Research, 16(3) :402-407 (1999).
Hug, Assay and Drug Dev. Tech., 1 (3) :479-488 (2003).
Lin and Huang, J. Micromech. Microeng., 11:542-547 (2001).
Lin et al., Min. For Chem., Bio., & Bioeng., 4:104-108 (2004).
Wegener et al., Eur. J. Physiol., 437:925-934 (1999).
Wolf et al., Biosensors and Bioelectronics, 13:501-509 (1998).
Xiao and Luong, Biotechnol. Prog., 19:1000-1005 (2003).
Xiao et al., Anal. Chem., 74:5748-5753 (2002).
Yamauchi et al., Nuc. Acids Res., 32(22):1-8 (2004).
Loffert et al., QIAGENNews, 4:15-18 (1997).
PCT International Preliminary Report on Patentability for PCT/US2005/034561, Sep. 2006.
PCT International Preliminary Report on Patentability for PCT/US2005/027943, Mar. 2007.
PCT International Search Report and Written Opinion for PCT/US2005/027943, Mar. 2007.
EP supplementary Search Report for EP 03748948.1 (from PCT/US2003/22557), Mar. 2007.
Mohr et al., Performance of a thin film microelectrode array for monitoring electrogenic cells in vitro, Sensors and Actuators B34:265-269. 1996.
Cady et al., Electrical Impedance Measurements: Rapid Method for Detecting and Monitoring Microorganisms 1978.
Wegner et al. Electric Cell-Substrate Impedance Sensing (ECIS) as a Noninvasive Means to Monitor the Kinetics of Cell Spreading to Artificial Surfaces. Experimental Cell Research 259, 158-166 (2000).
Aravanis et al. A genetically engineered cell-based bisensor for functional classification of agents. Biosensors & Bioelectronics 16:571-577 (2001).
Baumann et al. Microelectronics sensor system for microphysiological application on living cells. Sensors & Accuators B55:77-89 (1999).
Becker et al, Separation of human breast cancer cells from blood by differential dielectric affinity. Cell Biology. 92:960-964 (1995).
Berens et al, The role of extracellular matrix in human astrocytoma migration and proliferation studied in a microliter scale assay. Clin. Exp. Metastasis 12:405-415 (1994).
Bergveld, A critical evaluation of direct electrical protein detection methods, Biosensors& Bioelectronics. 6:55-72 (1991).
Burns et al, Neutrophil Transendothelial Migration Is Independent of Tight Junctions and Occurs Preferentially at Tricellular Corners. Journal of Immunology 2893-2903 (1997).
Duan et al, Separation-Free Sandwich Enzyme Immnoassays Using Microporous Gold Electrodes and Self-Assembled Monolayer/Immobilized Capture Antibodies, Anal. Chem. 66:1369-1377 (1994).
Connolly et al., An extracellular microelectrode array for monitoring electrogenic cells in culture Biosensors & Bioelectronics 5: 223-234 (1990).
Ehret et al, Monitoring of cellular behaviour by impedance measurements on interdigitated electrode structures. Biosensors and Bioelectronics 12(1):29-41 (1997).
Ehret et al, On-line control of cellular adhesion with impedance measurements using interdigitated electrode structures, Meidcal & Biolgical Engineering and Computing 36:365-370 (1998).
Falk et al, A 48-well Micro Chemotaxis Assembly for Rapid and Accurate Measurement of Leukocyte Migration. J Immunol. Meth. 33:239-247 (1980).
Fuhr et al, Positioning and Manipulation of Cells and Microparticles Using Miniaturized Electric Field Traps and Travelling Waves. Sensors and Materials 7(2):131-146 (1995).
Gaiever et al, Monitoring fibroblast behavior in tissue culture with an applied electric field. Proc. Natl. Acad. Sci 81:3761-3764 (1984).

Giaever et al., Micromotion of mammalian cells measured electrically. Proc. Natl. Acad. USA 88:7896-7900 (1991).

Hadjout et al., Automated Real-Time Measurement of Chemotactic Cell Motility BioTechniques 31:1130-1138 (2001).

Henning et al, Approach to a multiparametric sensor-chip-based tumor chemosensitivity assay, Anti-Cancer Drugs 12:21-32 (2001).

Hidalgo et al, Characterization of the Human Colon Carcinoma Cell Line (Caco-2) as a Model System for Intestinal Epithelial Permeability. Gastroenterology 96:736-749 (1989).

Huang et al., Dielectrophoretic Cell Separation and Gene Expression Profiling on Microelectronic Chip Arrays. Anal. Chem. 74:3362-3371 (2002).

Keese et al, Real-time inpedance assay to follow the invasive activites of metastatic cells in culture. Biotechniques 33:842-850 (2002).

Kleinmann et al, Basement Membrane Complexes with Biological Activity. Biochemistry. 26:312-318 (1986).

Kowolenko et al., Measurement of macrophage adherence and spreading with weak electric fields. Journal of Immunological Methods 127:71-77 (1990).

Larsen et al, Somatic Cell Counting with Silicon Apertures. Micro Total Analysis Systems 103-106 (2000).

Lo et al, Monitoring motion of confluent cells in tissue culture, Experimental Cell Research 204:102-109 (1993).

Lo et al., pH Changes in pulsed $CO_2$ incubators cause periodic changes in cell morphology Experimental Cell Research 213:391-397 (1994).

Lo et al., Impedance Analysis of MDCK cells measured by electric cell-substrate impedance sensing Biophysical Journal 69:2800-2807 (1995).

Luong, et al., Monitoring Motility, Spreading, and Mortality of Adherent Insect Cells Using an Impedance Sensor. Analytical Chemistry 73:1844-1848 (2001).

Mitra et al, Electric measurements can be used to monitor the attachment and spreading of cells in tissue culture. Biotechniques 11(4):504-510 (1991).

Miyata et al, New Wound-Healing Model Using Cultured Corneal Endothelial Cells. Jpn. J. Ophthalmol. 34:257-266 (1990).

Neher, Molecular biology meets microelectronics Nature Biotechnology 19:114 (2001).

Nerurkar et al, The Use of Surfactants to Enhance the Permeability of Peptides Through Caco-2 Cells by Inhibition of an Apically Polarized Efflux System. Pharmaceutical Research 13(4):528-534 (1996).

Ong et al, Remote Query Resonant-Circuit Sensors For Monitoring of Bacterial Growth: Application to Food Quality Control. Sensors 2:219-222 (2002).

Pancrazio et al, Portable cell-based biosensor system for toxin detection. Sensors and Actuators B 53:179-185 (1998).

Patolsky et al, Detection of single-base DNA mutations by enzyme-amplified electronic transduction. Nature Biotechnology 19:253-257 (2001).

Pethig et al, Positive and negative dielectrophoretic collection of colloidal particles using interdigitated castellated microelectrodes. Appl. Phys. 24:881-888 (1992).

Richards et al, A Modified Microchamber Method For Chemotaxis and Chemokinesis. Immunological Communications 13(1):49-62 (1984).

Rishpon et al, An amperometric enzyme-channeling immunosensor, Biosensors & Bioelectronics, 12(3):195-204 (1997).

Simpson et al., Whole-cell biocomputing Trends in Biotechnology 19:317-323 (2001).

Sohn et al, Capacitance cytometry: Measuring biological cells one by one. Proc. Nat. Acad. Sci. 97(20)10687-10690 (2000).

Stenger et al., Detection of physiologically active compounds using cell-based biosensors. Trends in Biotechnology 19:304-309 (2001).

Svetlicic et al., Charge displacement by adhesion and spreading of a cell Bioelectrochemistry 53:79-86 (2000).

Tiruppathi et al, Electrical method for detection of endothelial cell shape change in time: assessment of endothelial barrier function. Proc Natl Acad Sci USA 89:7919-7923 (1992).

Wang et al, A theoretical method of electrical field analysis for dielectrophoretic electrode arrays using Green's theorem. Appl. Phys. 1649-1660 (1996).

Wang et al, Selective dielectrophoretic confinement of bioparticles in potential energy wells. Appl. Phys. 26:1278-1285 (1993).

Wang et al, Cell Separation by Dielectrophoretic Field-flow-fractionation. Anal. Chem. 72:832-839 (2000).

Wang et al, Dielectrophoretic Manipulation of Cells with Spiral Electrodes. Biophysical Journal 72:1887-1899 (1997).

Wang et al, Separation of Polystyrene Microbeads Using Dielectrophoretic/Graviational Field-Flow-Fractionation. Biophysical Journal 74:2689-2701 (1998).

Wang et al., Electronic Manipulation of Cells on Microchip-Based Devices. In Biochip Technology (eds.) Harwood Academic Publishers, PA U.S.A. 135-159 (no date provided).

Warburg, Ueber die Polarisationscapacitat des Platins. Ann. Phy. 6:125-135 (1901).

Wegener et al, Electric cell-substrate impedance sensing system (ECIS) as a noninvasive means to monitor the kinetics of cell spreading to artificial surfaces, Experimental Cell Research, 259:158-166 (2000).

Wolf et al, Monitoring of cellular signalling and metabolism with modular sensor-technique: The PhysioControl0Microsystem (PCM). Biosensors & Bioelectronics 13:501-509 (1998).

Xiao et al, An in-depth Analysis of Electric Cell-Substrate Impedance Sensing To Study the Attachment and Spreading of Mammalian Cells, Anal. Chem 74:1333-1339 (2002).

Yang et al, Cell Separation on Microfabricated Electrodes Using Dielectrophoretic/Gravitational Field-Flow Fractionation. Anal. Chem. 71:911-918 (1999).

http://www.neuroprobe.com/protocol/pt_96a.html (no date provided).

http://www.bdbiosciences.com/discovery_labware/Products/inserts/BD_Falcon_HTS_fluoroblok_inserts/individual_fluoroblok_inserts/index.html (no date provided).

http://www.tecan.com/migration_introl.pdf (no date provided).

New Products page. Science 298:2409 (2002).

Abstract: Real-Time Impedance Assay to Follow the Invasive Activities of Metastatic Cells in Culture. Biotechniques 33: 842 (2002).

http://www.biophysics.com/pages/front.html (no date provided).

* cited by examiner

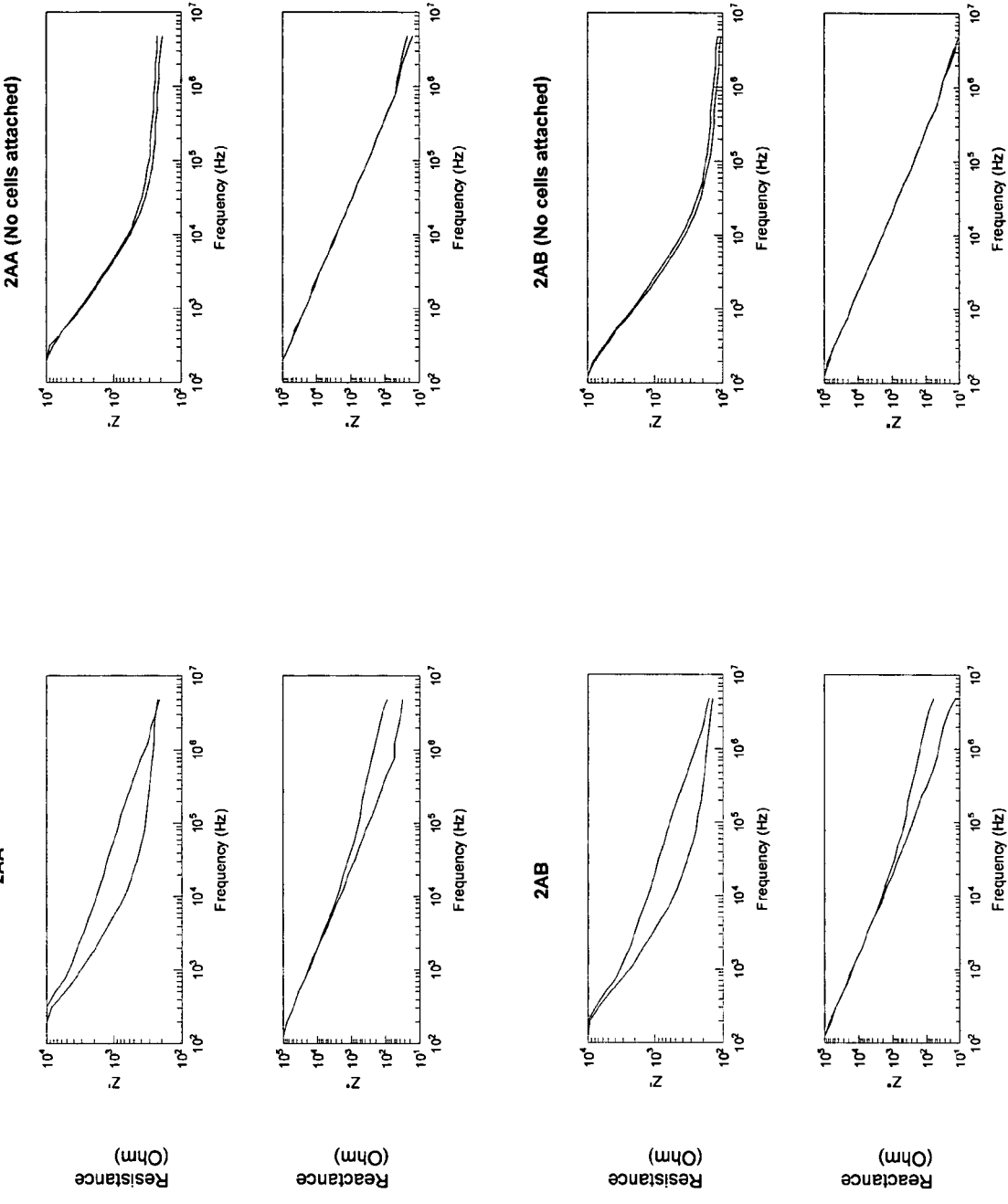
Figure 3A (1)

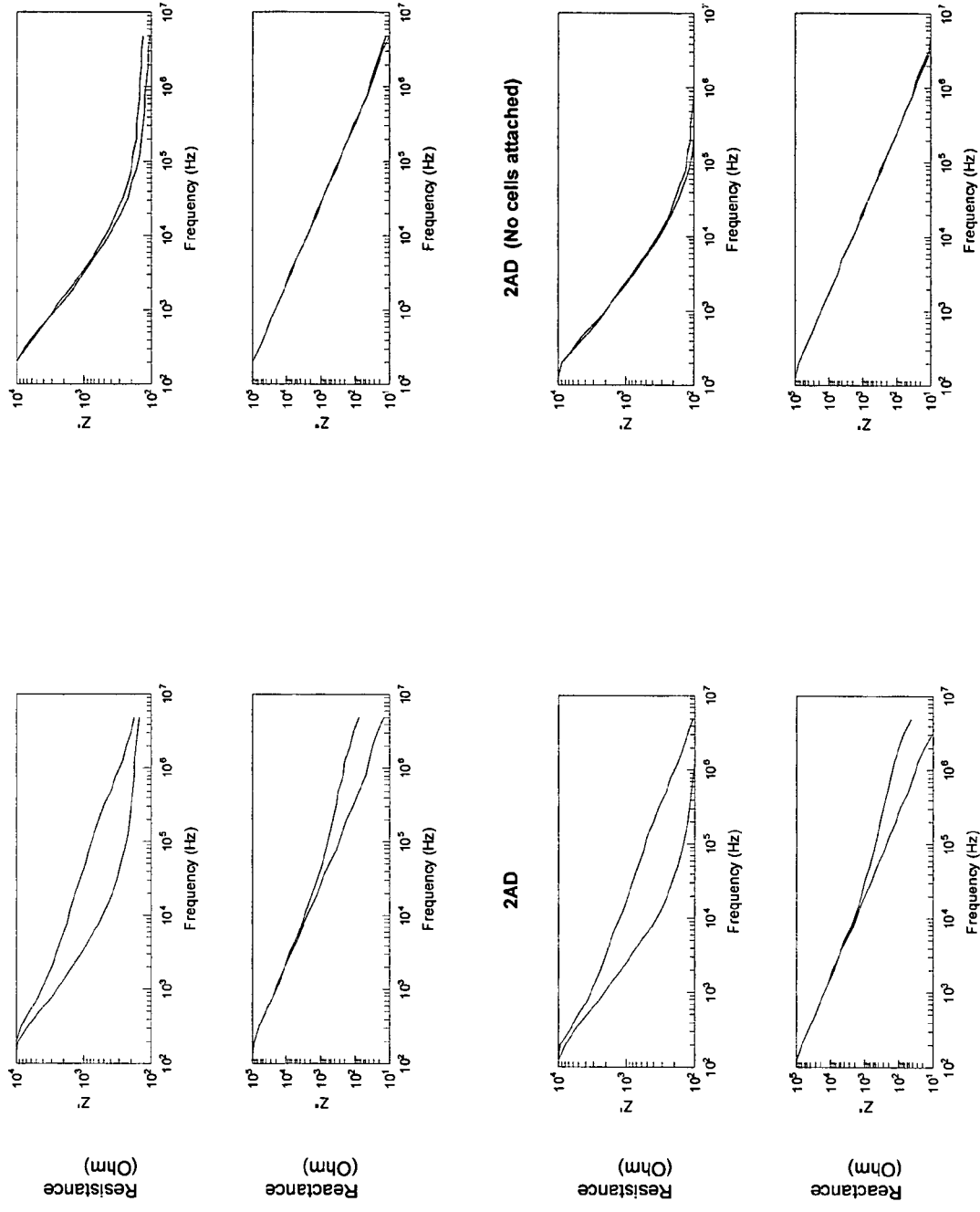
Figure 3A (2)

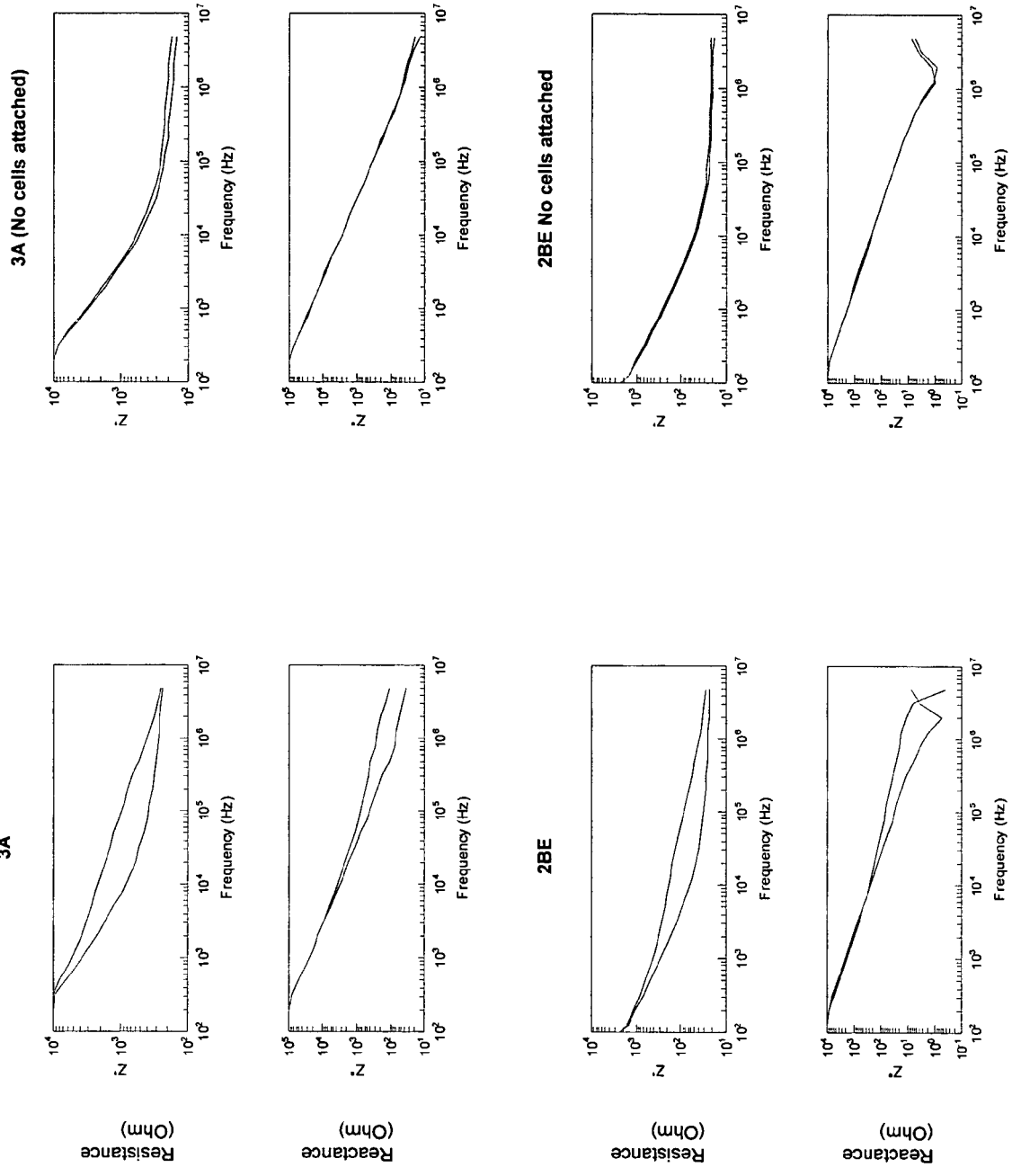
Figure 3A (3)

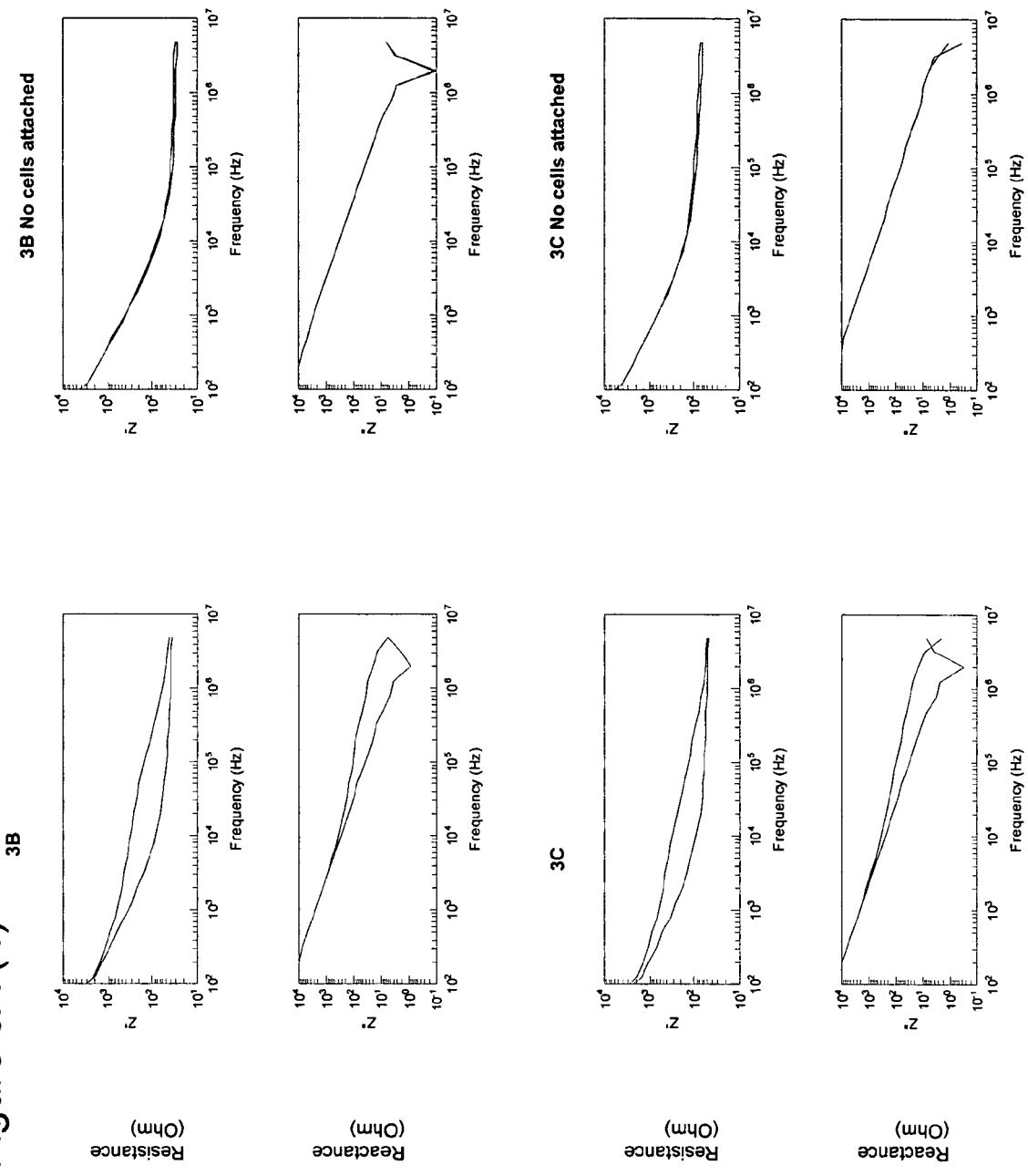
Figure 3A (4)

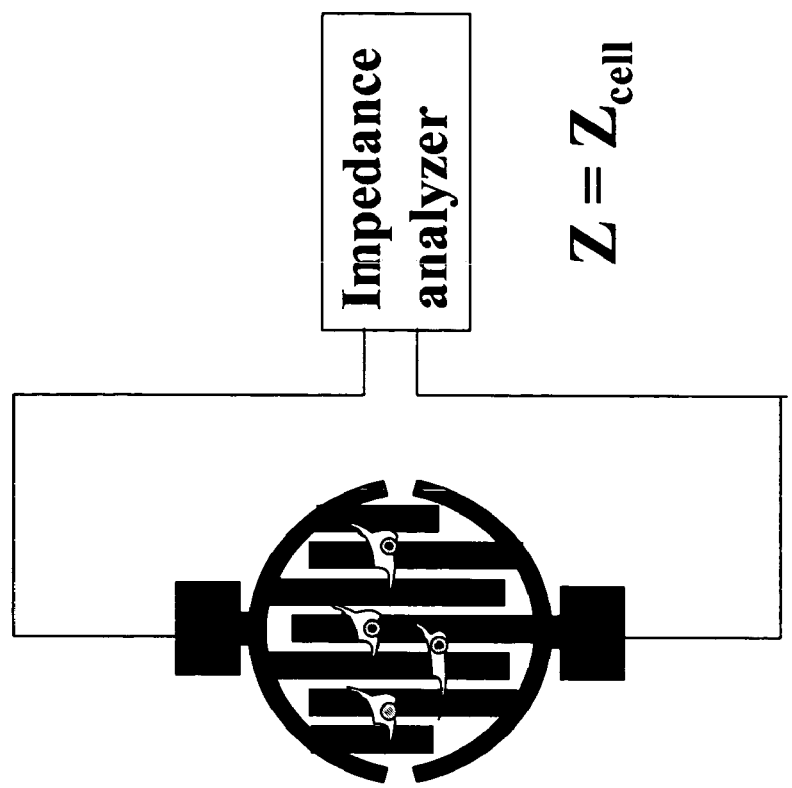
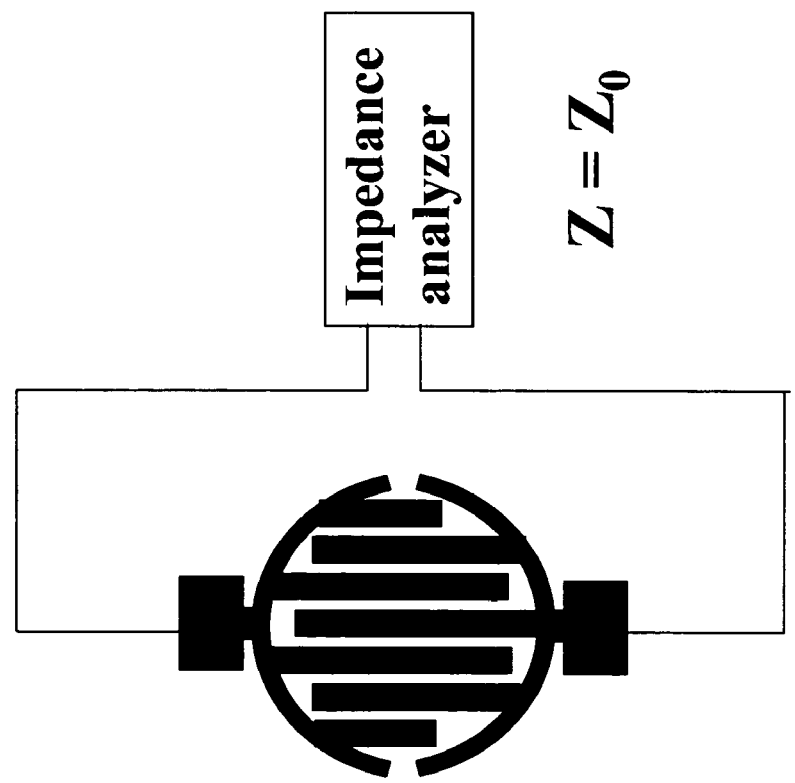
Figure 9

An electrode structure unit

↙ Concentric electrode structures

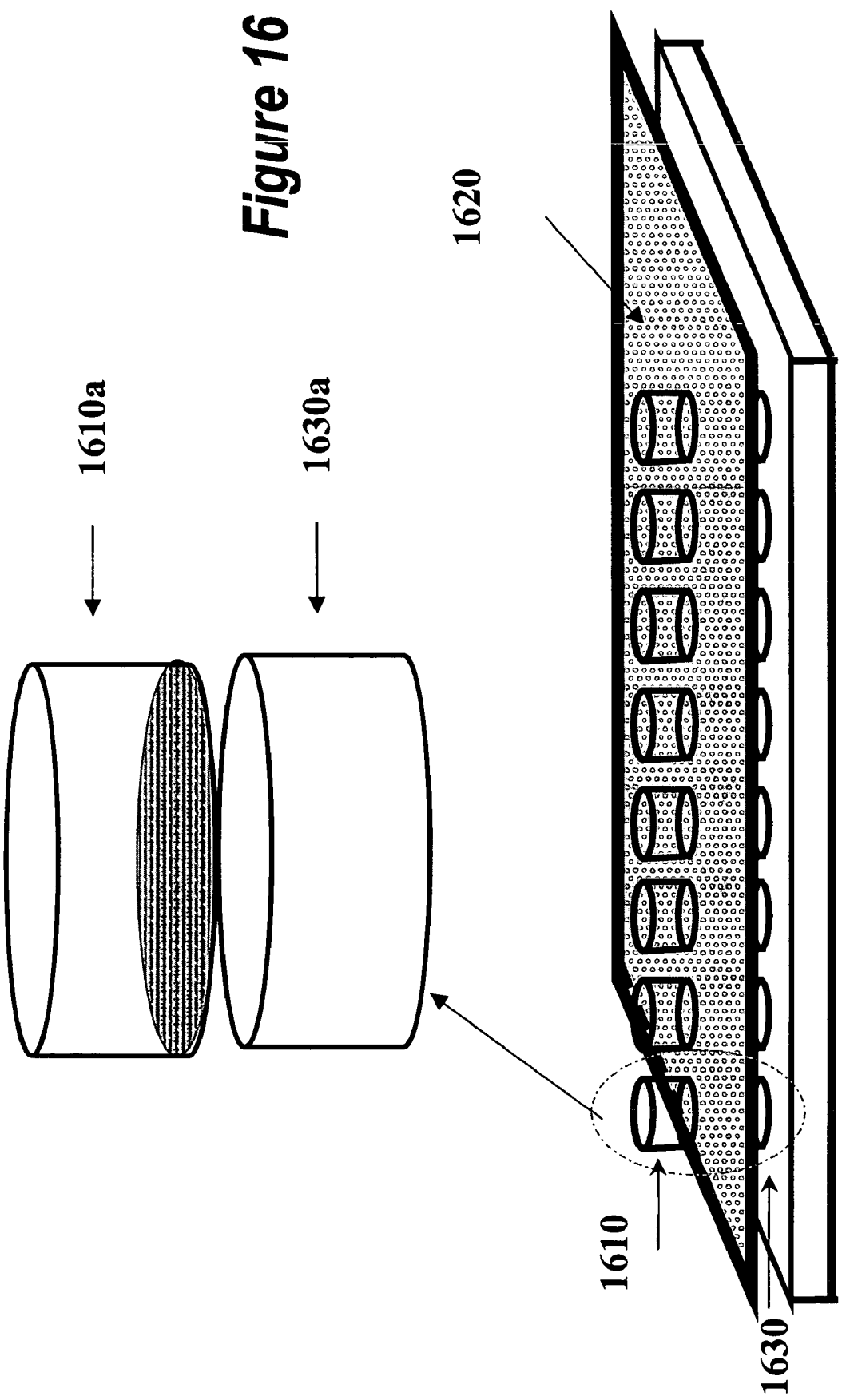

Figure 24.
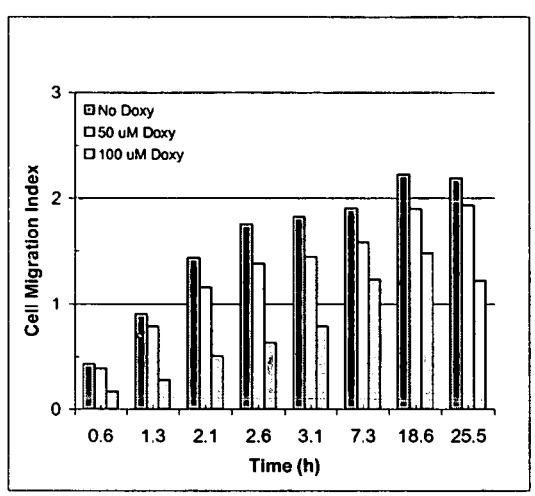
A.
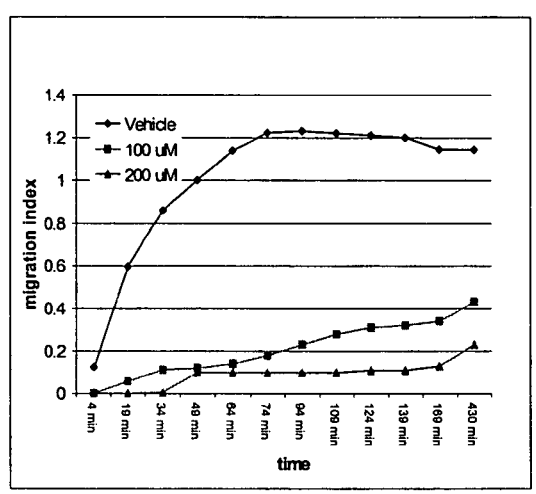
B.

IMPEDANCE BASED APPARATUSES AND METHODS FOR ANALYZING CELLS AND PARTICLES

This application is a continuation of PCT Application No. PCT/US03/22537, entitled "IMPEDANCE BASED APPARATUSES AND METHODS FOR ANALYZING CELLS AND PARTICLES", filed Jul. 18, 2003, which is incorporated by reference herein, and claims benefit of priority to U.S. provisional application No. 60/397,749, filed on Jul. 20, 2002; U.S. provisional application No. 60/435,400, filed on Dec. 20, 2002; and U.S. provisional application 60/469,572, filed on May 9, 2003, each of which is incorporated by reference herein. This application also incorporates by reference PCT Application No. PCT/US03/22557, entitled "IMPEDANCE BASED DEVICES AND METHODS FOR USE IN ASSAYS", filed Jul. 18, 2003.

BACKGROUND OF THE INVENTION

1. Technical Field

This invention relates generally to the field of analysis of cells and particles. In particular, the invention provides impedance based apparatuses, microplates and methods for analyzing cells and particles. The present apparatuses, microplates and methods can be used in monitoring cell or particle attachment, migration and invasion. The present apparatuses, microplates and methods can also be used in identifying modulators of cell or particle attachment, migration and growth.

2. Background Art

Growth and metastasis, or pathological cell migration, are the fundamental properties of malignant cells. Better understanding of molecular mechanisms underlying the pathological cell migration will improve cancer treatment and prevention.

To dissect the mechanisms, research models both in vivo and in vitro have been used. In vivo models can monitor an entire process of cancer metastasis in experimental animals, but are not suitable for large scale evaluation of the properties of malignant cells. In in vitro models, cancer cell growth and migration activities can be more quantitatively analyzed, including transmigration of cells through a monolayer or multi-layers of cultivated cells or explanted tissues, growth of cells through natural and artificial extracellular matrixes or similar cellular structures, and cell motility in response to chemotactic agents.

Currently, there are three common methods available for detecting cell growth and/or cell migration in vitro, which include:

(1) Chemoattractant-induced migration (i.e. chemotaxis, which is the directional response of biological cells or organisms to concentration gradients of chemicals) /invasion and trans-well migration assay (Falk, W., "A 48 Well Micro Chemotaxis Assembly for Rapid and Accurate Measurement of Leukocyte Migration." *Journal of Immunological Methods*, Vol: 33, pages, 239-247, 1980; Richards K. L. and J. McCullough, "A Modified Microchamber Method for Chemotaxis and Chemokinesis." *Immunological Communications*, Vol: 13, pages: 49-62, 1984): cells in inserts invade and migrate across a layer of an artificial pored membrane (polyvinylprrolidone-free polycarbonate membrane or polyethylene terephthalate membrane) into lower chambers containing a given chemoattractant. The migrated cells that are usually attached on the other side of the membrane are then labeled with either chemical dyes (Neuroprobe, Inc., See: Neuroprobe Inc. www. Neuroprobe.com/protocol/pt_96a.html) or fluorescent dyes, followed by cell counting under the microscope or by a spectrofluorometer (TECAN, Coster, BD Biosciences, (Ilsley, S. R. 1996. MATRIGEL® Basement Membrane Cell Invasion Chamber. Becton Dickinson Technical Bulletin #422; www.bdbiosciences.com/discovery_labware/technical_resources/tech-bulletins.html; BD BioCoat™ FluoroBlok™ Tumor Cell Invasion System, www.bdbiosciences.com/discovery_labware/Products/drug_discovery/insert_systems/fluoro-blok_invasion/; TECAN. www.tecan.com/migration_introl.pdf). For example, U.S. Pat. No. 5,284,753 discloses a multiple-site chemotactic test apparatus and method. In one approach, chemotactic factors and controls are placed at preselected areas on the top surface of a bottom plate, while a membrane filter containing pores of appropriate sizes and topped with cell suspensions is placed above the bottom plate so that the drops of chemotactic factors and controls contact the filter membrane directly below the locations of the cell suspensions. The cells that migrate through the membrane filter under influence of chemotactic factors and controls for a period of time are counted and determined.

(2) In situ cell diffusion and migration assay: Cells are spotted onto a chemoattractant-coated glass slide. As cells migrate and diffuse from the original spotted positions, the diameter of the spot where cells are present increases. The diameter of the spot is measured after incubation. The migration is determined based on the size of the cell spot over incubation time (Berens, M. E., et al, "The role of extracellular matrix in human astrocytoma migration and proliferation studied in a microliter scale assay", *Clinical and Experimental Metastasis*. Vol: 12, pages: 405-415,1994; Creative Scientific Methods. www.cre8ive-sci.com/process.html).

(3) In vitro wound healing assay: Scratching cells off a cell monolayer and measuring the healing process of scratch under a microscope (Miyata K., et al. "New wound-healing model using cultured corneal endothelial cells. 1. Quantitative study of healing process", *Jpn J Ophthalmol*. Vol: 34, pages: 257-266, 1990).

In situ cell diffusion and in vitro wound healing assays are easy to perform and costs for these assays are low. However, since neither of them is able to differentiate cell migration from cell proliferation, the results obtained from these two assay systems are not very reliable. The trans-well invasion and migration assay is the most commonly used and well-accepted in vitro method for analyzing cell invasion and migration. Such an assay uses an apparatus that contains an insert that forms an upper chamber, and a lower chamber. The two chambers are separated with an artificial extracelluar matrix (ECM)-coated pored membrane (or called membrane filter). Invasive cells placed in inserts or upper chambers can invade and migrate across an artificial ECM-coated microporous membrane to lower chambers. The invasion and migration activity is determined by counting the cells that have passed through the ECM-coated membrane into the lower chamber. This in vitro assay system appears to be able to mimic in vivo cell invasion and migration process, and to be suitable for large-scale assays for investigating responsive genes and intracellular signal transduction pathways. However, data collecting methods or technologies currently available for the in vitro system are either dye-based or radioactive isotope-based methods, and in the most cases, manual counting is required for data acquisition. Counting the cells that invade and migrate through the membrane to the lower chamber can be difficult and time consuming, which limits the assay accuracy and throughput significantly. Problems with sensitivity, reproducibility, and simplicity are often encountered when such data acquisition methods are used. A more efficient in vitro assay system is highly demanded nowadays, given that the identification of molecules and intracellular signal transduction pathways involving cell invasion and migration is increasing rapidly. To improve the assay accuracy and throughput, two new systems have been introduced by Amersham Pharmacia and Becton-Dickson (BD) Biosciences. The Amersham system uses a scintillation microplates (cytostar-T) (Graves, R., et al, "A novel assay for cell invasion using Cytostra-T scintillating microplates". Scientific poster,http://www1.amershambiosciences.com/aptrix/ upp00919.nsf/Content/DrugScr+Scientific+Posters) to measure the cell invasion and migration activity using [$^{14}$C] and [$^{35}$S] labeled cells. In the test wells, a lower layer of ECM gel is added to form a barrier preventing the labeled cells from reaching the scintillant containing baseplate. The labeled cells are then added in an upper layer of ECM gel, and the microplate is incubated overnight. Only cells invading the lower layer of ECM gel and gaining proximity to the scintillant generate a signal in the assay. The system allows for automation and real time monitoring of cells that have penetrated the ECM gel. However, the requirement for radioactive isotope labeling limits the use of the system. The system developed in BD Biosciences uses a light-tight FluoroBlok PET membrane that is specifically designed to block the transmission of light from 490 to 700 nm (BD BioCoat™ FluoroBlok™ Tumor Cell Invasion System: http://www.bd-biosciences.com/discovery_labware/Products/drug_discovery/insert_systems/fluoroblok_invasion/). The testing cells should be first stained with a fluorescent dye and than placed into the light-tight FluoroBlok PET membrane inserts. Invaded cells on the reverse sides of the inserts can be monitored by a fluorescent detector in real time without destroying the assays. Using this assay system the invasion assay productivity and throughput are significantly improved. However, since not every cell type can be homogenously labeled by the fluorescent dye and labeling has in some cases been found to alter cell invasion and migration, the application of the system has also been significantly limited.

Bioelectronics is a progressing interdisciplinary research field that involves the integration of biomaterials with electronic devices. There has been a growing interest in applying electronic methods for cell manipulation and cell analysis.

Cell-substrate impedance measurement is an electronic method for cell monitoring and sensing. Adherent cells are cultured on the surface of microelectrode structures located on a solid substrate. The presence and absence of cells on the electrode surface affect sensitively the electronic and ionic passage between cell culture media and the electrode structures (see, for example, Giaever I. and Keese C. R., "Monitoring fibroblast behavior in tissue culture with an applied electric field", Proc. Natl. Acad. Sci. (USA), 1984, vol. 81, pp 3761-3764). Thus, interrogating the electrode impedance provides important information about biological status of the cells present on the electrodes. U.S. Pat. No. 5,187,096 discloses a cell substrate electrical impedance sensor with multiple electrode arrays. Each electrode pair within the impedance sensor for measuring the cell-substrate impedance comprises one small electrode (a measuring electrode) and one large electrode (a reference electrode) on two different layers. The difference between the electrode sizes ensures that the measured impedance change relative to the impedance when no cells are present on the electrodes is directly correlated with the cell numbers and sizes, generally 20-50 cells, or even single cells attached to or grown on the measuring electrodes. Some applications of the cell sensor include the monitoring of conditions within bioreactors, within cell cultures, the testing of compounds for cytotoxicity, research of cell biology to detect cell motility, metabolic activity, cell attachment and spreading, etc. However, this impedance sensor with two layered structures is somewhat complicated with the measuring electrodes on one layer and the reference electrodes on another layer. The selected electrode area for the small electrodes limits the maximum of 50 cells being monitored.

U.S. Pat. No. 4,686,190 disclosed a device for in vitro study of cell migration across a monolayer of epithelia cells while simultaneously measuring the transepithelial electrical resistance of the epithelia monolayer.

WO 02/42766 A2 disclosed a device and method for investigating the effects of chemical and other factors on cell movement. In the dveice, cells migrate in an under-agarose environment and their position is monitored using a system capable of measuring changes in impedance and other electrical parameters of the system at a target electrode lithographed onto a substrate as the cells arrive at target.

Other data collecting methods or technologies currently used for in vitro cell migration assays are typically dye-based, and in the most cases manual counting is required. Problems with sensitivity, reproducibility, and simplicity are often encountered when the dye-based procedures are used.

To overcome the limitations of the existing art, the invention aims to expand the usage and application of electrical field and other electronic methods for measuring and analyzing cells, non-cell particles, and biological, physiological, and pathological conditions of cells or non-cell particles. To this end, the invention provides innovative cell migration assay devices using microelectronic technology.

SUMMARY OF THE INVENTION

In one aspect, the invention provides a device for monitoring the migration of a biological particle such as a cell. The device includes an upper chamber adapted to receive and retain a cell sample, a lower chamber having at least two electrodes, and a biocompatible porous membrane having a porosity sufficient to allow cells to migrate therethrough. The membrane is disposed in the device so as to separate the upper and lower chambers from one another. Migration of cells through the porous membrane permits contact between the migrating cells and one or more electrodes of the lower chamber. The contact provides a detectable change in impedance between or among the electrodes.

In a preferred embodiment, the device includes one or more capture reagents immobilized on the surfaces of the at least two electrodes. The capture reagents are capable of binding target cells and/or particles.

The electrodes may be disposed on the surface of the membrane in the lower chamber. In one embodiment, the lower chamber has a bottom surface area sufficient for attachment of a grouping of cells selected from the groupings consisting of 1-10, 10-100, 100-300, 300-700, 700-1,000, 1,000-3,000, 3,000-6,000, 6,000-10,000 and 1000-10000 cells. In another embodiment, the electrodes cover at least 5% of the surface area of the membrane in the lower chamber. In yet another embodiment, the surface area of the lower chamber is less than 1 µm².

In a preferred embodiment, the device includes an impedance analyzer in electrical communication with the electrodes.

The biocompatible porous membrane may include a nonconductive material. The nonconductive material may be glass, sapphire, silicon, silicon dioxide on silicon, or one or more polymers. In a preferred embodiment, the biocompatible porous membrane has a thickness between 2 microns and 500 microns.

The biocompatible porous membrane may also include a coating for promoting the attachment of one or more cells thereto.

In another embodiment, the device also includes electrically conductive traces extending from, and in electrical communication with, at least one of the electrode pairs, and connection means for establishing electrical communication between the electrically conductive traces and an impedence analyzer.

In another aspect, the invention includes a method for monitoring the migration of a cell. The method includes introducing the cells into the upper chamber of the above-described device and determining whether a change in impedance between or among the electrodes occurs. The change, if experienced, is indicative of the migration of, cells into or through, the biocompatible porous membrane.

The method may also include introducing a known or suspected modulator of cell migration to the lower chamber of the device.

In another embodiment, the method includes introducing a known or suspected modulator of cell migration to the upper chamber of the device.

The cells may be mammalian cells. In one embodiment, the mammalian cells are cells suspected of being malignant. In another embodiment, the mammalian cells are neuronal cells.

The cells may include one or more microorganisms.

BRIEF DESCRIPTION OF THE DRAWINGS

FIG. 9 illustrates a mechanism by which the electrode detects cells.

FIG. 16 is a schematic representation of an apparatus that comprises multiple top chambers (1610) and bottom chambers (1630). In this case, multiple top chambers (1610) are bonded to the membrane (1620) that have pores of appropriate sizes for cell migration or invasion. Each top chamber (e.g., 1610a) has a corresponding bottom chamber (e.g., 1630a). For each top chamber, there are electrode structures on the bottom surface of the membrane, facing the bottom chamber. In operation, the electrode structures on the membrane are connected to the impedance measuring instrument via different methods. For example, electrode structures are connected via conductive traces or paths on the membrane to connection pads at the edges of the membranes. Connection pads can be connected to impedance measuring instrument through different methods. In one approach, electrical wires that are in operative connection with impedance measuring instrument or circuits can be soldered or bonded via conductive bonding to these connection pads. There are also various embodiments for the top chambers. In one embodiment, multiple top chambers may be individually separated and become connected only after they are bonded to the same membrane (1620). In another embodiment, multiple top chambers are interconnected and are manufactured together (for example, multiple top chambers are plastics and manufactured by injection molding). The one piece of these top chambers is then bonded to the membrane.

FIG. 24 shows results of real time monitoring of the inhibitory effect of doxycycline on cancer cell invasion and migration using cell migration devices where the electrode structures were built onto the microporous membrane of the insert (similar to the structures shown in FIG. 16). (A) A time and dose-dependent inhibition of HT1080 cell invasion and migration by doxycycline. (B) Real-time monitoring of the dynamic inhibitory effect of doxycycline on HT1080 cell invasion and migration using a fully automated instrment with software controlled data acquisition for impedance measurement. As indicated in FIG. 24(B), the migration process was continuously monitored every 15 min.

FIG. 28(A) is a summary of the frequency spectra shown in FIGS. 25(C), 26(C) and 27(C). One method to calculate "cell number index" is based on such frequency spectra of resistance ratios by first determining the maximum value of the resistance ratio and then subtracting "one" from the maximum value. The "cell number indices" calculated this way for adding cells of different numbers of 7000, 3200 and 500 are 5.17, 1.82 and 0.17, respectively. Evidently, the larger the number of cells, the larger the cell number index.

FIG. 28(A) is a summary of the frequency spectra shown in FIGS. 25(D), 26(1)) and 27(D).

MODES OF CARRYING OUT THE INVENTION

Figure 1:
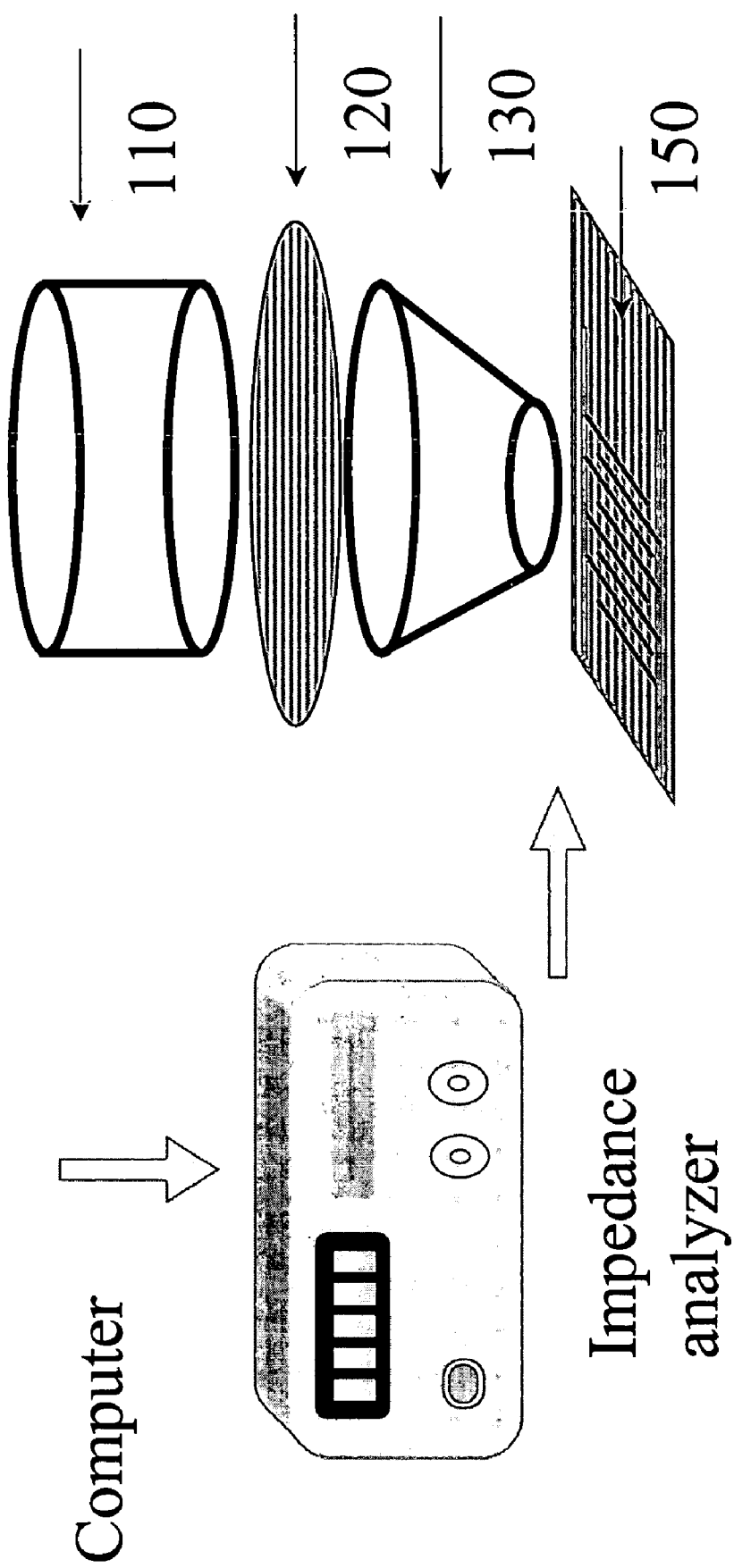
FIG. 1 is a schematic representation of cell migration measurement device, including, top chamber 110, transmembrane well 120, bottom chamber 130 with impedance-based counting electrodes 150. Impedance analyzer can be connected to the electrodes 150 for monitoring cell migration/invasion. In operation, cells having migration/invasion capabilities migrate from top chamber 110 through the pore in the trans-well membrane and reach the bottom chamber. Some or all the cells that migrate from the top chamber to the bottom chamber will land to the bottom surface of the bottom chamber 130, on which the electrodes 150 are located, and become in contact with and adhere to the electrodes 150, resulting in a change of impedance at electrodes 150. Such a change of impedance can be used to monitor the number of cells migrated from the top chamber.
Figure 2:
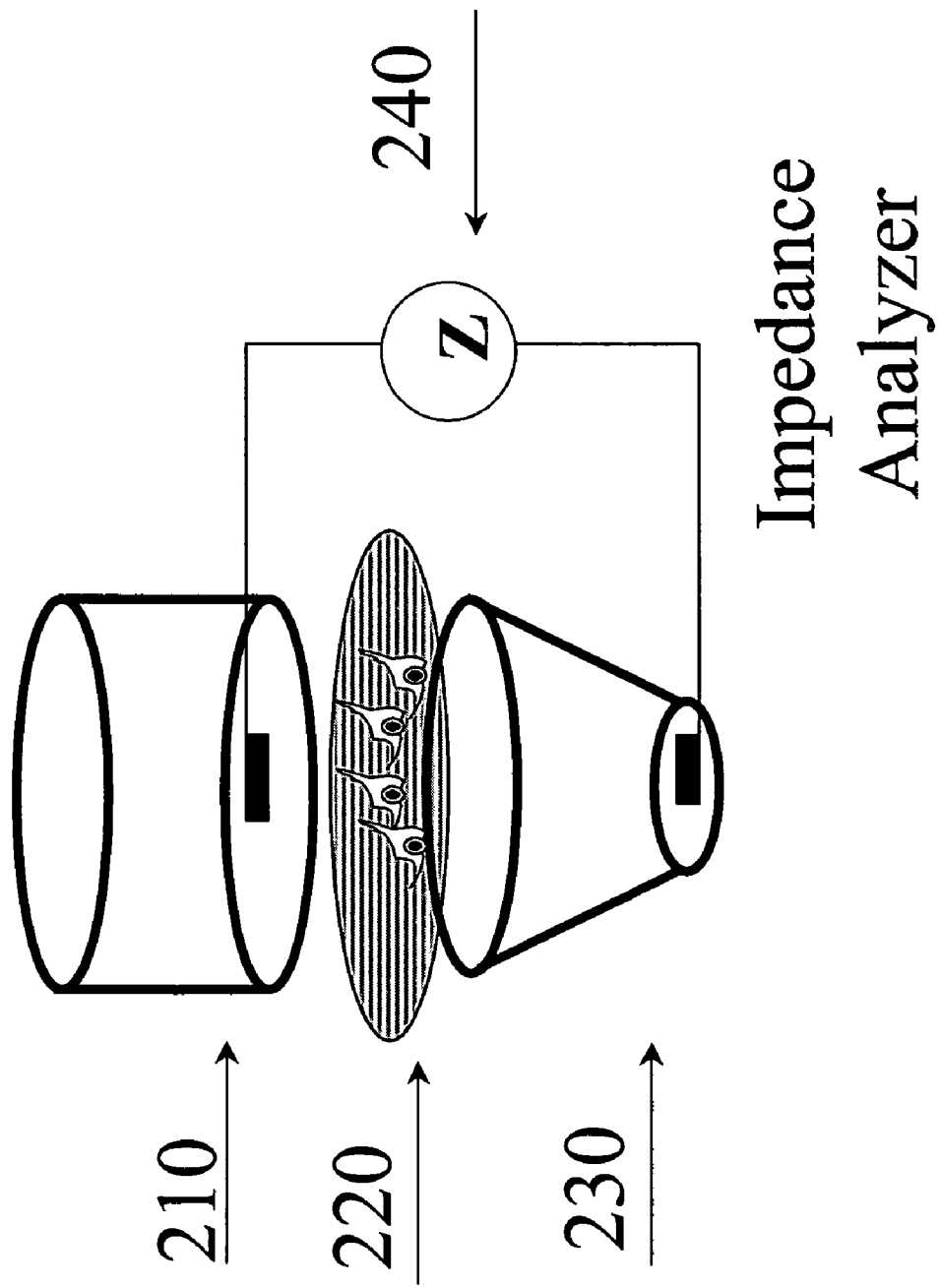
FIG. 2 is a schematic diagram of cell migration by directly monitoring the impedance change between the top chamber 210 and bottom chambers 220 as the cells going through the pores in the membranes 230. The impedance change is monitored by the impedance analyzer 240.

For clarity of disclosure, and not by way of limitation, the detailed description of the invention is divided into the subsections that follow.

The cell-based assay with impedance sensing using the disclosed apparatuses and systems provide a non-invasive measurement so that the cells can be monitored in real-time, continuously, and the cells can be used for other cell-based or molecular-based assays after the impedance-based sensing. The disclosed apparatuses and systems can provide kinetic information as for the cell number, cell biological status (including their attachment status, status, viability, etc.). In addition, the measurement process can be label-reagent free, thus saving the cost for labeling reagents and also saving the labor effort involved in handling and adding those labeling reagents. Furthermore, the entire measurement process can be computer-controlled and fully automated. The researchers need only to seed cells and to add appropriate compounds or media for the required assay process. Finally, the measurement system is accurate with high re-producibility and repeatability. It can also be very sensitive, expressed in the number of the cells per unit area (e.g., about 5 cells/mm $^2$).

A large percentage of the cells added into the wells of the disclosed embodiments are monitored for their contribution to the impedance change between the electrodes in the apparatuses of the present application. This is achieved by a large ratio of the electrode width to the electrode gap and also by, in one embodiment of the apparatuses of the present invention, sensing electrodes covers the entire area of a well in the plate. These embodiments resulting in more cells being monitored for their contribution to the impedance change between the electrodes have the advantage of reducing experimental variation between different wells within a single plate or between wells in different plates. This also improves the measurement accuracy and sensitivity when a small number of cells are used in the assay.

The electrode width, gap width and the electrode element distribution are chosen so that the electrical field distribution is relatively less non-uniform. For example, it is designed that given any two adjacent electrode elements each of which is on a separate electrode structure, the sum of the electrical resistances between each of the two elements to their corresponding connection pads remain nearly-constant for any given two adjacent electrode elements. Thus, the impedance contribution from any two adjacent elements is about the same. So no matter where the cells are landed, their contribution to the impedance change remains to be the same.

Convenient method for the electrode connection allows for the easy scale up of multiple sensors on a single slide.

For certain embodiment of the electrodes used in the impedance sensing, there is a non-uniform electrical field distribution. This has been demonstrated and shown in many dielectrophoresis literature where under certain electrical and cell suspension conditions, cells will experience so-called dielectrophoresis forces and be moved either towards or away from the edge of the electrode elements. For example, following literatures clearly demonstrated these effects for various electrodes: "Selective dielectrophoretic confinement of bioparticles in potential energy wells", by Wang X-B et al, J. Phys. D: Appl. Phys. Vol. 26: pages 1278-1285, 1993; "Positive and negative dielectrophoretic collection of colloidal particles using interdigitated castellated microelectrodes", by Pethig R. et al, J. Phys. D: Appl. Phys. Vol. 25: pages 881-888, 1992. Furthermore, the following theoretical paper provides additional information as for the non-uniform field distribution in interdigitated electrodes: "A theoretical method of electrical field analysis for dielectrophoretic electrode arrays using Greens's theorem", by Wang X-J et al, J. Phys. D: Appl. Phys. Vol. 29: pages 1649-1660, 1996.

Table 1 shows a comparison between result MTT assay and cell impedance sensing measurement. For this experiment, a glass slide having 16 electrode units (each of electrode units has a 3B geometry, see Table 2 below) was used. A plastic strip having 16 wells with a bottom diameter of 5 mm was mounted onto the glass slides by using the liquid adhesive. HT 1080 cells with different numbers were seeded into different wells in the 16×device. The cell number indices were derived by calculating the maximum relative change in the serial resistance measured for each electrode unit. Table 1 shows the cell number indices at time point of 2.5 h after the cell seeding. The well surfaces (including the electrode surfaces were pre-coated with fibronectin by soaking fibronectin solution of a concentration of 50 μg/ml (micro-gram per mL) in the wells for 1 hour. The experiments were stopped at 2.5 h after the impedance measurement. The cells in the same device were used for MTT assay for the comparison. To do the MTT assay, 10 ul of MTT reagent solution was added to each well. The reaction was incubated for 4 hours at 37° C. followed by adding 100 ul/well stop solution. After adding stop solution, the reaction was continuously incubated for 12 hours at 37° C. to solubilize the insoluble purple formazan crystals formed during the MTT reaction. The color density in the device was then measured on a Molecular Device, 96×plate reader at a wavelength of 550 nm. A reference absorbance (at a wavelength of 650 nm.) was used to measure nonspecific readings.

TABLE 1

| Well ID | Cell number | Cell number index | MTT readout |
| --- | --- | --- | --- |
| B1 | 1.54E+04 | 4.74E+00 | 1.43E+00 |
| C1 | 1.19E+04 | 4.71E+00 | 1.43E+00 |
| D1 | 9.13E+03 | 3.73E+00 | 1.18E+00 |
| E1 | 7.03E+03 | 5.80E+00 | 1.01E+00 |
| F1 | 5.41E+03 | 4.41E+00 | 9.40E−01 |
| G1 | 4.17E+03 | 2.79E+00 | 7.62E−01 |
| H1 | 3.21E+03 | 1.59E+00 | 6.86E−01 |
| H2 | 2.47E+03 | 7.99E−01 | 5.99E−01 |
| G2 | 1.90E+03 | 6.94E−01 | 5.39E−01 |
| F2 | 1.47E+03 | 7.67E−01 | 4.29E−01 |
| E2 | 1.13E+03 | 5.89E−01 | 3.83E−01 |

TABLE 1-continued

| Well ID | Cell number | Cell number index | MTT readout |
|---|---|---|---|
| D2 | 8.69E+02 | 3.61E−01 | 3.30E−01 |
| C2 | 6.69E+02 | 2.62E−01 | 3.14E−01 |
| B2 | 5.15E+02 | 1.39E−01 | 2.48E−01 |
| A2 | 3.97E+02 | 1.51E−01 | 2.54E−01 |
| A1 | 0.00E+00 | 9.38E−02 | 2.38E−01 |

A. Definitions

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "at least two electrodes fabricated to a same plane of the substrate" means that, if the insulating substrate has multiple layers, the at least two electrodes are fabricated to the same layer of the substrate.

As used herein, "membrane" is a sheet of material. As used herein, "membrane" is a sheet of material.

As used herein, "biocompatible membrane" means a membrane that does not have deleterious effects on cells, including the viability, attachment, spreading, motility, growth, or cell division.

When a suspension of viable, unimpaired, epithelial or endothelial cells is added to a vessel, a surface of the vessel "is suitable for cell attachment" when a significant percentage of the cells are adhering to the surface of the vessel within twelve hours. Preferably, at least 50% of the cells are adhering to the surface of the vessel within twelve hours. More preferably, a surface that is suitable for cell attachment has surface properties so that at least 70% of the cells are adhering to the surface within twelve hours of plating (i.e., adding cells to the vessel). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating. To have desired surface properties for cell attachment, the surface may need to chemically-treated (e.g. treatment with an acid and/or with a base), and/or physically treated (e.g. treatment with plasma), and/or biochemically treated (e.g. coated with one or more molecules or biomolecules that promotes cell attachment). In the present invention, a biocompatible surface (such as a membrane) preferably is suitable for the attachment of cells of the type that are to be used in an assay that uses the biocompatible surface (e.g., membrane), and most preferably, allows the attachment of at least 90% of the cells that contact the biocompatible surface during the assay.

A "biomolecular coating" is a coating on a surface that comprises a molecule that is a naturally occurring biomolecule or biochemical, or a biochemical derived from or based on one or more naturally occurring biomolecules or biochemicals. For example, a biomolecular coating can comprise an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occuring biochemicals.

An "extracellular matrix component" is a molecule that occurs in the extracellular matrix of an animal. It can be a component of an extracellular matrix from any species and from any tissue type. Nonlimiting examples of extracellular matrix components include laminins, collagens fibronectins, other glycoproteins, peptides, glycosaminoglycans, proteoglycans, etc. Extracellular matrix components can also include growth factors.

An "electrode" is a structure having a high conductivity, that is, a conductivity much higher than surrounding material.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike projection of an interdigitated electrode structure.

As used herein, an "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units.

"Electrode traces" are electrically conductive paths that extend from electrodes or electrode elements or electrode structures toward one end or boundary of a device or apparatus for connecting the electrodes or electrode elements or electrode structures to a signal source. The end or boundary of a device may correspond to the connection pads on the device or apparatus.

As used herein, "the at least two electrodes (electrode arrays) have substantially same surface area" means that the surface areas of any electrodes (electrode arrays) are not substantially different from each other so that the impedance change due to cell attachment or growth on the larger electrode (electrode array) will contribute to the overall detectable change in impedance to a same or similar degree as the impedance change due to cell attachment or growth on the smaller electrodes (electrode arrays). In other words, both larger electrodes (electrode arrays) and smaller electrode (electrode arrays) contribute to overall change in impedance upon cell attachment or growth on these electrodes. Ordinarily, the ratio of surface area between the largest electrode (electrode array) and the smallest electrode (electrode array) is less than 10. Preferably, the ratio of surface area between the largest electrode (electrode array) and the smallest electrode (electrode array) is less than 5, 4, 3, 2, 1.5, 1.2 or 1.1. More preferably, the at least two electrodes (electrode arrays) have nearly identical or identical surface area.

"Interdigitated" means having projections coming one direction that interlace with projections coming from a different direction in the manner of the fingers of folded hands (with the caveat that interdigitated electrode elements preferably do not contact one another).

As used herein, "the apparatus has a surface suitable for cell attachment or growth" means that the electrode and/or non-electrode area of the apparatus has appropriate physical, chemical or biological property so that desirable cells can viably attach on the surface and can keep attaching, while growing, on the surface of the apparatus. However, it is not necessary for the apparatus, or the surface thereof, contains any substances necessary for cell viability or growth. These necessary substances, e.g., nutrients or growth factors, can be supplied in a medium. Preferably, when a suspension of viable, unimpaired, epithelial or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among the electrodes" means that the impedance between or among the electrodes would have a significant change that can be detected by an impedance analyzer or impedance measurement circuit when cells attach or grow on surfaces of the apparatus. The impedance change refers to the difference in impedance values when a surface of the apparatus has cells attached or grown on and when a surface of the apparatus does not have cells attached or grown on. Ordinarily, the change in impedance is larger than 0.1% to be detectable. Preferably, the detectable change in impedance is larger than 1%, 2%, 5%, 8%. More preferably, the detectable change in impedance is larger 10%. Impedance between or among electrodes is typically a function of the frequency of the applied electric field for measurement. "Detectable change in impedance between or among the electrodes" does not require the impedance change at all frequencies being detectable. "Detectable change in impedance between or among the electrodes" only requires a detectable change in impedance at any single frequency or multiple frequencies. In addition, impedance has two components, resistance and reactance (reactance can be divided into two categories, capacitive reactance and inductive reactance). "Detectable change in impedance between or among the electrodes" requires only that either one of resistance and reactance has a detectable change at any single frequency or multiple frequencies.

As used herein, "the at least two electrodes have substantially different surface areas" means that the surface areas of any electrodes are not similar to each other so that the impedance change due to cell attachment or growth on the larger electrode will not contribute to the overall detectable impedance to a same or similar degree as the impedance change due to cell attachment or growth on the smaller electrodes. Preferably, any impedance change due to cell attachment or growth on the larger electrode is significantly smaller than the impedance change due to cell attachment or growth on the smaller electrode. Ordinarily, the ratio of surface area between the largest electrode and the smallest electrode is more than 10. Preferably, the ratio of surface area between the largest electrode and the smallest electrode is more than 20, 30, 40, 50 or 100.

As used herein, a "high probability of contacting an electrode element" means that, if a cell is randomly positioned within the sensor area of a device or apparatus of the present invention, the probability of a cell (or particle) contacting on an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

An "insert tray" is a structure that comprises one or more depressions, or wells (hereinafter called "inserts") that can fit into a fluid container or, if the insert tray comprises multiple inserts, multiple fluid containers or a multiwell plate, such that the one or more inserts of the insert tray form chambers within the fluid container or wells of a multiwell plate. In some aspects of the present invention, an insert tray comprises at least one device of the present invention forming the bottom of at least one insert, such that the chamber formed by the insert when it is placed in a fluid container has as its bottom surface a nonconducting substrate that comprises at least one electrode.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound.

As used herein, "sample" refers to anything which may contain a moiety to be isolated, manipulated, measured, quantified, detected or analyzed using apparatuses, microplates or methods in the present application. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbonhydrates, chemical molecules binding to biological molecules).

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

B. Apparatuses and Methods for Monitoring Cell Migration

In one aspect, the present invention is directed to an apparatus for monitoring cell migration or invasion, which apparatus comprises: a) an upper chamber for placing migrating or invasive cells or cells suspected of being migrating or invasive; b) a lower chamber comprising at least two electrodes; c) a biocompatible membrane comprising multiple holes of a suitable size for allowing said migrating or invasive cells to go through, said membrane connected to said upper and lower chambers and separating said upper chamber and lower chamber from each other, wherein said migrating or invasive cells move through said holes of said membrane and contact and/or attach to said electrodes of said lower chamber to generate a change of impedance between or among the electrodes that can be used to monitor migration or invasion of said cells.

In these aspects of the present invention that comprise an upper and lower chamber separated by a membrane having holes through which migrating or invasive cells can move, in which the lower chamber comprises at least two electrodes, the at least two electrodes of the lower chamber preferably are on the upper surface of the bottom of the lower chamber. In some embodiments of these aspects, the membrane comprises one or more moieties on its lower surface that prevents cell attachment. Non-limiting example of such moieties may be certain formulations of polyethylene glycol. In other embodiments, the membrane is treated either chemical (e.g., acid treatment) or physically (e.g., certain radiation such as plasma radiation) or biologically (e.g. certain coatings of biomolecules) so that the lower surface of the membrane prevents cell attachment and has minimized cell attachment effects. In these aspects, attachment of cells that have moved through the membrane to the bottom of the lower chamber results in an impedance change over electrodes on the surface of the lower chamber bottom.

Figure 19:
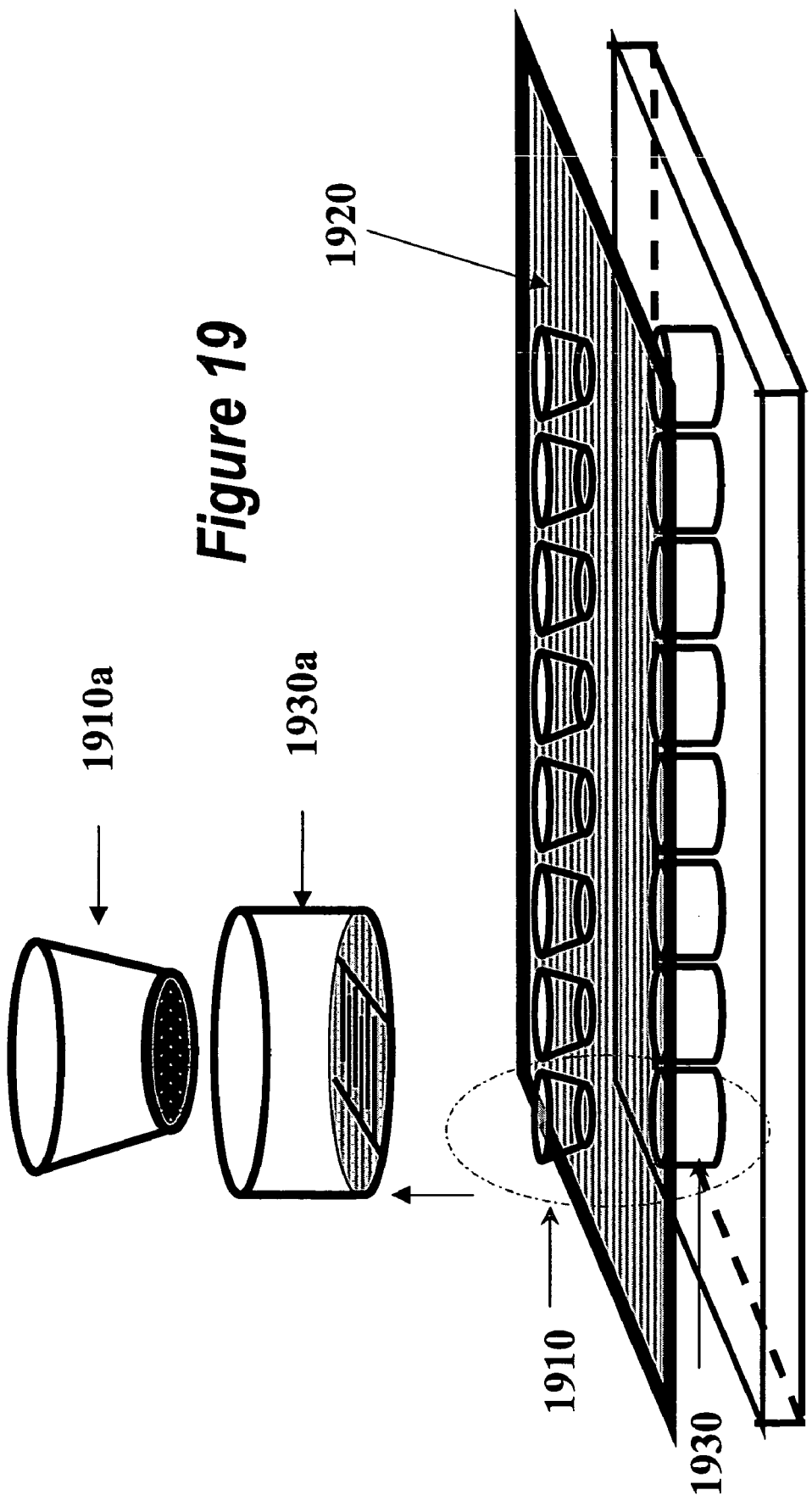
FIG. 19 is a schematic representation of an apparatus that comprises multiple top chambers (1910), trans-well membrane 1920, and bottom chambers (1930). In this case, multiple top chambers (1910) are bonded to the membrane (1920) that have pores of appropriate sizes for cell migration or invasion. Each top chamber (e.g., 1910a) has a corresponding bottom chamber (e.g., 1930a). For each bottom chamber, there are electrode structures on the bottom surface of the bottom chamber, facing the top chamber. In operation, the electrode structures in the bottom chamber are connected to the impedance measuring circuits or instrument via different methods for measuring cells attached and/or adhered to the electrodes. The monitored impedance can reflect the number of cells migrated from the top chamber to the bottom chamber.
Figure 20:
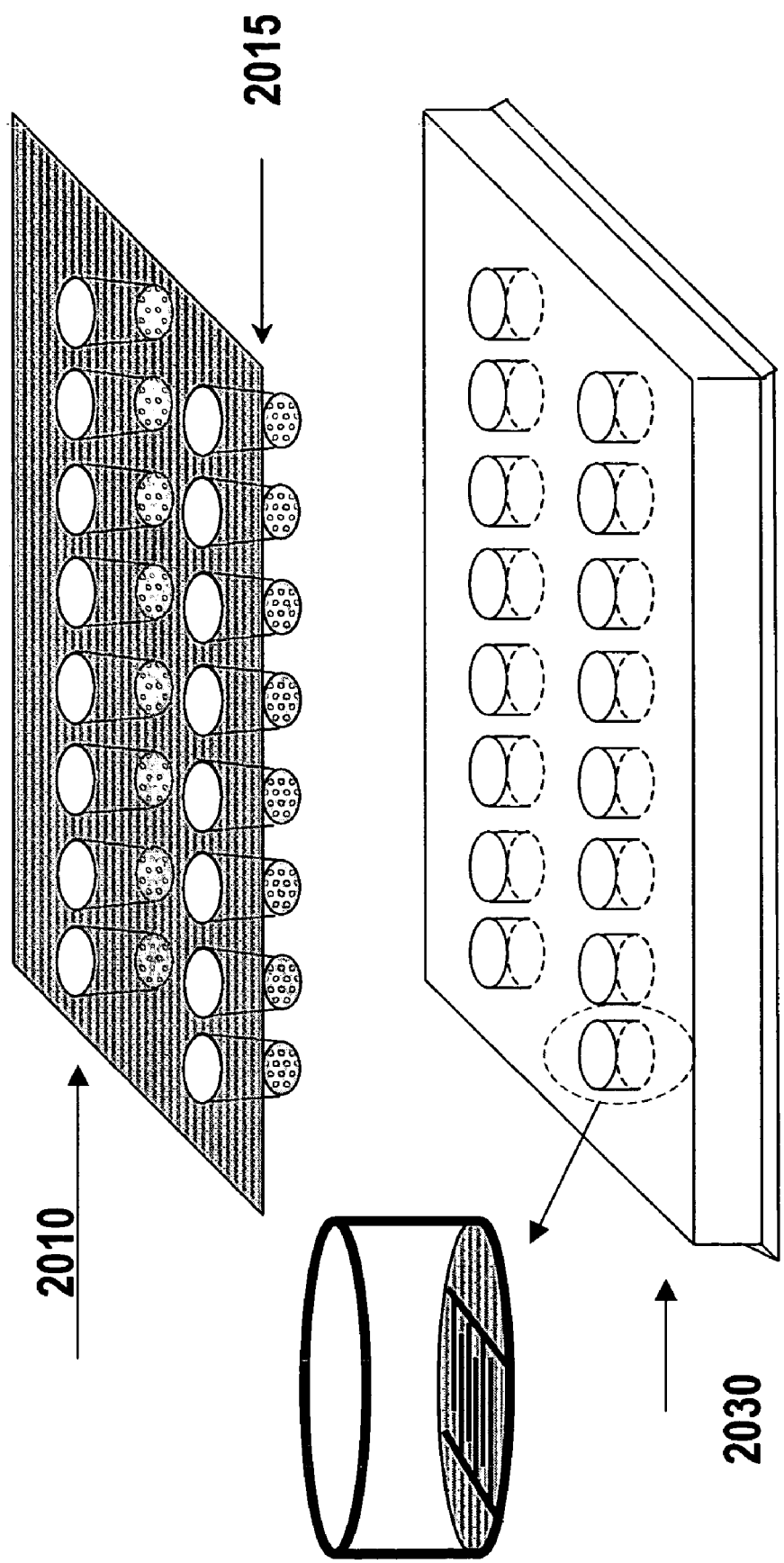
FIG. 20 is a schematic representation of an apparatus that comprises multiple sites for cell migration and invasion measurements. A bottom plate (2030) comprises multiple bottom chambers. Electrode structures are fabricated or incorporated into the bottom surface of each bottom chamber, facing the top chamber. A top plate (2010) comprises multiple insert wells (2015). The bottom surface of each insert well is a membrane. In operation, the top plate (2010) is placed into the bottom plate (2030). The electrode structures on the bottom surface of each bottom chamber are connected to the impedance measuring instruments via various methods.
Figure 21:
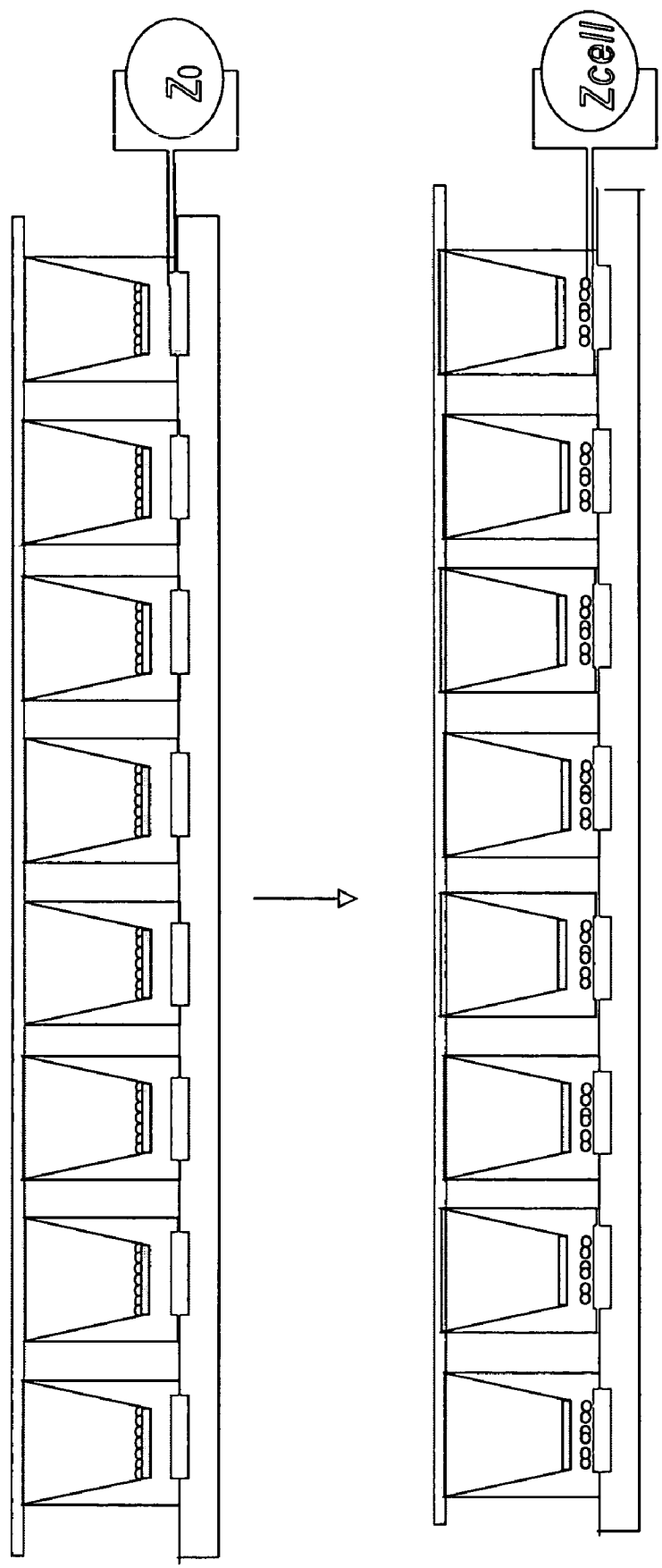
FIG. 21 is a cross-sectional view of cell migration/invasion apparatuses of FIG. 20, illustrating the impedance measurement of the electrode structures located in the bottom chambers prior to cell migration through pores on the membrane (top panel, impedance is $Z_O$) and after cell invasion/migration through pores on the membrane (bottom panel, impedance is $Z_{cell}$)

FIG. 19 and FIG. 20 show two exemplary embodiments of the apparatuses comprising multiple sites for cell migration and invasion. In FIG. 19, the apparatuses comprise multiple top chambers (1910), a trans-well membrane 1920, and multiple bottom chambers (1930). Multiple top chambers (1910) are bonded to the membrane (1920) that have pores of appropriate sizes for cell migration or invasion. Each top chamber (e.g., 1910a) has a corresponding bottom chamber (e.g., 1930a). For each bottom chamber, there are electrode structures on the bottom surface of the bottom chamber, facing the top chamber. The configuration of the bottom chambers comprising electrode structures is the same as, or similar to, the apparatuses described in Section B, above, for monitoring and/or measuring cell-substrate impedance. Thus, the descriptions of apparatuses, multi-well plates, the methods to construct multi-well plates with the electrode-comprising substrates and the methods to connect electrode structures to external impedance measuring circuits described in section B, above, also apply to the lower chambers here for monitoring cell migration/invasion. In operation, the electrode structures in the bottom chamber are connected to the impedance measuring circuits or instrument via different methods for measuring cells that have migrated from the top chamber and have attached and/or adhered to the electrode structures. The monitored impedance can be used to derive cell number index (or called cell migration index) that is indicative of (or reflects) the number of cells migrated from the top chamber to the bottom chamber.

In FIG. 20, the apparatus comprises a top plate and a bottom plate. The top plate (2010) comprises multiple insert wells (2015). The bottom surface of each insert well is a membrane. The bottom plate (2030) comprises multiple bottom chambers. Electrode structures are fabricated or incorporated into the bottom surface of each bottom chamber, facing the insert well. The configuration of the bottom chambers comprising electrode structures is the same as, or similar to, the apparatuses described in Section B, above for monitoring and/or measuring cell-substrate impedance. Thus, the descriptions of apparatuses, multi-well plates, the methods to construct multi-well plates with the electrode-comprising substrates and the methods to connect electrode structures to external impedance measuring circuits described in section B, above, also apply to the lower chambers and the bottom plate here for monitoring cell migration/invasion. In operation, the top plate (2010), which has been loaded with cells for migration/invasion assay in appropriate buffer or medium is placed into the bottom plate (2030), which has been loaded with buffers or media comprising appropriate reagents. The electrode structures on the bottom surface of each bottom chamber can be connected to the impedance measuring circuits or instruments via various methods.

In yet another aspect, the present invention is directed to an apparatus for monitoring cell migration or invasion, which apparatus comprises: a) an upper chamber for placing migrating or invasive cells or cells suspected of being migrating or invasive, said upper chamber comprising an electrode; b) a lower chamber comprising an electrode; c) a biocompatible membrane comprising at least one hole of a suitable size allowing migrating or invasive cells to go through, said membrane connected to said upper and lower chambers and separating said upper chamber and lower chamber from each other, wherein migrating or invasive cells move through the one or more holes of said membrane which results in a change of impedance between the electrodes in the upper and lower chambers that can be used to monitor migration or invasion of the cells.

In yet another aspect of the present invention, the apparatus of the invention will include an upper chamber for receiving cells; b) a lower chamber; c) a biocompatible polymer membrane comprising multiple pores of a suitable size allowing the cells to pass wholly or partially therethrough, wherein the membrane separates the upper and lower chambers from one another; and d) at least two electrodes disposed on the membrane within the lower chamber, such that the active surface of the electrode faces into the chamber.

The biocompatible membrane of the present apparatuses can comprise any suitable material. Non-limiting examples of the material include glass (e.g., quartz glass, lead glass or borosilicate glass), silicon, silicon dioxide on silicon, silicon-on-insulator (SOI) wafer, sapphire, plastics, and polymers. Some preferred polymers are polyimide (e.g. Kapton, polyimide film supplied by DuPont), polystyrene, polycarbonate, polyvinyl chloride, polyester, polyethylene terephthalate (PET), polypropylene and urea resin. Polymers such as polycarbonate, polyester and polyethylene terephthalate (PET) are especially preferred. The biocompatible membrane may be various thickness from as thin as about 2 microns, to as large as about 500 microns. Preferably, a biocompatible membrane of a device of the present invention is between about 5 and about 50 microns thick, and more preferably between about 8 and about 25 microns thick.

Any surface of the nonconducting substrate that can be exposed to cells during the use of a device or apparatus of the present invention is preferably biocompatibie. Preferably, at least one surface of the nonconducting substrate is suitable for cell attachment or growth. Substrate materials that are not biocompatible or do not allow cell attachment or growth can be made suitable for cell attachment and growth by coating with another material, such as a polymer or biomolecular coating. Thus, the surface of a biomembrane of a device of the present invention can comprise a material, such as a plastic, that is suitable for cell attachment and growth, or, alternatively or in addition, can comprises a coating that allows cell to adhere to the surface of the biomembrane.

The biocompatible membrane can optionally comprise a coating that can promote the attachment of one or more cells. The coating can be a polymer, such as a plastic film, or one or more biomolecules or one or more derivatives of one or more biomolecules, such as, but not limited to a polymer such as polyornithine or polylysine, peptides or proteins, or extracellular matrix components (or derivatives or analogues thereof), including, but not limited to, gelatin, fibronectin, laminin, collagen, a glycosaminoglycan, a peptidoglycan, etc. Such coatings can preferably but optionally cover the entire surface of a substrate that is exposed to or can be contacted by cells during the use of a device, including the electrode surfaces.

A coating can be a semi-solid or gel, and can optionally comprise additional components such as, but not limited to, growth factors. A coating can be a simple or complex mixture of biomolecules and can simulate or replicate a naturally occurring extracellular matrix (ECM.) For example, Matrigel™ Basement Membrane Matrix (BD BioSciences) is a solubilized basement membrane preparation extracted from the Engelbreth-Holm-Swarm (REHS) mouse sarcoma, a tumor rich in extracellular matrix proteins. Its major component is laminin, followed by collagen IV, heparan sulfate proteoglycans, entactin and nidogen. It also contains TGF-beta, fibroblast growth factor, tissue plasminogen activator, and other growth factors which occur naturally in the EHS tumor.

A coating that simulates or replicates an ECM can promote cell attachment. A coating that simulates or replicates an ECM can also, in some aspects of the present invention, provide a barrier for cell migration/invasion. The ability of cells to penetrate an ECM-like barrier (such as, but not limited to, Matrigel™) can be tested in invasion assays using a device or apparatus of the present invention.

The biocompatible membrane of the present apparatuses can comprise one or more holes (preferably multiple holes) of any suitable sizes that allow cells whose migratory or invasive behavior is to be investigated to go through. The biocompatible membrane can comprise multiple holes of a same size. Alternatively, the biocompatible membrane can comprise multiple holes of different sizes. Preferably, the size of the hole or holes limits the number of cells that can simultaneously pass through a hole to fewer than three and more preferably to one cell. For example, the membrane can comprise multiple holes of a same size that are, for mammalian cancer, epithelial, or endothelial cells, between about 1 micron and about 30 microns in diameter, more preferably between about 2 microns and about 10 microns in diameter.

In other preferred embodiments of the present invention, the one or more pores of a biocompatible membrane have a diameter that does not permit the passage of cells used in measuring electrical impedance, resistance, or capacitance of a cell/substrate interface through the pore. For example, the one or more pores can be less than about 5 microns, or preferably less than about 1 micron. In some aspects of these embodiments, the one or more electrodes fabricated on the membrane can be used to measure the change in impedance when a layer of cells grown on the membrane is disrupted by invasive cells. In other aspects of these embodiments, growth, attachment, detachment, morphology, or motility of cells on the membrane can be monitored.

Each electrode pair is electrically connected to an impedance analyzer. The impedance can be analyzed or measured in any suitable frequency range, e.g., a frequency range between about 1 Hz and about 100 MHz, or between 10 Hz and about 5 MHz.

Most preferably, at least one electrode in each electrode pair is adapted to bind cells which have passed wholly or partially through the porous membrane. The electrodes of the present apparatuses for monitoring cell migration can have any suitable surface areas. For example, the electrodes between or among which the impedance is measured to monitor cell migration or adhesion can have substantially same or different surface area. In still another example, each of the electrodes can have a surface area sufficient for attachment of at least 10 cells.

In preferred aspects of the present invention, two or more electrodes are fabricated on one side of a biocompatible membrane. Preferably at least two of the two or more electrodes have substantially the same area. At least two electrodes having substantially the same area are preferably part of the same electrode structure unit.

Figure 15:
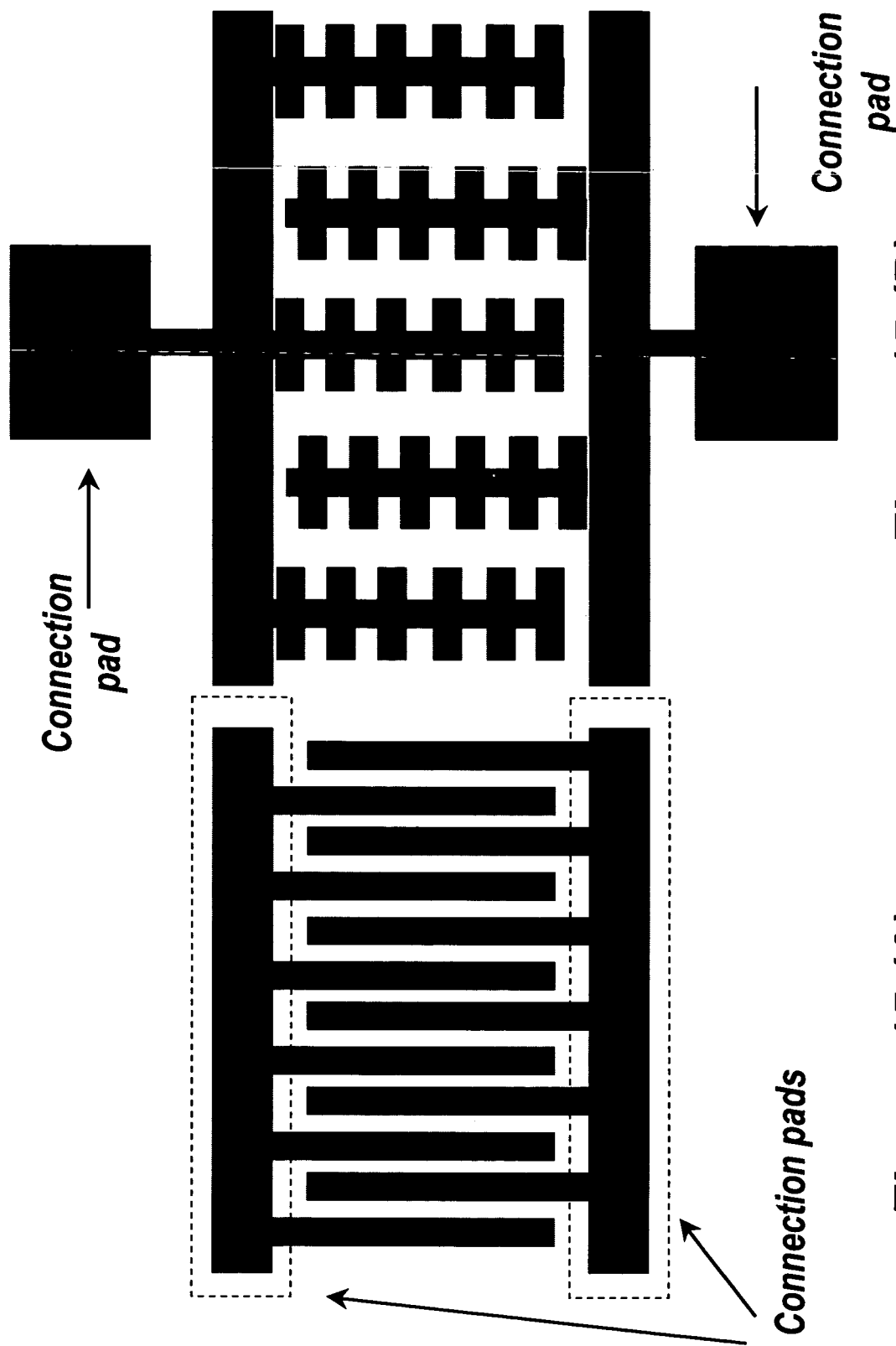
FIG. 15 is a schematic representation of electrode geometries that can be used in FIG. 14 for monitoring cell migration/invasion. 15(A), interdigitated, parallel line electrode array, where the electrode width can be larger, equal to, or smaller than the electrode gaps; 15(B) castellated, offset electrode structures; 15(C) electrode structures with disc electrodes added on the electrode lines; 15(D) castellated, straight electrode structures; 15(E) sinusoidal electrode structures; 15(F) concentric electrode structure. The characteristic dimension of the electrodes can be as small as less than 10 microns, or as large as over several hundred microns. The total active electrode area can be of different shapes such as regular shapes like rectangular shapes (FIGS. 15(A), 15(B), 15(E)), or circle-like shapes (FIGS. 15(C), 32(D)), or other regular or irregular shapes. Preferably, the total electrode-region area (the area including the electrodes and the gaps between the electrodes) covers nearly the complete bottom surface of the top chamber. Electrode structures are connected to impedance measurement circuits (e.g. an impedance analyzer) via connection pads (as illustrated in FIGS. 15(A) and 15(B)) that are either directly linked to electrode elements (FIG. 15(A), FIG. 15(C) and FIG. 15(E)) or connected to electrode elements through additional electrical connection (FIG. 15(B) and FIG. 15(D)).

The electrodes or electrode elements within an electrode structure in the present apparatuses can have any suitable shape, e.g., a rectangular, circular, a circle on a rectangular line ("circle-on-line"), a square on a rectangular line or a sinusoidal line. They can also take the form of curved lines such as, but not limited to spirals or arcs. Some examples of electrodes, electrode structures or electrode structure units for the device of the present invention are shows in FIGS. 9 and 15.

Figure 15D:
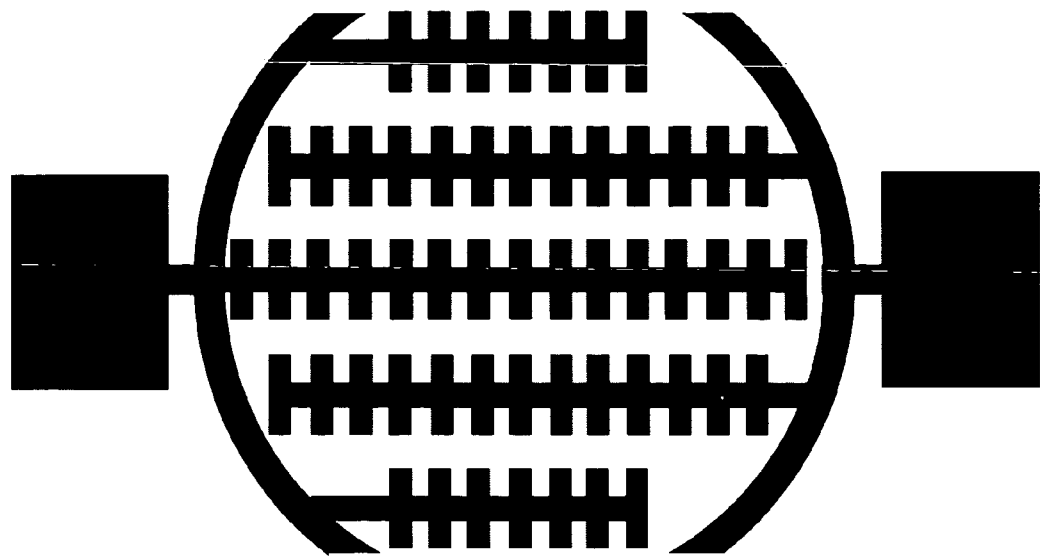
In FIGS. 15(A), (C) and (E), connection pads are also the electrically-conducting connection paths that connect electrode elements within an electrode structure.
Figure 15C:
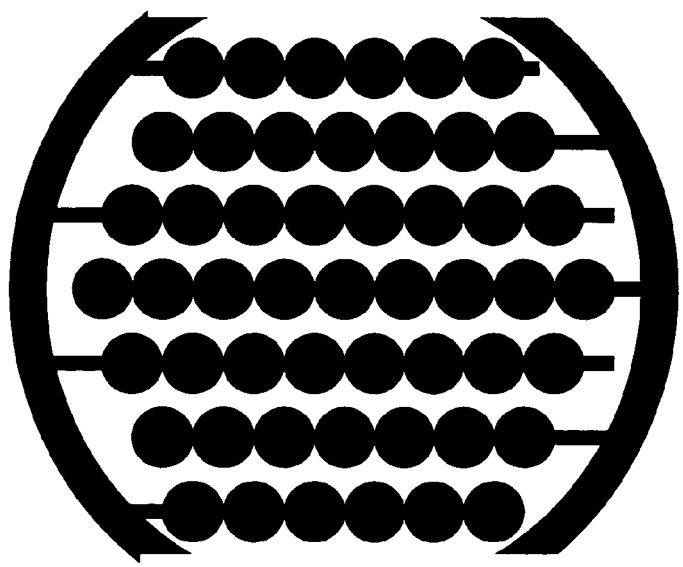
Figure 15F:
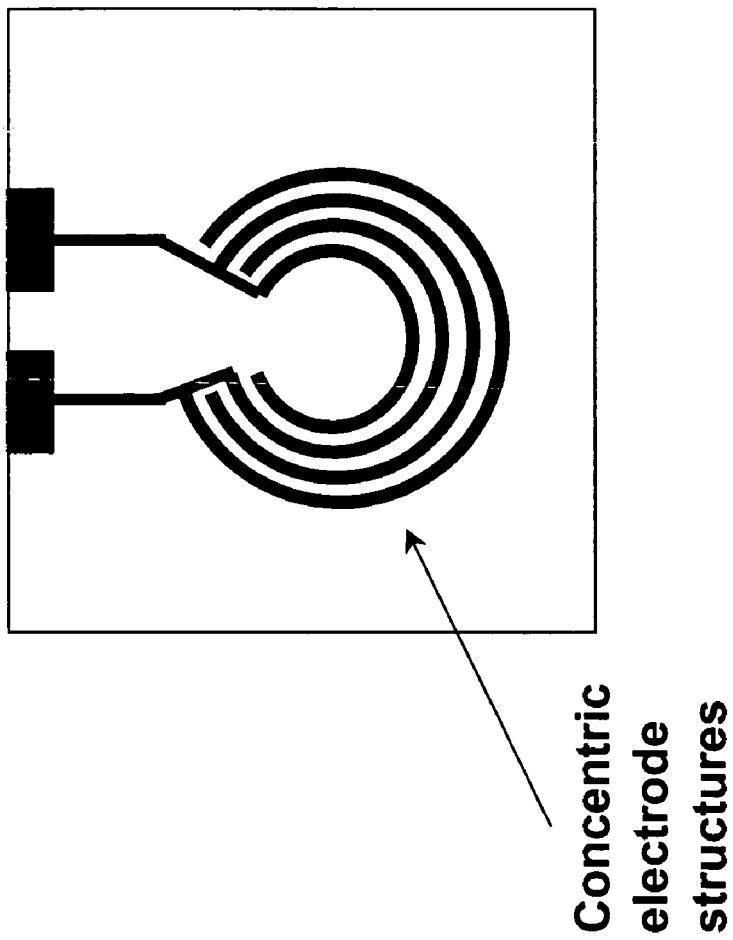
Figure 15E:
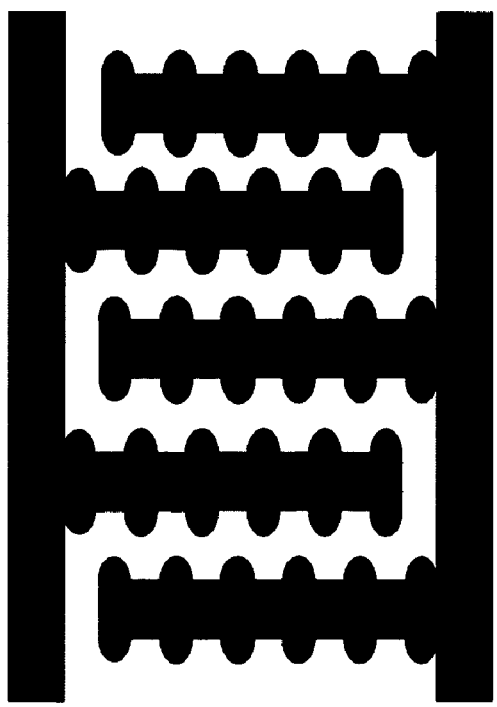

In some preferred embodiments of the present invention, electrode structures can be interdigitated electrode structures (IDESs) or concentric electrode structures (CCESs), such as those depicted in FIGS. 15A and 15F. For example, an electrode structure can comprise two or more electrodes configured as one or more IDESs or one or more CCESs. Interdigitated electrode structures (IDESs) can be further modified or changed so that the parallel line electrode elements have large perimeter subgeometries, meaning that, as viewed from above, superimposed on the linear electrode elements (which may itself be parallel lines, curved, loop, form angles, turn corners, etc.) are branches, outcroppings, bulges, and the like, giving the linear electrode path a larger perimeter than if its edges conformed to the directionality of the path of the electrode element. Examples of such large perimeter structures are a diamond-on-line electrode structures, circle-on-line electrode structures shown in FIG. 15C, castellated electrode structures as shown in FIGS. 15B and 15D. Electrode structures with large perimeter subgeometries are not limited to those depicted herein, and can be regular or irregular, both in the periodicity of the subgeometries and in the shapes of the subgeometries (curves, angles, circles, rectangles) themselves.

Electrodes or electrode elements are preferably distributed over the entire surface region of the device they are fabricated on, wherein such surface region is or will be exposed to contact by cells. In another word, the surface region that is or will be exposed to contact by cells is covered with electrodes (or electrode elements) and gaps between electrodes (or electrode elements). In preferred devices of the present invention, the sensor area can occupy at least 5%, 10%, 30%, 50%, 70%, 80%, 90%, 95% or even 100% of the entire surface region of the device, wherein such surface region is exposed to or will be exposed to cells under the assay. In another word, in preferred devices of the present invention, at least 5%, 10%, 30%, 50%, 70%, 80%, 90%, 95% or even 100% of the surface region that is exposed or will be exposed to the cells under the assay is covered with electrodes (or electrode elements) and gaps between electrodes (or electrode elements). Preferably, the distribution of electrodes or electrode elements over the sensor area is uniform or approximately uniform.

In embodiments in which a device comprises at least two electrode structures, the two or more electrode elements are preferably arranged in the electrode structures. Where an electrode element is not of rectangular geometry, "electrode width or electrode element width" refers to the averaged dimension of the electrode element that extends in the plane of the substrate (in the direction normal to the major axis of the electrode element) from where it borders one electrode gap to where it borders the electrode gap on its opposite side. Where an electrode gap is not of rectangular geometry, "electrode gap" refers to the averaged dimension of the gap that extends in the plane of the substrate (in the direction normal to the major axis of the gap) from where it borders one electrode element to where it borders the other electrode element on its opposite side. For the present invention, the substrate refers to the material on which the electrodes are fabricated. For example, if the electrodes are fabricated on a biocompatible membrane, then the membrane is the substrate.

For monitoring the behavior of cells, preferably, the gap between electrode elements does not substantially exceed the size (e.g. width of cells when they spread and attach on the substrate) of cells whose behavior is to be monitored using the device. This reduces the possibility that contact between a cell and a substrate occurs without the cell contacting at least a portion of an electrode or electrode element. Further, the width of the gap between electrode elements (or the gap size) preferably is not substantially less than the size of cells (e.g. width of an average cell when it spreads and attaches to the substrate) whose behavior is to be monitored using the device, to reduce the possibility of a cell contacting two neighboring electrode elements is measured and thereby giving rise to a somewhat disproportionately large impedance signal, in comparison to a cell contacting only one electrode element. This is particularly important, if the electrode width is much larger (e.g. ten times) than the size of cells whose behavior is to be monitored using the device. On the other hand, if the electrode width is in comparable with the size of cells (e.g. width of an average cell when it spreads and attaches to the substrate), the width of the gap between electrode elements can be somewhat smaller than the size of cells. While other gap diomensions may be used, preferably, the gap between electrode elements of the electrode structures ranges from about 0.2 times and 3 times the width of an average cell used in an assay using the device. Preferably, the width of a gap between electrodes or electrode elements of a device of the present invention used for monitoring eukaryotic cells, such as mammalian cells, such as cancer cells, endothelial or epithelial cells, is between about 3 microns and 80 microns, more preferably between about 5 microns and 50 microns, and most preferably between about 8 microns and 30 microns.

The width of an electrode element is preferably not too narrow since the resistance of the electrode elements will increase as the width of the electrode element decreases. The increased resistance along the electrode elements will cause a large electrical potential difference between different points along the electrode element, resulting in difference impedance signals for cells landed on and attach to different regions of the electrode elements. It is preferred that cells landed on and attached to any region on the substrate surfaces give similar impedance signals. Thus, for an electrode element that is part of an interdigitated electrode structure or concentric electrode structure, where the device is to be used for monitoring eukaryotic cells, such as mammalian cells, such as cancer cells, endothelial or epithelial cells, the electrode width is preferably greater than about 3 microns, and more preferably greater than about 10 microns. The width is also limited by the consideration that if an electrode element is very wide, a cell that is positioned over a central part of such a very wide electrode will result in a small impedance signal when compared with that of a cell that is positioned over the edge of an electrode, where the field strength can be significantly higher. Preferably, an electrode element's width is between about 0.5 times and about 10 times the size (e.g., the width of an average cell when it spreads and attaches to the substrate) of cells used in an assay that uses the device. Preferably, for an electrode element that is part of an IDES or CCES, where the device is to be used for monitoring eukaryotic cells, such as mammalian cells, such as cancer cells, endothelial or epithelial cells, an electrode or electrode element is less than about 500 microns wide, and is preferably less than about 250 microns wide. In some preferred embodiments of the present invention, an electrode element is between about 20 microns and about 250 microns wide.

In the present application, it is preferred that the electrode gap between electrode elements should be designed with respect to the electrode width. While other ratios of the electrode element width to gap may be utilized, preferably, the ratio of electrode element width to gap width is between about 1:3 and 20:1. Preferably, the electrode element width is between 1.5 and 15 times the gap width. More preferably, the electrode element width is between 2 and 6 times the gap width; for example, if the electrode width is 90 microns at the widest point of each electrode, the gap width would be about 20 microns at the widest point of the gap between adjacent electrodes. For the present application, the electrode width can range from less than 5 microns to more than 10 mm. Preferably, the electrode width is in the range between 10 micron and 1 mm. More preferably, the electrode width is in the range between 20 micron and 500 micron.

Non-limiting examples of materials for electrodes or electrode elements are indium tin oxide (ITO), chromium, gold, copper, nickel, platinum, silver, steel, and aluminum. Electrodes can comprise more than one material. Choice of appropriate materials for making electrodes depends on several factors: whether the material is conductive enough, how difficult it is for patterning such material on a substrate, whether the material can be reliably used for performing molecular detection assay of the present invention.

Electrode or microelectrodes of the present invention can be of any electrically conductive material. For example, gold (Au), platinum (Pt) can be used. When substrates such as plastics or polymer membranes are used, an adhesion layer of metal such as Cr and Ti can be used. In order to reduce the electric resistance of the electrodes, electrodes with conductive thin films are desirable to have certain thickness. As a non-limiting example, electrodes can be made with a 300 Angstrom Cr layer overlaid by 2000 Angstrom Au. Such electrode layers will be optically non-transparent. Alternatively, optically-transparent electrodes can be used in a device of the present invention. Examples of optically transparent electrodes include indium-tin-oxide (ITO). With appropriate thickness of ITO layer, the transmittance of light through an ITO film electrode can be as high as 98%. In other cases, sufficiently thin conductive films (e.g. a very thin gold film) can be used as optically transparent electrodes. Choice of appropriate materials for making electrodes depends on several factors: whether the material is bio-compatible and is not cyto-toxic, the material is conductive enough, how difficult it is for patterning such material on a membrane substrate.

In one aspect of the present invention, the electrodes of the present devices or apparatuses are fabricated on a biocompatible membrane for monitoring cell migration or invasion. Various microfabrication methods can be employed for making such electrodes on a biocompatible membrane. One example is to use a photolithography technique. In one exemplary approach of photolithography methods, one side of a biocompatible membrane is first deposited with a thin layer metal film (for example, a gold film of about 0.2 µm over a seeding Cr layer of 10 nm) using methods such as vapor deposition and/or sputtering. Photoresist (for example, photoresist S1830 from Shipley) is spin-coated on to the gold film to certain thickness (e.g. 1 µm) and then exposed to UV light through a mask containing an image of required electrode array. The exposed resist is developed using a corresponding developer for the photoresist (e.g., MF351 developer from Shipley), and the gold and chrome layers are etched subsequently with $KI/I_2$ and $K_3Fe(CN)_6/NaOH$, respectively. Masks are produced commercially using electron-beam writing techniques on ultra-high resolution plates. Due to the "flexible" nature of thin membrane, special care may need to be taken in order to reproducibly and accurately make microelectrode structures on the membrane using photolithography methods. In particular, care should be taken to ensure that the membrane is stretched flat and made in good contact with the mask during the photo-masking process. In addition, as the membrane has at least one hole of appropriate size for cell migration/invasion, and if the hole or holes are present prior to electrode fabrication, care should be taken not to affect those holes during the fabrication process. In the alternative, pores can be made after electrode fabrication, using fabrication or micromachining methods such as laser drilling. Those who are skilled in the art of photolithography fabrication and other microfabrication and micromachining methods can readily choose and use appropriate materials and procedures for fabricating microelectrodes and fabricating pores.

Another method of fabricating or patterning microelectrodes is to use laser ablation. For laser ablation, one side of a membrane is first deposited with a thin layer metal film (for example, a gold film of about 0.1 µm over a seeding Cr layer of 10 nm) using methods such as vapor deposition and/or sputtering. The thin metal film is then exposed to a laser (e.g., an excimer laser at 248 or 351 nm) at appropriate intensity through a mask containing an image of required electrode array. At the regions where the mask is "transparent" to the laser, the laser hits and interacts with the metal film and the metal film is ablated off from the membrane. Since the membrane (e.g. a polymer membrane) reacts differently with the laser from the metal film, it is possible to choose appropriate laser condition (wave length, intensity, pulse width) so that the laser can ablate the metal film and has no effect or minimal effect on the membrane. At the regions where the mask is "blocking" the laser, the metal films remain on the membrane. Masks are produced commercially using electron-beam writing techniques on ultra-high resolution plates. Due to the "flexible" nature of thin membrane, special care may need to be taken in order to reproducibly and accurately make microelectrode structures on a membrane using laser ablation methods. In particular, care should be taken to ensure that the polymer membrane is stretched flat during the mask-based laser ablation process. Those who are skilled in laser ablation and thin film patterning with laser ablation can readily choose appropriate procedure and laser wave length, intensity, masks for producing electrodes on the polymer membranes.

If the fabrication process for fabricating the holes and electrodes or electrode structures on the biocompatible membranes permits, it may be possible to ensure the pores for cell migration/invasion are located at regions corresponding to the electrode surfaces, rather than in the gaps between electrodes or electrode elements. Although this is not a requirement or a limitation of the present invention, it is a preferred embodiment of a device for some aspects of the present invention. For example, in one aspect of the present invention, the biocompatible membrane attached to the bottom of a top chamber (or an upper chamber) has electrode structures on the surface facing a bottom chamber (or lower chamber). The details of such structures and their uses are described in the following subsection "Apparatuses Comprising Upper and Lower Chambers" (below). In operation, the cells in their appropriate media are introduced into the top chamber and are monitored for their migration behaviors through the biocompatible membrane by measuring impedance change as a result of cell migration to the bottom chamber rand attachment to the electrode structures on the membrane. The advantage of having the pores for cell migration/invasion located on the regions of the membrane which correspond to the electrode areas is that when cells migrate through a pore, they come into contact with and attach to the electrode surface as they exit the pores in the membrane. Linking attachment to the electrode surfaces to migrating through pores by fabricating pores at the locations of electrodes ensures that all the cells that have migrated through pores in the membrane can contribute to measured impedance changes.

The electrode elements, the electrodes, the electrode structures and the electrode structure units in the present apparatuses can have any suitable configurations, surface areas or surface modifications. In one example, at least one of the electrode structures can have at least two electrode elements. In still another example, the electrode or electrode structure surface area can be modified with a cell-adhesion promotion moiety. Any suitable cell-adhesion promotion moieties, such as a self-assembly-monomolecular (SAM) layer (e.g., alkanethiolates on gold and alkylsiloxanes on $SiO_2$ or $SiO_x$,), a protein (e.g., fibronectin, gelatin, collagen, laminin, proteins that promotes specific or non-specific cell attachment to the electrode or electrode array surface area), a peptide (e.g., poly-L-lysine), a polymer layer and a charged group, can be used in the present apparatuses.

Preferably, the electrodes, electrode structures, and electrode elements are configured such that the electrode traces lead from the electrodes at the substrate surface to an edge or end of the substrate (for example, a biocompatible membrane), where they can be connected with a line from an impedance measurement circuit or a signal source. Here the edge or the end of the substrate where the electrode traces end may correspond to the connection pads on the substrate. In preferred aspects of the present invention, the trace or traces from electrode elements of one electrode structure are insulated from the traces from electrode elements of another electrode structure. In one type of arrangement, electrode traces are located on separate regions of the substrate such that they do not contact each other where their paths cross. In another arrangement, where electrode traces need to cross each other, an insulating material layer can be sandwiched between the electrode traces. Fabrication of such apparatuses or device may involve multi-layer microfabrication processes.

The present apparatuses can further comprise one or more impedance analyzer connected to one or more connection pads. Electrode can directly or indirectly connect to a connection pad, where they connect to a line from an impedance analyzer. A connection pad is preferably at the edge or perimeter of a device of the present invention, but this is not a requirement of the present invention. The connection between electrodes and a connection pad can optionally be via a connecting path that can be localized to an end of the substrate. In an exemplary embodiment of the present invention, the biocompatible on which electrodes are fabricated will be part of, attached to, or within a plate or a fluid container that can contain sample solutions. In these embodiments a connection pad can be situated on a fluid container or plate comprising one or more fluid containers.

Depending on the uses, the present apparatuses or devices can be in any suitable size. In one example, the present devices can have a size to be compatible with automatic plate handling stations. In such cases, multiple measurement units are incorporated into a single plate. For example, in FIGS. 16-21, each apparatus comprises 16 measurement units within each a cell migration assay can be performed.

The lower chamber of the present apparatuses can have any suitable surface areas. For example, the lower chamber can have a bottom surface area sufficient for attachment of about 1-10, 10-100, 100-300, 300-700, 100-1000, 700-1,000, 1,000-3,000, 3,000-6,000, 6,000-10,000 or 1000-10000 cells. In another example, the electrode(s) covers at least 5% of the bottom surface area of the lower chamber. In still another example, the bottom surface area of the lower chamber is less than 10 mm$^2$, or less than 3 mm$^2$, or less than 1 mm$^2$, or less than 300 µm$^2$, or less than 100 µm$^2$.

The electrode(s) can be in any suitable form and can be located in any suitable places of the present apparatuses. For example, the electrode(s) in the lower chamber can be on the bottom surface of the lower chamber. In preferred embodiments, the sensor area can occupy at least 2%, 5%, 10%, 20%, 30%, 40%, 50%, 60%, 70%, 80%, 90%, 95%, 99% or 100% of the entire bottom surface of the lower chamber. In another example, the electrode(s) or electrode structure(s) in the lower chamber can be on the side walls of the lower chamber. In still another example, the electrodes can be needles in the chambers. In yet another example, the electrode(s) can comprise an electrode structure having at least two electrode elements. In yet another example, the electrode(s) can have a shape of a rectangle, a circle, a circle on a rectangular line or a sinusoidal line.

In one embodiment, the lower chamber of the present apparatuses can comprise a modulator of cell migration or invasion, e.g., a chemoattractant, or other reagents that may stimulate or inhibit cell migration/invasion. Alternatively or in addition, the upper chamber of the present apparatuses can comprise a modulator of cell migration or invasion.

In preferred embodiments of the present invention, a system that comprises a device of the present invention also includes interface electronics, including impedance measurement circuit and switches (e.g. electronic switches), to control and switch the impedance measurement circuits to electrode structure units of devices of the present invention. Preferably, a system of the present invention also includes a computer having software programs that can enable real-time measurement or monitoring of impedance between the electrodes or electrode structures of the apparatuses of the present invention. The measured impedance data can be automatically analyzed and processed to derive appropriate parameters (e.g. cell number index, or cell migration index) and displayed on a monitor.

Preferably, the software program has one or more of the following functions: (1) electronically switching for connecting impedance measuring circuit (or analyzer) to one of multiple devices of the present apparatuses; (2) controlling impedance measurement circuit (or analyzer) for measurement of impedance between or among electrodes or electrode structures at one or multiple frequencies; (3) processing the acquired impedance data to derive appropriate biologically relevant parameters (e.g., cell number index, or cell migration index); (4) displaying the results on a monitor or storing results; (5) automatically performing above functions 1 through 4 at regular or irregular time intervals.

Apparatuses Comprising Upper and Lower Chambers

In one aspect, the present invention is directed to an apparatus for monitoring cell migration or invasion, which apparatus comprises: a) at least one upper chamber for placing migrating or invasive cells or cells suspected of being migrating or invasive; b) at least one lower chamber; c) a biocompatible membrane comprising multiple holes of a suitable size allowing said migrating or invasive cells to go through, said membrane connected to said upper and lower chambers and separating said upper chamber and lower chamber from each other, said membrane further comprising at least two electrodes located on the side of said membrane that faces said lower chamber, wherein said migrating or invasive cells move through said holes of said membrane and contact and/or attach to said electrodes of said membrane to generate a change of impedance between or among the electrodes that can be used to monitor migration or invasion of said cells.

Ordinarily, each fluid container of the cell migration apparatuses of the present invention should have a surface area sufficient for attachment or growth of multiple cells. In one example, the fluid containers of the present apparatuses can have a surface area sufficient for attachment of at least 10 and preferably at least 50 cells. In another example, each pair of the electrodes or each pair of electrode structures within a present apparatus that is connected to an impedance analyzer can have a surface area sufficient for attachment of at least 10 and preferably at least 50 cells.

In one embodiment of the above apparatus, the biocompatible membrane further comprises gels or other coating layers on the side facing the upper chamber. The gels or coating layers provide a barrier to cell migration/invasion. The biocompatible membrane can comprise coatings on either or both sides, such as, for example, a coating of one or more extracellular matrix components on the upper side, and polylysine on the lower side.

In another embodiment of the above apparatus, the bottom chamber further comprises reagents that can promote or inhibit cell migration or invasion. Alternatively or in addition, the upper chamber can comprise reagents that can promote or inhibit cell migration or invasion.

A lower chamber of the present apparatuses can have any shape for example, cylinder shape, rectangular shape and other shapes. A lower chamber can be made of various materials including polymers, plastics, or glass. A lower chamber can be of various volume and sizes. A lower chamber of the present apparatuses can have any suitable surface areas. In one example, the bottom surface area of the lower chamber may be as small as 1 mm$^2$, or larger than 50 mm$^2$ In a another example, the bottom surface area of the lower chamber is less than 10 mm$^2$, or less than 3 mm$^2$, or less than 1 mm$^2$, or less than 300 µm$^2$, or less than 100 µm$^2$.

An upper chamber of the present apparatuses can have any shape for example, cylinder shape, rectangular shape and other shapes. An upper chamber can be made of various materials including polymers, plastics, or glass. An upper chamber can be of various volume and sizes. The bottom surface of the upper chamber is made of biocompatible membrane that comprises at least one hole of appropriate sizes for cell migration/invasion. The membrane may be bound to upper chamber walls. The area of the bottom surface of the upper chamber (i.e. the corresponding area of the membrane) can have any suitable size for conducting a cell migration/invasion assay. For example, the area may be as small as 1 mm$^2$, or larger than 50 mm$^2$. In another example, the bottom surface of the upper chamber is less than 10 mm$^2$, or less than 3 mm$^2$, or less than 1 mm$^2$, or less than 300 μm$^2$, or less than 100 μm$^2$.

An apparatus of the present invention that comprises an upper chamber and a lower chamber separated by a device of the present invention can be made by any suitable methods. For example, a top chamber structure comprising at least one tube or bottomless well can be attached to a device of the present invention and a bottom chamber structure (in the form of at least one well) can be attached (such as reversibly attached) to the top structure having the attached membrane.

In an alternative, a vessel (such as a well or a structure having one or more wells) having a bottom surface can be used to fabricate a device of the present invention on the bottom surface using, for example, laser patterning of electrodes and laser drilling of pores. In this case, the bottom surface is in the form of a biocompatiable membrane. A bottom chamber structure can then be attached to the top chamber structure.

An apparatus of the present invention can be part of a system, which includes an impedance analyzer or impedance measuring circuit connected to at least two electrodes of the apparatus. Preferably, the electrodes of an apparatus of the present invention connect to an impedance analyzer or impedance measuring circuit at at least one connection pad. Electrodes can directly or indirectly connect to at least one connection pad, where they connect to lines from impedance measuring circuit or impedance analyzer. In an exemplary embodiment, a connection pad can be situated on a top chamber structure (a top plate) comprising one or more fluid containers, preferably near or at the edge or perimeter of the bottom surface of the apparatus.

In preferred embodiments of the present invention, a system that comprises a an apparatus comprising an upper chamber and a lower chamber separated by a biocompatible membrane also includes interface electronics, including impedance measurement circuit and switches (e.g. electronic switches), to control and switch the impedance measurement circuits to different electrode structure units of the apparatuses of the present invention. Preferably, a system of the present invention also includes a computer having software programs that can enable real-time measurement or monitoring of impedance between the electrodes or electrode structures of the apparatuses of the present invention. The measured impedance data can be automatically analyzed and processed to derive appropriate parameters (e.g. cell number index, or cell migration index) and displayed on a monitor.

Preferably, the software program has one or more of the following functions: (1) electronically switching for connecting impedance measuring circuit (or analyzer) to one of multiple units of the present apparatuses; (2) controlling impedance measurement circuit (or analyzer) for measurement of impedance between or among electrodes or electrode structures at one or multiple frequencies; (3) processing the acquired impedance data to derive appropriate biologically relevant parameters (e.g., cell number index, or cell migration index); (4) displaying the results on a monitor or storing results; (5) automatically performing above functions 1 through 4 at regular or irregular time intervals.

Device (Membrane) with Multiple Electrodes or Electrode Structure Units

In some preferred embodiments of the present invention, a device for measuring the electrical impedance, resistance, or capacitance of a cell/substrate interface, comprises four or more electrodes fabricated on the same side of a biocompatible membrane that comprises at least one pore, in which at least one surface of said biocompatible membrane allows the attachment of one or more cells. The four or more electrodes are preferably arranged in an electrode array (or an electrode structure array) that comprises two or more IDESs or CCESs, each or which comprises at least two electrodes.

The device having two or more IDESs or CCESs can be preferably be part of an apparatus in which the device is reversibly or irreversibly attached to one or more structures that provide a plurality of isolated fluid containers each of which can comprise one or more IDESs or CCESs, such that the biocompatible membrane separates the fluid containers into upper chambers and lower chambers.

FIG. 16 shows an example of an apparatus that comprises multiple top chambers (1610) and bottom chambers (1630). In this case, multiple top chambers (1610) are bonded to the membrane (1620) that has pores of appropriate sizes for cell migration or invasion. Each top chamber (e.g., 1610a) has a corresponding bottom chamber (e.g., 1630a). For each top chamber, there are electrode structures on the bottom surface of the membrane, facing the bottom chamber. In operation, the electrode structures on the membrane are connected to the impedance measuring instrument via different methods. For example, electrode structures are connected via conductive traces or paths on the membrane to connection pads at the edges of the membranes. Connection pads can be connected to impedance measuring instrument through different methods. In one approach, electrical wires that are in operative connection with impedance measuring instrument or circuits can be soldered or bonded via conductive bonding to these connection pads. There are also various embodiments for the top chambers. In one embodiment, multiple top chambers may be individually separated and become connected only after they are bonded to the same membrane (1620). In another embodiment, multiple top chambers are interconnected and are manufactured together (for example, multiple top chambers are plastics and manufactured by injection molding). The one piece of these top chambers is then bonded to the membrane.

In manufacturing the biocompatible membrane, individual sensor areas can cover a larger area than will be encompasses by a well or chamber structure. This can ensure that, even in the absence of precise alignment, when an upper chamber structure and a lower chamber structure are attached to the membrane, the wells encompass a portion of the membrane that is essentially entirely sensor area.

In comprising a multi-well configuration apparatus, however, it is not required that all wells comprise electrodes or electrode structures. For example, in some preferred embodiments, one or more wells can comprise at least a portion of a biocompatible membrane that does not include electrodes or electrode structures. One or more wells that lack electrodes or electrode structures can be used as controls where the cells used in the assay can be microscopically observed, or used for biochemical assays, such as gene expression, compound detection, or viability assays that use optical detection (for example, absorbance or fluorescence) that can optionally make use of plate readers or other detection means.

In some aspects of the present invention, the electrodes are fabricated on the upper side of the membrane. In these aspects, the pores of the biocompatible membrane have a diameter of less than about 5 microns, preferably less than about 1 micron, and the upper side of the membrane preferably comprises a layer of epithelial or endothelial cells. To establish an epithelial or endothelial cell layer, epithelial or endothelial cells can be added to the top chamber, and the epithelial or endothelial cells can attach to the electrodes fabricated on the membrane, which may comprise a biomolecular coating that promotes their attachment. The attachment of epithelial or endothelial cells, which may be or may not be fully confluent on the surface of the membrane, to the electrodes fabricated on the membrane can be monitored by an impedance change measured between the electrodes. Cells that can migrate or invade into the endothelial or epithelial layer or that are suspected to have the ability to migrate or invade into the endothelial or epithelial layer are added to the top chamber. Disruption of the endothelial or epithelial layer by these cells can generate a change in impedance change that can be monitored using a system of the present invention. Optionally, one or more compounds that can affect the invasive behavior of cells can be provided in the upper or lower chambers of the apparatus. Non-limiting examples of the application of the apparatus of the present invention includes the assay of the migration/invasion properties of cancer cells and the assay of the migration properties of leukocytes.

For example, leukocyte migration across small blood vessels towards target tissue regions is a fundamental feature in inflammation. Such migration is characterized as chemotactic and is initiated and enhanced in the presence of external chemical stimuli called chemoattractants. Vigorous research efforts have been focused on understanding molecular mechanisms underlying intrinsic characteristics of migration-active leukocytes and discovering novel anti-inflammatory therapeutics with capacity to inhibit pathologic leukocyte migration. Cytokines such as IL-1, IL-6, IL-8, IL-12, IL-15, IL-18, GM-CSF, TNF-α, IFN-γ, NO, TGF-β, VIP, and somatostatin, cell adhesion molecules such as LFA-1, VLA-4, alpha chain, MAC-1, ICAM-1, VCAM-1, selectins (L, P, E), and chemokines and chemokine receptors such as: RANTES, MIP-1 MCP-1, IP-10; CCR1, CCR2B and CXCR2 can be tested for their contribution to leukocyte migration.

An in vitro assay model called leukocyte transendothelial migration, in which leukocytes migrate across an established cell monolayer in the presence of chemoattractants, has been well accepted for dissecting molecular mechanisms and for testing inhibitory chemicals or stimuli for the migration. In an example of a conventional assay of T cell migration, carotid arteries can be harvested from Lewis rats and used to isolate endothelial cells (EC) for use in the lymphocyte migration assay. EC cell line MAT-1 is established. $3-5\times10^4$ cells/ml can be applied onto 0.2% gelatin-coated cell culture inserts (polyethylene terephthalate filter, 3 um pore size, 9.0-mm diameter, 24-well format; Becton Dickinson), cultured for 1 or 2 days till confluence and stimulated with recombinant rat IFN-γ (100 U/ml, life technology). Control cells are not treated with IFN-γ. T cells ($2\times10^5$ cells/filter) are overlaid on the MAT-1 confluent layer with or without blocking antibodies and incubated in a cell culture incubator. After 3-5 h, cells that have migrated into the lower wells of the plate are harvested and counted using a microscope.

The devices of the present invention can meet the ever increasing needs for more efficient and cost-effective assay systems for analyzing leukocyte migration. The devices of the present invention allows for labeling free and real-time detection of leukocyte transendothelial migration and invasion. The proposed electronic device will keep the commonly used assay format of the filter-chamber transwell migration apparatus that contains microporous membrane inserts and lower chambers, while an array of microelectronic sensors will be built onto the microporous membrane of the insert, which allows for cell-substrate impedance measurement. The arrayed sensors will detect cells that tightly contact the electronic sensors such as a cell monolayer as well as cells that migrate across the monolayer. Therefore, besides the real-time detection of leukocyte transendothelial migration, the device will also monitor the integrity of a cell monolayer in a given insert before applying testing leukocytes, which increases the accuracy, and reproducibility of the assay. The devices, apparatuses, and systems of the present invention can be used to perform similar assays with other cell types (for example, assays of cancer cell invasiveness through ECM or cell layers).

Another examples of the application of the present invention includes the assay for determining or measuring the integrity of a cell monolayer used for drug-transportation or drug permeability testing. For this assay, Caco-2 cells have been widely used as in-vitro models to evaluate the transport of drug candidates across the intestinal epithelial barrier (for example, "The use of surfactants to enhance the permeability of peptides through Caco-2 cells by inhibition of an apically polarized efflux system", by Nerurkar M M et al, Pharm Res., Vol. 13(4):pages 528-534, 1996; "Evidence for a polarized efflux system in Caco-2 cells capable of modulating cyclosporine a transport", by Augustijins P F et al, Biochim. Biophys. Res. Comm. Vol. 197, pages 360-365, 1993; "Characterization of the human colon carcinoma cell line (Caco-2) as a model system for intestinal epithelial permeability", by Hidalgo I J, et al, Gastroenterology, Vol. 96, pages 736-749, 1989;). Typically, the assay is performed on multiple-day cultures (for examples, 10 days, 21 days) with the cells grown on a multiple-well system. Each system contains a multiple-well insert plate (or filter plate because each well in the insert plate has porous membrane on the bottom) and a multiple-well plate. The insert (or filter plate) can be placed into the multiple-well plate with individual wells on the insert plate placed into corresponding wells on the multiple-well plate. Caco-2 cells are cultured in individual wells of the filter plate for certain number of days to achieve a differentiated cell monolayer that approximates the intestinal lining. The monolayer integrity is tested by various methods, including lucifer yellow rejection method, and TEER (trans-epithelial electrical resistance). When the monolayer integrity achieves certain target parameters (for example, TEER is between 250 and 1000 Ohm $cm^2$), then the cell monolayer can then be used for testing permeability or transport ability of drug candidate molecules going through such a layer.

The apparatuses of the present invention can be used for evaluating the integrity of the cell monolayer (Caco-2 cell layer). For such an application, the electrodes are fabricated on the upper side of the membrane. In these aspects, the pores of the biocompatible membrane have a diameter of less than 10 microns, preferably less than about 3 microns, or even less than 1 microns. For example, the pore diameter can be about 1 microns, or 0.5 microns. The electrodes-containing membrane is then used to replace the microporous membrane used in the insert plate (or called filter plate) in the conventional Caco-assay system as described above. Similar to conventional Caco-2 assays, Caco-2 cells are then cultured on the membrane in the wells contained in the insert plate. Cell monolayer integrity can be monitored by measuring the impedance between the electrodes fabricated on the membrane. The higher the electrical impedance, the more confluent or more compact or more tight the cell monolayer is. Appropriate electrode impedance criteria can be established to characterize the integrity of the cell monolayer and determine when the cells are tight enough for performing compound permeability measurement.

Another examples of the application of the present invention includes a cytotoxicity assay. In this application, the apparatus is constructed in similar fashion to that used in the above Caco-2 system with one difference where the multiple-well plate into which the insert plate (or filter plate) is inserted have electrodes fabricated on the bottom of the individual wells. Thus, in this apparatus, the electrodes are fabricated on the microporous membrane that forms the bottom of the insert plate and the electrodes are also fabricated onto the bottom of the multiple-well plate. For performing the cytotoxicity assay, certain cells are cultured onto the membranes of the insert plate, similar to the Caco-2 assay described above. For example, cells that can be used for in vitro simulating the metabolic process of drug compounds in the human body can be seeded and cultured onto the membranes of the insert wells. There may be electrodes fabricated on the upper side of such membranes so that such electrodes may be used to monitor the physiological status of the cells on the membranes. On the other hand, such electrodes on the membrane may not be necessary. Other approaches may be employed to monitor the cell status such as cell monolayer integrity. When the cells on the membrane have reached certain confluence or tightness, drug compound molecules can then be added into the insert wells. These drug compound molecules will be "processed" by the cells on the membranes. Certain metabolic molecules after the drug compounds are processed by the cells on the membranes are released into the solutions and are released into the bottom well to which the insert plates are placed. For such toxicity assay, the cells (for example, cultured cells such as hepatocytes, neuron cells, lung cells, cardiomyocytes, or primary cells) to which compound toxicity or the toxicity of the compound metabolite after being processed by intestinal or other cells are cultured onto the multiple-well plate (the bottom well plate). The cell physiological status is monitored or measured by monitoring the impedance or resistance between the electrodes fabricated in the multiple-well plate. Thus, if the drug compound molecules having toxic effects or their metabolite molecules from the cells on the membrane are toxic to the cells in the bottom chamber, such compound molecules or their metabolite molecules may be transported or released into the bottom chamber. The cells in the bottom chamber can be used to measure or monitor these molecules.

In a variation of above application, the cells in the bottom wells can be specifically engineered (for example, genetically altered) for increasing their sensitivity to drug candidate molecules or the metabolic molecules from the drug candidate molecules. In such a case, the cells in the bottom wells are used for sensing and monitoring the metabolic product molecules when the drug candidate compound molecules are "processed" by the cells on the membrane. The cells in the bottom wells can be of any type of cells including neuron cells, heart cells, liver cells (hepatocytes), etc. The electrodes in the bottom wells can have geometries suitable for measuring the electrode impedance so that cell status can be monitored. The electrodes in the bottom wells can also have geometries suitable for measuring other parameters, for example for performing extracellular recording of excitable cells (for example, neuron cells, heart cells). In such a case, the extracellular recording of these excitable cells in the bottom wells is served as a sensing mechanism or method to monitor the metabolic molecules from the wells in the insert plate. The change in the extracellular-recorded signals as analysed in either time domain or frequency spectrum may be used for an indicator for the type and/or concentration of specific metabolic molecules after the drug candidate molecules are metabolized. Some examples of using excitable cells for measuring and sensing toxic or non-toxic molecules are described in "Portable cell-cased biosensor system for toxin detection", by Pancrazio, J. J., et al., Sensors and Actuators B Chemical, Vol. 53, pp. 179-185 (1998); Genetically engineered cell-based biosensors for specific agent classification, by DeBusschere B. D., et al., Proceedings of the International Solid-State Sensors and Actuators Conference-TRANSDUCERS '99, Sendai, Japan, Jun. 7-10, (1999).

In other aspects of these embodiments, the electrodes are fabricated on the lower side of the membrane. In these aspects, the pores of the biocompatible membrane have a diameter of greater than about 1 micron, and preferably less than about 30 microns, and the upper side of the membrane preferably comprises at least one substance that promotes cell adhesion on the lower side of the membrane. The upper side of the membrane can comprise at least one extracellular matrix component, and preferably comprises more than one extracellular matrix component that can form a matrix, such as, for example, Matrigel™. For example, Matrigel™ Basement Membrane Matrix (BD BioSciences) is a solubilized basement membrane preparation extracted from the Engelbreth-Holm-Swarm (REHS) mouse sarcoma, a tumor rich in extracellular matrix proteins. Its major component is laminin, followed by collagen IV, heparan sulfate proteoglycans, entactin and nidogen. It also contains TGF-beta, fibroblast growth factor, tissue plasminogen activator, and other growth factors which occur naturally in the EHS tumor.

Alternatively or in addition, the upper side of the membrane can comprise a layer of epithelial or endothelial cells. Thus, cell migration/invasion through an epithelial or endothelial cell layer can be monitored using the apparatus of the present invention. Optionally, one or more compounds that can affect the invasion/migration behavior of cells can be provided in the lower chambers of the apparatus. Optionally, one or more compounds that can affect the invasion/migration behavior of cells can be provided in the upper chambers of the apparatus.

The present invention includes apparatuses for measuring electrical impedance, resistance, or capacitance of a cell/substrate interface in which a biocompatible membrane comprising two or more electrodes is reversibly or irreversibly attached to a first plate that comprises two or more wells that provide lower chambers of cell migration units and is reversibly or irreversibly attached to a second plate that provides tube structures that provide upper chambers of cell migration units (such as a bottomless micro-well plate), such that each cell migration unit comprises a single IDES or CCES. In some aspects, the membrane can be irreversibly attached to the lower, well containing plate. In other aspects, the membrane can be irreversibly attached to the upper, tube-containing plate that forms the upper chambers. In cases in which the membrane has been irreversibly attached to the lower plate, some means for the addition of media and, optionally, other reagents or assay components to the lower chamber should be provided (for example, the lower chambers can have openings on their side walls for the addition of media).

Such apparatuses can be used to assay the migration or invasiveness of one or more cells when they are placed in an upper chamber of an apparatus. In using a device of the present invention, a device will be part of, attached to, or within a plate or a fluid-container that can contain cells and media, such that, in the presence of an appropriate medium for cells, the attachment or detachment of one or more cells on the side of the membrane on which said at least two electrodes are fabricated can be detected by a change in impedance, capacitance, or resistance using the device.

The present invention also includes systems for measuring electrical impedance, resistance, or capacitance of a cell/substrate interface comprising the apparatuses described herein that comprise a membrane having multiple electrode structures surrounded by multiple fluid containers and an impedance analyzer that can be connected to the multiple electrodes. Preferably, an impedance analyzer (or impedance measurement circuit) is also, operatively, connected to the electrodes. The impedance can be analyzed or measured in any suitable frequency range, e.g., a frequency range between about 1 Hz and about 100 MHz, or between 10 Hz and about 5 MHz. The connection of an impedance analyzer to electrodes of an apparatus can be direct or indirect. For example, electrodes can extend to a connection pad and connect with an impedance analyzer at the connection pads. In another example, electrodes or electrode elements can connect to a connection pad via a electrically conductive connection path.

In preferred embodiments of the present invention, a system that comprises a device of the present invention also includes interface electronics, including impedance measurement circuit and switches (e.g. electronic switches), to control and switch the impedance measurement circuits to different electrode structure units of the apparatuses of the present invention. Preferably, a system of the present invention also includes a computer having software programs that can enable real-time measurement or monitoring of impedance between the electrodes or electrode structures of the apparatuses of the present invention. The measured impedance data can be automatically analyzed and processed to derive appropriate parameters (e.g. cell number index, or cell migration index) and displayed on a monitor.

Preferably, the software program has one or more of the following functions: (1) electronically switching for connecting impedance measuring circuit (or analyzer) to one of multiple units of the present apparatuses; (2) controlling impedance measurement circuit (or analyzer) for measurement of impedance between or among electrodes or electrode structures at one or multiple frequencies; (3) processing the acquired impedance data to derive appropriate biologically relevant parameters (e.g., cell number index, or cell migration index); (4) displaying the results on a monitor or storing results; (5) automatically performing above functions 1 through 4 at regular or irregular time intervals.

Multiplex Two Chamber Systems with Separate Membranes

The present invention also includes apparatuses for measuring electrical impedance, resistance, or capacitance of a cell/substrate interface, comprising a plate that comprises two or more wells, each of which comprises a membrane that comprises at least two electrodes and one or more pores, where the membrane separates a well into upper and lower chambers, and the membrane comprises a surface suitable for cell attachment and growth.

Such apparatuses can be used to assay the migration or invasiveness of one or more cells when they are placed in an upper chamber of an apparatus. In using an apparatus of the present invention, the attachment or detachment of one or more cells on the side of the membrane on which said at least two electrodes are fabricated due to migratory or invasive behavior of at least a portion of the cells introduced into the upper chamber can be detected by a change in impedance, capacitance, or resistance.

The apparatus of the present invention can be manufactured by any appropriate means. For example, membranes having pores and on which one or more electrodes have been fabricated can be attached to bottomless well structures to form top chambers that can subsequently be attached to a structure comprising wells that can form bottom chambers. Alternatively, devices can be first attached to a structure comprising wells that can form bottom chambers, and subsequently the top piece comprising tube-like structures (bottomless wells) can be attached to form top chambers. In cases in which the lower plate is irreversibly attached to the membrane, and the membrane covers the entire upper surface or the bottom chamber, some means (for example, holes in the side walls of the lower chambers) should be provided for introducing media and optionally other reagents into the lower chambers. This can be done if the medium has already been added into the bottom chamber) An alternative strategy is to pattern electrodes and form pores on the bottom surfaces of wells of a multi-well plate (such as, for example, a multi-well plate having thin polycarbonate membrane as the bottom), and subsequently attach a bottom structure having wells that can form bottom chambers.

The pores and electrodes can be fabricated on a membrane by any suitable means, depending on the material of the membrane and electrodes. Tne methods used for fabricating pores and the electrodes may also depend on the procedures used to form top and bottom chambers. For example, pores can be made by ion bombardment followed by etching, or by laser drilling. Fabrication of electrodes on substrates has been described above, and for fabrication on the bottom surface of a well can include such techniques as laser patterning (or laser ablation). Electrodes can be fabricated on a membrane before pores are made in the membrane, or alternatively, pores can be made in a membrane and then electrodes can be fabricated on the surface. Location of the electrodes and pores on the membrane may have a corresponding relationship, i.e. the pores are located on the regions that correspond to the electrode surfaces.

The present invention also includes systems for measuring electrical impedance, resistance, or capacitance of a cell/substrate interface comprising the apparatuses described herein that comprises a plate that comprises multiple wells, each of which comprises a biocompatible microporous membrane that comprises at least two electrodes and one or more pores, and an impedance analyzer that can be connected to the multiple electrodes. Preferably, an impedance analyzer (or impedance measurement circuit) is also, operatively, connected to the electrodes. The impedance can be analyzed or measured in any suitable frequency range, e.g., a frequency range between about 1 Hz and about 100 MHz, or between 10 Hz and about 5 MHz. The connection of an impedance analyzer to electrodes of an apparatus can be direct or indirect. For example, electrodes can extend to a connection pad and connect with an impedance analyzer at the connection pads. In another example, electrodes or electrode elements can connect to a connection pad via an electrically conductive connection path.

In preferred embodiments of the present invention, a system that comprises a multi-well plate apparatus of the present invention also includes interface electronics, including impedance measurement circuit and switches (e.g. electronic switches), to control and switch the impedance measurement circuits to different electrode structure units of the apparatuses of the present invention. Preferably, a system of the present invention also includes a computer having software programs that can enable real-time measurement or monitoring of impedance between the electrodes or electrode structures of the apparatuses of the present invention. The measured impedance data can be automatically analyzed and processed to derive appropriate parameters (e.g. cell number index, or cell migration index) and displayed on a monitor.

Preferably, the software program has one or more of the following functions: (1) electronically switching for connecting impedance measuring circuit (or analyzer) to one of multiple units of the present apparatuses; (2) controlling impedance measurement circuit (or analyzer) for measurement of impedance between or among electrodes or electrode structures at one or multiple frequencies; (3) processing the acquired impedance data to derive appropriate biologically relevant parameters (e.g., cell number index, or cell migration index); (4) displaying the results on a monitor or storing results; (5) automatically performing above functions 1 through 4 at regular or irregular time intervals.

Multiplex Insert Tray Systems

The present invention also comprises apparatuses for measuring electrical impedance, resistance, or capacitance of a cell/substrate interface, comprising an inert tray that comprises one or more insert chambers, each of which comprises fluid impermeable walls and a porous biocompatible membrane comprising two or more electrodes forming the bottom of at least one, of the one or more insert chambers. Preferably the apparatus also includes a plate that comprises one or more wells, such that an insert tray of the present invention fits the plate. Preferably, the insert tray comprises multiple insert chambers and a corresponding plate comprises multiple wells, and the insert tray is designed such that the insert chambers align with and fit into the wells of a plate. Each insert chamber fits preferably into a well of a plate such that the wells of the plate form lower chambers and the inserts of an insert tray form upper chambers of a cell invasion/migration unit.

The present invention includes apparatuses for measuring electrical impedance, resistance, or capacitance of a cell/substrate interface in which an insert tray comprising biocompatible membranes forming the bottoms of upper chambers is reversibly fitted to a first plate that comprises two or more wells that provide lower chambers of cell migration units, such that each cell migration unit preferably comprises an IDES or CCES unit.

Such apparatuses can be used to assay the migration or invasiveness of one or more cells when they are placed in an upper chamber (insert chamber) of an apparatus such that, in the presence of an appropriate medium for cells, the attachment or detachment of one or more cells on the side of the membrane on which said at least two electrodes are fabricated can be detected by a change in impedance, capacitance, or resistance using the device.

The present invention also includes systems for measuring electrical impedance, resistance, or capacitance of a cell/substrate interface comprising the insert tray and multi-well plate apparatus, and further comprising an impedance analyzer that can be connected to the multiple electrodes of the membrane insert. Preferably, an impedance analyzer (or impedance measurement circuit) is also, operatively, connected to the electrodes. The impedance can be analyzed or measured in any suitable frequency range, e.g., a frequency range between about 1 Hz and about 100 MHz, or between 10 Hz and about 5 MHz. The connection of an impedance analyzer to electrodes of an apparatus can be through connection pads located on the insert tray.

Figure 17:
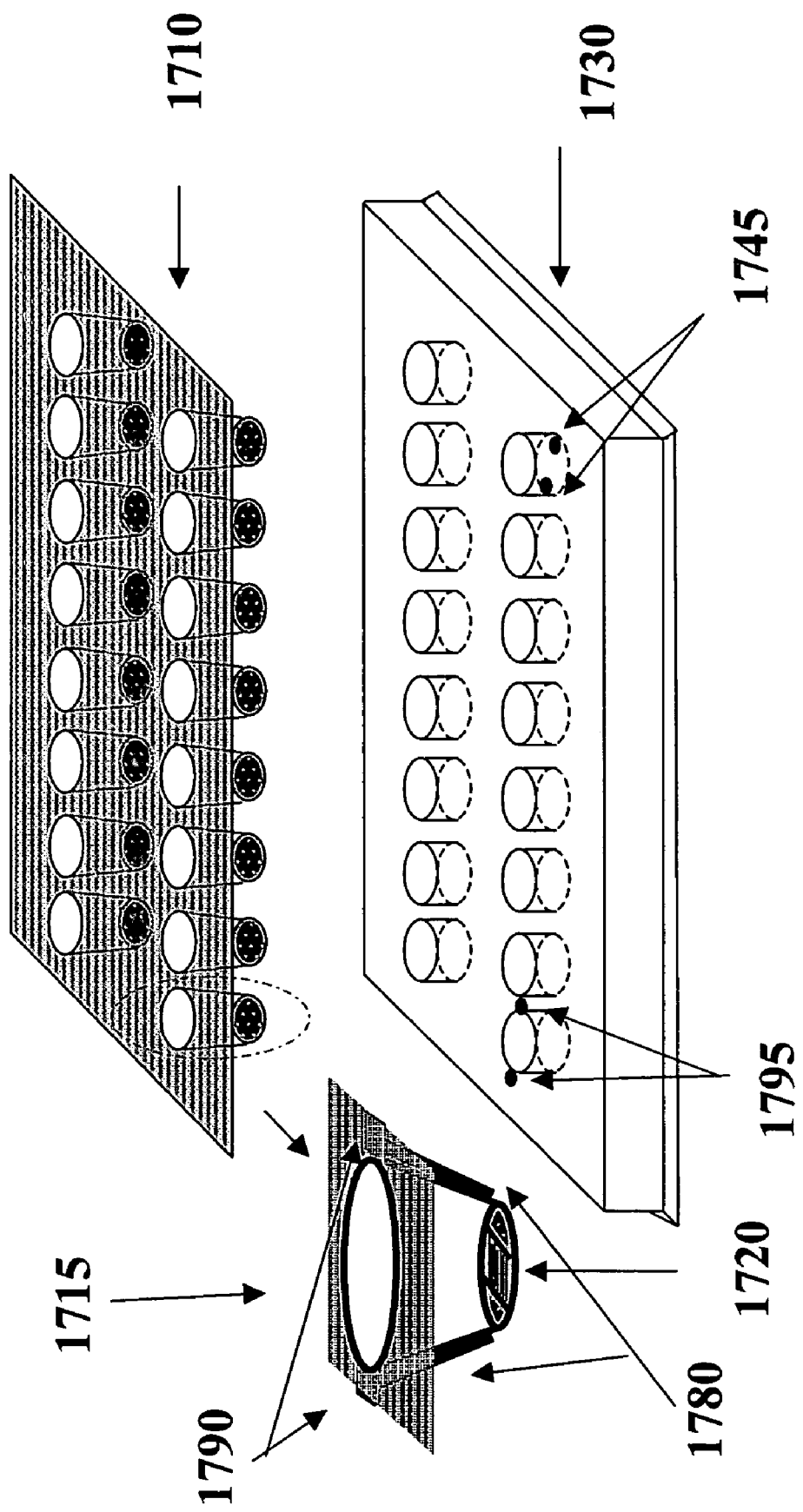
FIG. 17 is a schematic representation of an apparatus that comprises multiple sites for cell migration and invasion measurements. A bottom plate (1730) comprises multiple bottom chambers. A top plate (1710) comprises multiple insert wells (1715). The bottom surface of each insert well is a membrane (1720) that has electrode structures on the bottom surface, facing the bottom chamber. In operation, the top plate (1710) is placed into the bottom plate (1730). The electrode structures on the bottom surface of each insert well are connected to the impedance measuring instruments via various methods. For example, electrode structures on the bottom surface of the membrane can be connected to connection points (1790) located on the outer edges of the inert wells through electrically-conductive paths (1780) located along the outside of the insert wells. The connection points (1790) may further be connected to connection pads (1795) located on the bottom plate when the inserts wells are inserted into the bottom plate. The connection pads (1795) located on the bottom plate may be operatively connected to the impedance measuring circuits. In another example, electrode structures on the bottom surface of the membrane can be connected to connection pads (not shown) located on the membrane. When the insert wells are inserted into the bottom plate, such connection pads can be contact-connected to needle-shaped or other shaped connection points (1750) located in the bottom chambers.
Figure 18:
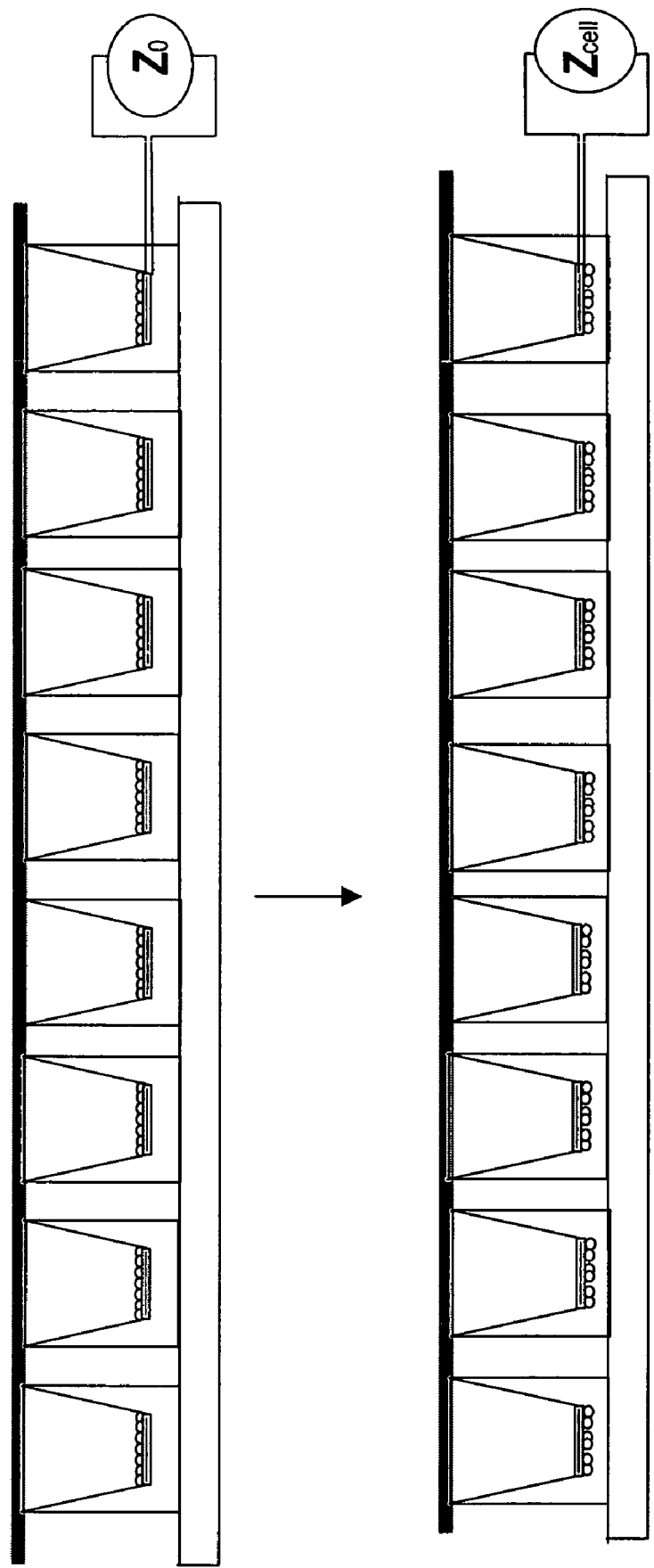
FIG. 18 is a cross-sectional view of cell migration/invasion apparatuses of FIG. 17, illustrating the impedance measurement of the electrode structures located on the membrane of each insert well prior to cell migration through pores on the membrane (top panel, impedance is $Z_O$) and after cell invasion/migrayion through pores on the membrane (bottom panel, impedance is $Z_{cell}$).

FIG. 17 shows a schematic representation of an exemplary embodiment of the apparatus that comprises an insert tray (top plate 1710) and a multi-well bottom plate (1730). The bottom plate (1730) comprises multiple bottom chambers. The top plate (1710) comprises multiple insert wells (1715). The bottom surface of each insert well is a membrane (1720) that has electrode structures on the bottom surface, facing the bottom chamber. In operation, the top plate (1710) is placed into the bottom plate (1730). The electrode structures on the bottom surface of each insert well are connected to the impedance measuring instruments via various methods. For example, electrode structures on the bottom surface of the membrane can be connected to connection points (1790) located on the outer edges of the inert wells through electrically-conductive paths (1780) located along the outside of the insert wells. The connection points (1790) may further be connected to connection pads (1795) located on the bottom plate when the inserts wells are inserted into the bottom plate. The connection pads (1795) located on the bottom plate may be operatively connected to the impedance measuring circuits. In another example, electrode structures on the bottom surface of the membrane can be connected to connection pads (not shown) located on the membrane. When the insert wells are inserted into the bottom plate, such connection pads can be contact-connected to needle-shaped or other shaped connection points (1750) located in the bottom chambers.

In preferred embodiments of the present invention, a system that comprises an insert tray and multi-well plate apparatus of the present invention also includes interface electronics, including impedance measurement circuit and switches (e.g. electronic switches), to control and switch the impedance measurement circuits to different electrode structure units of the apparatuses of the present invention.

The present invention also includes methods for monitoring cell migration or invasion, comprising providing an apparatus as described above for cell migration or invasion, placing cells in the upper chamber of said apparatus; and monitoring a change of impedance between or among the electrodes to monitor migration or invasion of the cells.

In use, the present invention is directed to a method for monitoring cell migration or invasion, which method comprises: a) providing an above-described apparatus for monitoring cell migration or invasion; b) placing migrating or invasive cells or cells suspected of being migrating or invasive on the upper chamber for the apparatus and allowing the cells to move from the upper chamber into the lower chamber via the pores of the polymer membrane; and c) monitoring a change of impedance between or among the electrodes to monitor migration or invasion of the cells.

The method of the invention can be used to monitor any suitable parameters that are related to cell migration or invasion. For example, the method can be used to monitor the amount or number of cells that migrate or invade into the lower chamber based on the monitored impedance.

The present methods can be used to determine weather a test compound can modulate, i.e., increase or decrease, migration or invasion, or to screen for such a modulator. For example, the present methods can be conducted wherein the cell migration is monitored in the presence and absence of a test compound and the method is used to determine whether the test compound modulates migration or invasion of the cells. In another example, the present methods can be conducted wherein the cell migration or invasion is stimulated by a migration or invasion stimulator and the method is used to screen the test compound for an antagonist of the stimulator.

The methods can also be used to monitor migration or invasion of normal cells. Alternatively, the present methods can be used to monitor migration or invasion of abnormal cells, e.g., metastasis of tumor or cancer cells. In a specific embodiment, the present methods can be used to monitor migration or invasion of tumor cells, endothelial cells, epithelia cells, fibroblasts, myoblasts, neurons and gliacytes, etc.

The following illustrates an example of the present apparatus and its operation. The apparatus for monitoring cell migration/invasion comprises an upper chamber or an insert and a bottom chamber or a lower well, separated by a polymer membrane, e.g. a microporous PET (polyethylene terephthalate) membrane. The polymer membrane comprises multiple pores that are of appropriate sizes permitting the invasive cells to go through. The bottom chamber or the lower well supports a microelectrode array having at least two sets of electrode elements (i.e., two electrode arrays). The electrode array is of appropriate geometry so that when cells are introduced and attached to the electrode plane, impedance between the electrode arrays will be altered. Examples of the electrode arrays include an inter-digitized, parallel electrode array, a two-parallel-spiral electrode array and a circular electrode array. The apparatus for monitoring cell migration/invasion may further comprise an impedance analyzer that is capable of determining the impedance between two sets of microelectrodes.

In operation, cells to be analyzed are introduced into a top chamber. Appropriate reagents (e.g. cell migration/invasion modulators that stimulate or inhibit cell migration/invasion or reagents suspected to be cell migration/invasion modulators) may be added into the top chamber during or after the cell addition to the top chamber. The bottom chamber is loaded with appropriate buffer or a cell culture medium. The buffer or medium loaded into the bottom, chamber may comprise suitable reagents, e.g., chemoattractants or other cell migration modulators that may stimulate or inhibit cell migration or reagents suspected of being cell migration/invasion modulators. When the cells from the top chamber penetrate through the holes of the trans-chamber membrane and reach the bottom chamber, landing on and attaching to the electrode structures located on the bottom chamber, the altered impedance between the electrodes is measured and analyzed. Preferably, electrode regions (i.e. sensor areas) cover the majority of the surface area of the bottom surface of the bottom chamber. Preferably, the surface area of the bottom well is somewhat reduced so that there is an improved sensitivity. To cover a wide dynamic range, it is possible to have multiple, different sized-bottom chamber as a series so that each area range covers a range of cell numbers, e.g., 1-10, 10-100, 100-1000, 1000-10000, etc.

The following illustrates another example of the present apparatus and its operation. The apparatus comprises an upper chamber and a bottom chamber, separated by a polymer membrane e.g. a microporous PET (polyethylene terephthalate) membrane. The polymer membrane comprises multiple pores that are of appropriate sizes permitting the invasive cells to go through. The size and the number of the pores in the polymer membrane have to be carefully controlled for corresponding to different cell numbers and different cell sizes. One electrode is on the top chamber and another electrode is on the bottom chamber. When the cells invade and go through the pores in the membranes separating two chambers, the electrical impedance between the two electrodes will be altered. Electrodes that can monitor the trans-membrane impedance are used to provide the information for migration process.

Impedance Frequency Spectrum for Cell Assays

Figure 25A:
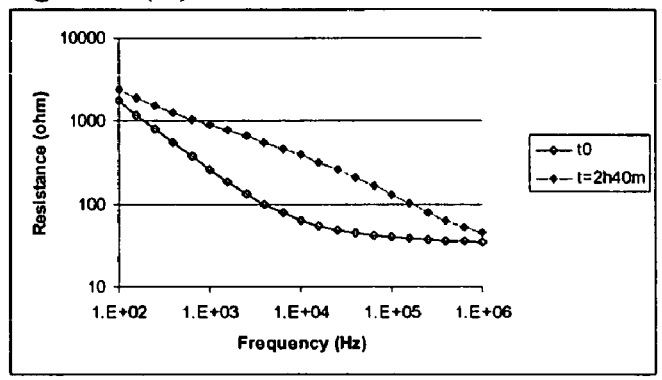
FIG. 25(A) shows typical frequency spectra of measured resistance for circle-on-line electrode structures fabricated on glass substrates under two conditions: (a), open symbol, shortly after (within 10 minutes, cells had not attached yet to the electrode and substrate surfaces) the tissue culture medium containing HT1080 cells was added to a well containing the electrode structure; (b) solid symbol, 2 h 40 minutes (cells were attached to the electrode and substrate surfaces) after the culture medium containing HT1080 cells were added to the wells containing the electrode structures on the well bottom surface. During the 2 h 40 minutes period, the well was placed into a tissue culture incubator that was set at 37° C. and 5% $CO_2$ level. The electrode structure is of 3B design where the line width is 30 micron, the gap between lines is 80 micron and the continuous circles on the lines have 90 micron in diameter. In this example, the total area covered the electrodes and the gaps between the electrodes correspond to a circle of 3 mm in diameter. The electrode structure on the glass substrate forms a bottom of a conical shaped well where the top diameter of the well is about 6.5 mm in diameter whereas the bottom diameter is about 5 mm. For the experiment, total 100 microliter volume of the tissue culture medium containing about 7000 HT 1080 cells was added to the wells comprising the electrode structure on the bottom of the well.

FIG. 25(A) shows typical frequency spectra of measured resistance for circle-on-line electrode structures fabricated on glass substrates under two conditions: (a), open symbol, shortly after (within 10 minutes, cells had not attached yet to the electrode and substrate surfaces) the tissue culture medium containing HT 1080 cells was added to a well containing the electrode structure; (b) solid symbol, 2 h 40 minutes (cells were attached to the electrode and substrate surfaces) after the culture medium containing HT1080 cells were added to the wells containing the electrode structures on the well bottom surface. Shortly after (within 10 minutes) cell-containing medium was added the well, the cells did not have enough time to attach to the electrodes. This was confirmed by that the measured impedance (resistance and reactance) for the electrode structure with the cell-containing medium was the same, or almost the same, as that obtained for the cell-free medium added to the well. For the condition when the cell-free culture medium was introduced over the electrodes, or when the cell-containing medium was introduced over the electrodes but the cells did not have enough time to attach to the electrode structures, typically, the high frequency (e.g., around 1 MHz and above) impedance (resistance and reactance) is mainly determined by the electrode geometry and electrical property of the medium (electrical conductivity and dielectric permittivity) of the solution that is introduced over the electrode structure. At lower frequencies, there exists a so-called "electrode polarization" effect, leading to the frequency dependent resistance and capacitance ((see, for example, Schwan, H. P., "Linear and nonlinear electrode polarization and biological materials", in Ann. Biomed. Eng., Vol. 20, pp 269-288, 1992; Jaron, D., Schwan, H P and Geselowitz., "A mathematical model for the polarization impedance of cardiac pacemaker electrodes", in Med. Biol. Eng., Vol. 6, pp 579-594). For the condition of 2 h 40 minutes after the cell-containing medium was introduced to the well which was placed into a tissue culture incubator for over 2 h 40 minutes, the cells were given enough time to attach and spread (as confirmed by microscope examination of the cells in the region not covered by the electrodes). Because of the non-conducting nature of the cell membrane, the frequency spectrum of the resistance of the electrode structures was altered. Typically, there was an increase in the inter-mediate frequencies (1 kHz to 100 kHz). There was small change in either lower or higher frequency regions.

Figure 25B:
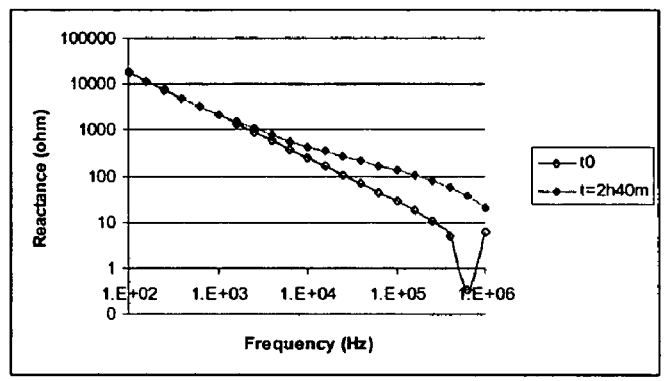
FIG. 25(B) shows a frequency spectrum of measured reactance for the same electrode structures under two same conditions as in FIG. 25(A). Note that the absolute magnitude of the reactance was plotted in log scale (in the same way as the curves in FIG. 16). Except for high frequencies of 1 MHz and about 580 kHz, the reactance was negative (capacitance reactance) for the electrode structures measured shortly after (within 10 minutes) the tissue culture medium containing HT1080 cells was added to the well containing the electrode structures. For the reactance measured at 2 h 40 minutes after cell suspension was added into the well containing the electrode structures, the reactance was negative throughout the frequency range measured between 100 Hz and 1 MHz.

FIG. 25(B) shows a frequency spectrum of measured reactance for the same electrode structures under two same conditions as in FIG. 25(A): (a), open symbol, shortly after (within 10 minutes, cells had not attached yet to the electrode and substrate surfaces) the tissue culture medium containing HT1080 cells was added to a well containing the electrode structure; (b) solid symbol, 2 h 40 minutes (cells were attached to the electrode and substrate surfaces) after the culture medium containing HT1080 cells were added to the wells containing the electrode structures on the well bottom surface. Shortly after (e.g., within 10 minutes) cell-containing medium was added the well, the cells did not have enough time to attach to the electrodes. This was confirmed by that the measured impedance (resistance and reactance) for the electrode structure with the cell-containing medium was the same, or almost the same, as that obtained for the cell-free medium added to the well. As described above, for the condition when the cell-free culture medium was introduced over the electrodes, or when the cell-containing medium was introduced over the electrodes but the cells did not have enough time to attach to the electrode structures typically, the high frequency (e.g., around 1 MHz and above) resistance is mainly determined by the electrode geometry and electrical conductivity of the solution that is introduced over the electrode structure. At lower frequencies, there exists a so-called "electrode polarization" effect, leading to the frequency dependent resistance and capacitance (see, for example, Schwan, H. P., "Linear and nonlinear electrode polarization and biological materials", in Ann. Biomed. Eng., Vol. 20, pp 269-288, 1992; Jaron, D., Schwan, H P and Geselowitz., "A mathematical model for the polarization impedance of cardiac pacemaker electrodes", in Med. Biol. Eng., Vol. 6, pp 579-594). For the condition of 2 h 40 minutes after the cell-containing medium was introduced to the well, which was placed in a tissue culture incubator for 2 h 40 minutes, the cells were given enough time to attach and spread (as confirmed by microscope examination of the cells in the region not covered by the electrodes). Under such a condition, because of the non-conducting nature of the cell membrane, the frequency spectrum of the reactance of the electrode structures was altered. Different from the change in the resistance, the major relative change occurred in the higher frequencies where the overall magnitude of the reactance was also increased significantly because of the cells attached onto the electrodes.

Figure 25C:
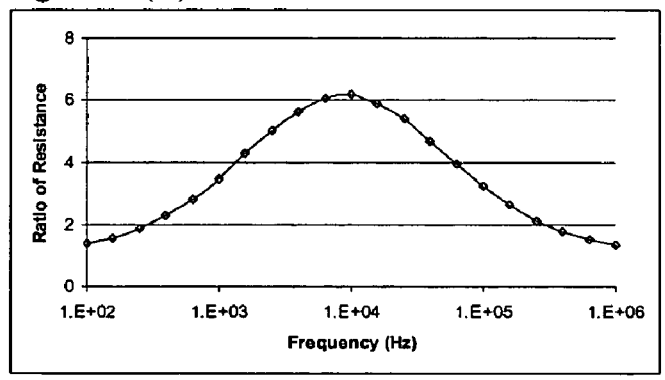
FIG. 25(C) shows the frequency spectrum of the ratio of resistance measured with cell-attached onto the electrode surfaces to the resistance measured without cells-attached for the results illustrated in FIG. 25(A).
Figure 25D:
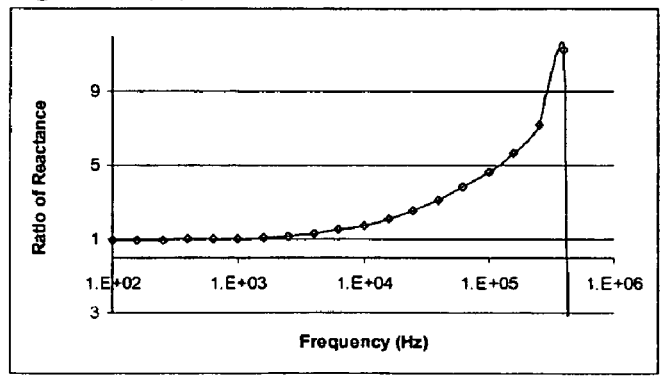
FIG. 25(D) shows the frequency spectrum of the ratio of reactance measured with cell-attached onto the electrode surfaces to the resistance measured without cells-attached for the results illustrated in FIG. 25(A). Note that for this calculation of reactance ratio, the polarity of the reactance (i.e., capacitance and inductive reactance) was taken into account.
Figure 26A:
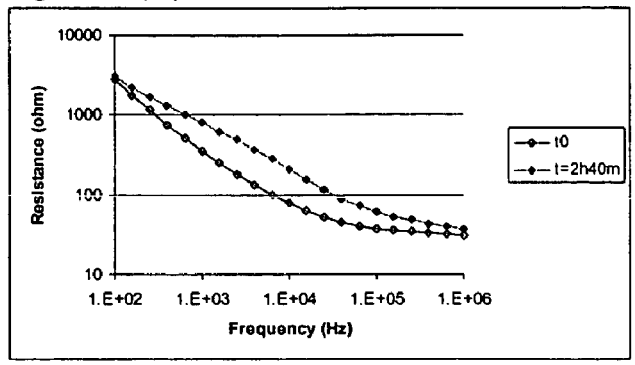
FIG. 26(A) shows typical frequency spectra of measured resistance for circle-on-line electrode structures fabricated on glass substrates under two conditions: (a), open symbol, shortly after (within 10 minutes, cells had not attached yet to the electrode and substrate surfaces) the tissue culture medium containing HT1080 cells was added to a well containing the electrode structure; (b) solid symbol, 2 h 40 minutes (cells were attached to the electrode and substrate surfaces) after the culture medium containing HT1080 cells were added to the wells containing the electrode structures on the well bottom surface. During the 2 h 40 minutes period, the well was placed into a tissue culture incubator that was set at 37° C. and 5% $CO_2$ level. The electrode structure is of 3B design where the line width is 30 micron, the gap between lines is 80 micron and the continuous circles on the lines have 90 micron in diameter. In this example, the total area covered the electrodes and the gaps between the electrodes correspond to a circle of 3 mm in diameter. The electrode structure on the glass substrate forms a bottom of a conical shaped well where the top diameter of the well is about 6.5 mm in diameter whereas the bottom diameter is about 5 mm. For the experiment, total 100 microliter volume of the tissue culture medium containing about 3200 HT 1080 cells was added to the wells comprising the electrode structure on the bottom of the well.
Figure 26B:
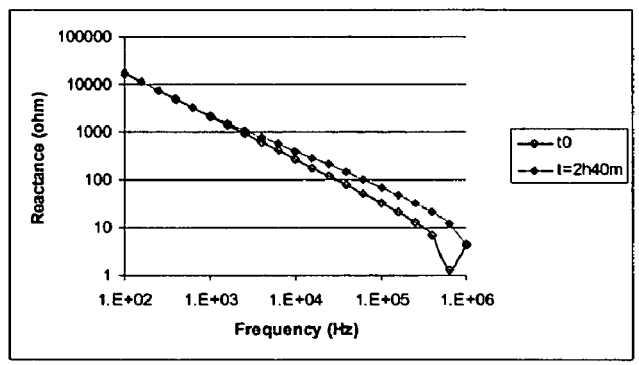
FIG. 26(B) shows a frequency spectrum of measured reactance for the same electrode structures under two same conditions as in FIG. 26(A). Note that the absolute magnitude of the reactance was plotted in log scale (in the same way as the curves in FIG. 16). Except for high frequencies of 1 MHz and about 580 kHz, the reactance was negative (capacitance reactance) for the electrode structures measured shortly after (within 10 minutes) the tissue culture medium containing HT1080 cells was added to the well containing the electrode structures. For the reactance measured at 2 h 40 minutes after cell suspension was added into the well containing the electrode structures, the reactance was negative throughout the frequency range measured between 100 Hz and 1 MHz.
Figure 26C:
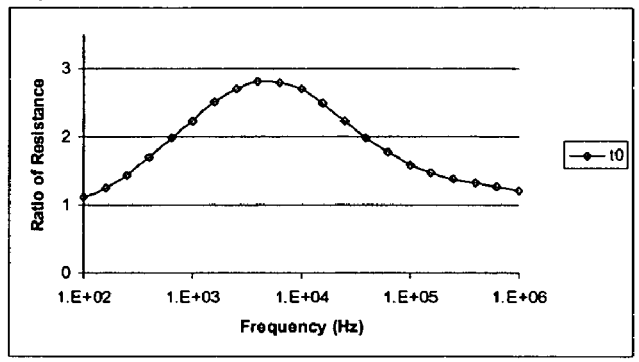
FIG. 26(C) shows the frequency spectrum of the ratio of resistance measured with cell-attached onto the electrode surfaces to the resistance measured without cells-attached for the results illustrated in FIG. 26(A).
Figure 26D:
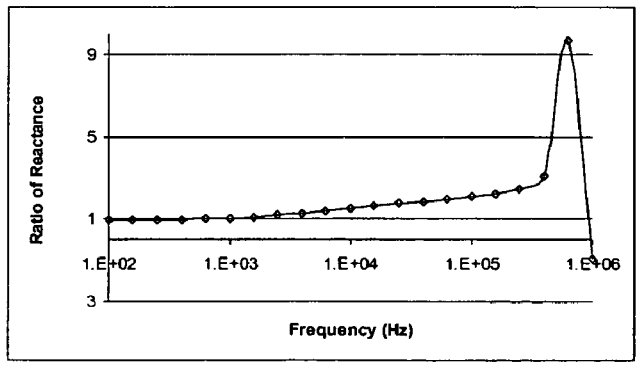
FIG. 26(D) shows The frequency spectrum of the ratio of reactance measured with cell-attached onto the electrode surfaces to the resistance measured without cells-attached for the results illustrated in FIG. 26(A). Note that for this calculation of reactance ratio, the polarity of the reactance (i.e., capacitance and inductive reactance) was taken into account.

If we take the ratio of resistance measured with cell-attached to the resistance measured without cells-attached and plot this ratio (namely, relative change in resistance or serial resistance) as a function of the frequency, typically, we observe a peak-shaped curve (FIG. 25(C)). At lower frequency, there is small or no change in the impedance (in this case, the serial resistance), the ratio is approximately one. With increasing frequency, this ratio increases until it reaches a peak-value. With increasing the frequency further, the ratio decreases to about one at high frequencies. It should be pointed out that it is also possible to plot a relative change in the reactance or capacitance value and use the change in the reactance to monitor and reflect the cell attachment to the electrode surfaces (see FIG. 25(D)). Furthermore, expression of impedance in terms of parallel resistance and reactance can also be used for describing the change in impedance due to cell attachment to the electrode surfaces.

The peak value of the resistance ratio (i.e., the ratio of the resistance with cell-attached to the electrodes to the resistance when no-cell-attached to the electrodes) and the frequency at which the peak value occurs depend on, among other things, how many cells attached on the electrode surface, how tight such attachment is, the size of the cells, what dielectric properties the cells have for their plasma membrane and intracellular components. For a number of the cell types we have tested, we found that more cells attached to the electrode surface result in higher peak value for the ratio and the higher frequency value at which the peak occurs, for the cells of the same type and under similar physiological conditions (e.g. in exponential growth phase).

Figure 27A:
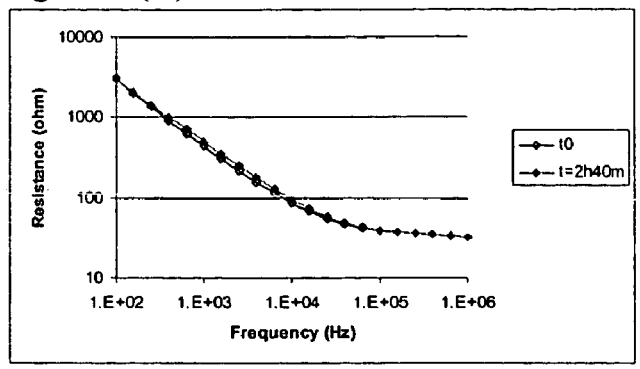
FIG. 27(A) shows typical frequency spectra of measured resistance for circle-on-line electrode structures fabricated on glass substrates under two conditions: (a), open symbol, shortly after (within 10 minutes, cells had not attached yet to the electrode and substrate surfaces) the tissue culture medium containing HT1080 cells was added to a well containing the electrode structure; (b) solid symbol, 2 h 40 minutes (cells were attached to the electrode and substrate surfaces) after the culture medium containing HT 1080 cells were added to the wells containing the electrode structures on the well bottom surface. During the 2 h 40 minutes period, the well was placed into a tissue culture incubator that was set at 37° C. and 5% $CO_2$ level. The electrode structure is of 3B design where the line width is 30 micron, the gap between lines is 80 micron and the continuous circles on the lines have 90 micron in diameter. In this example, the total area covered the electrodes and the gaps between the electrodes correspond to a circle of 3 mm in diameter. The electrode structure on the glass substrate forms a bottom of a conical shaped well where the top diameter of the well is about 6.5 mm in diameter whereas the bottom diameter is about 5 mm. For the experiment, total 100 microliter volume of the tissue culture medium containing about 500 HT 1080 cells was added to the wells comprising the electrode structure on the bottom of the well.
Figure 27B:
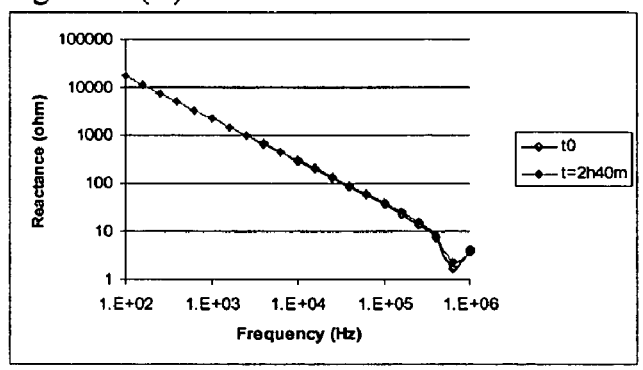
FIG. 27(B) shows a frequency spectrum of measured reactance for the same electrode structures under two same conditions as in FIG. 27(A). Note that the absolute magnitude of the reactance was plotted in log scale (in the same way as the curves in FIG. 16). Except for high frequencies of 1 MHz and about 580 kHz, the reactance was negative (capacitance reactance) for the electrode structures measured under both conditions.
Figure 27C:
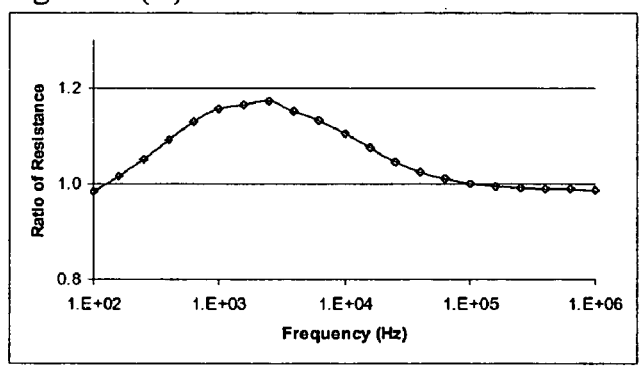
FIG. 27(C) shows the frequency spectrum of the ratio of resistance measured with cell-attached onto the electrode surfaces to the resistance measured without cells-attached for the results illustrated in FIG. 27(A).
Figure 27D:
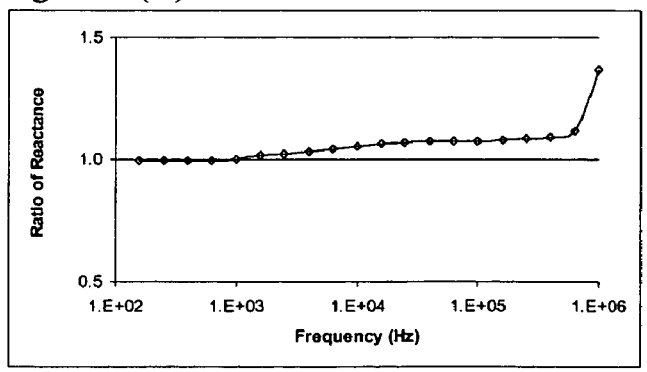
FIG. 27(D) shows The frequency spectrum of the ratio of reactance measured with cell-attached onto the electrode surfaces to the resistance measured without cells-attached for the results illustrated in FIG. 25(A). Note that for this calculation of reactance ratio, the polarity of the reactance (i.e., capacitance and inductive reactance) was taken into account.

In comparison with the results in FIGS. 25(A), 25(B) and 25(C), FIG. 26(A), 26(B), 26(C) shows the frequency spectra of the resistance, reactance and resistance ratio for a similar circle-on-line electrode with more cells applied to the wells comprising the circle-on-line electrode structures on the bottom well, FIGS. 27(A), 27(B), 27(C) shows the results for less-number of cells attached to the electrodes.

Figure 28A:
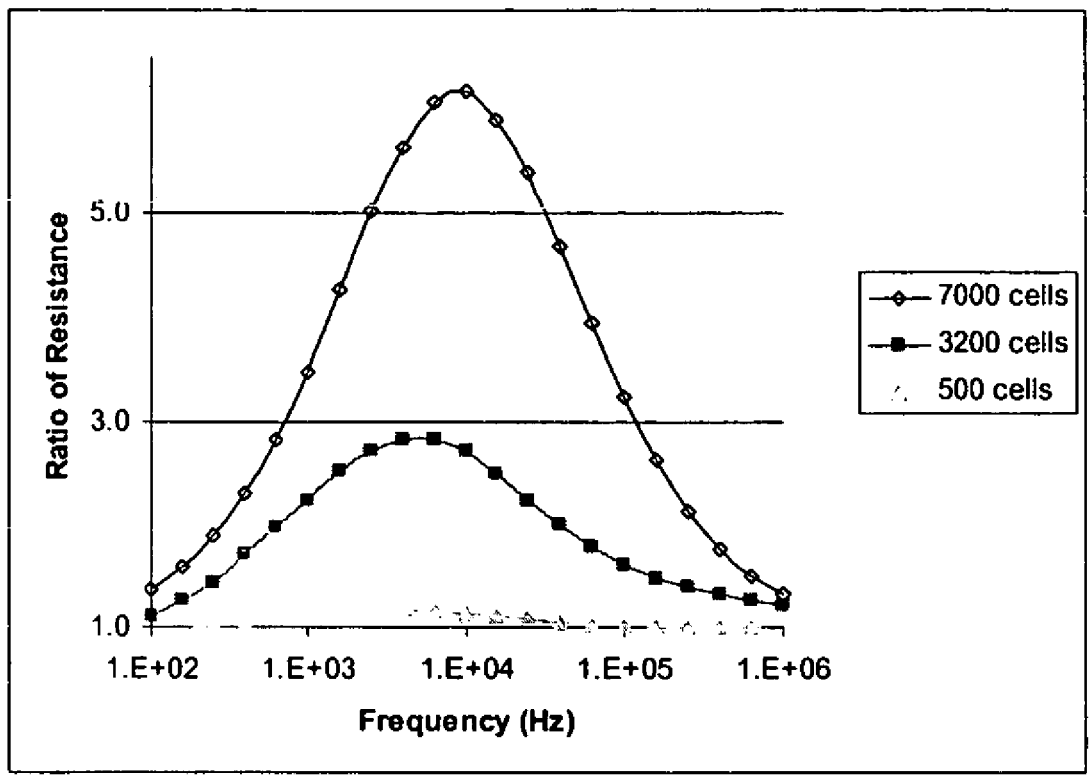
FIG. 28(A) shows the frequency spectra of resistance-ratio for different numbers of cells added into the wells comprising the same types of circle-on-line electrode structures (electrode geometry 3B).
Figure 28B:
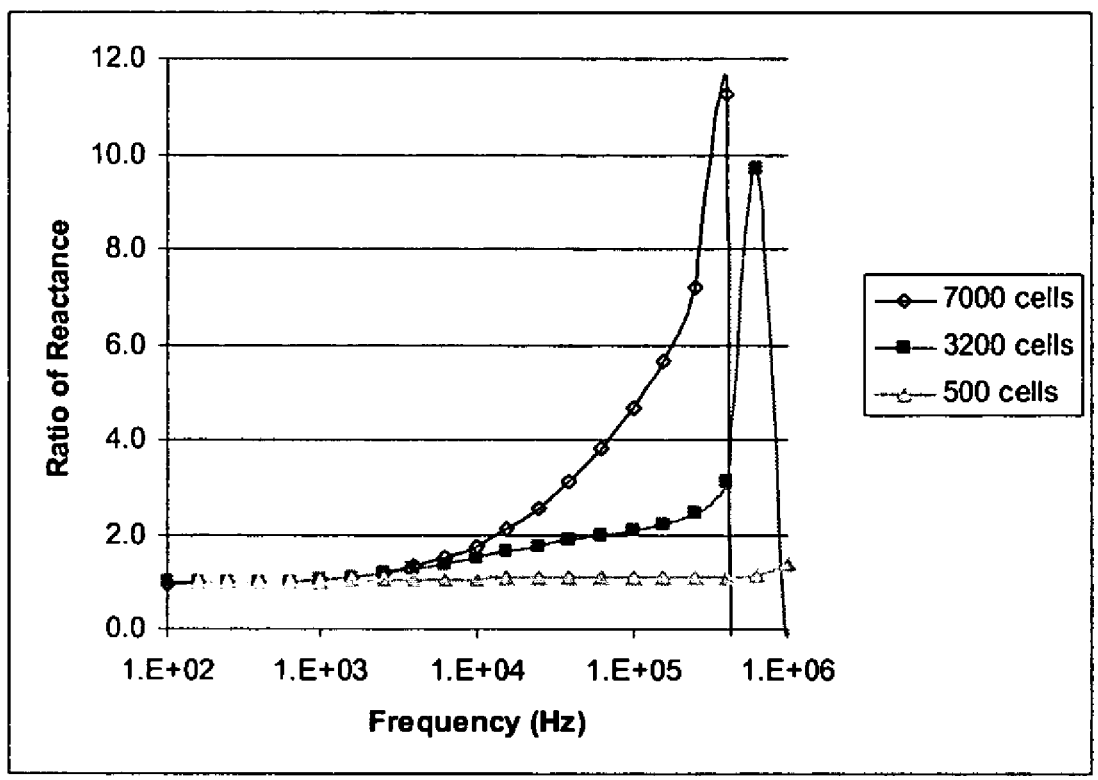
FIG. 28(B) shows the frequency spectra of reactance-ratio for different numbers of cells added into the wells comprising the same types of circle-on-line electrodes (electrode geometry 3B).

FIG. 28A shows the frequency spectra of resistance-ratio for different numbers of cells added into the wells comprising the same types of circle-on-line electrodes. For example, seeding about 500 cells results a maximum of 17% change in the serial resistance occurring at ~2 kHz, whilst seeding 3200 and 7000 cells resulted 182% and 517% change in serial resistance occurring at ~5 and 30 kHz, respectively. Again, the change in the serial reactance can also be used for demonstrating such relationship between the cell number and the magnitude of the change in reactance (see FIG. 28B, for example, the reactance values at 250 kHz may be used to illustrate relationship between the cell number and the magnitude of the change in reactance). Furthermore, if parallel resistance and parallel reactance are used to express the measured impedance, it is also possible demonstrate the dependent relationship between the cell number and the magnitude of the changes in parallel resistance and/or parallel reactance.

Derivation of Cell Number Index

Based on the dependent relationship between the measured impedance, cell number (more accurately, the viable cell number, or attached cell number) and cell attachment status, it is possible to derive a so-called "cell number index" (or cell index) from the measured impedance frequency spectra. Various methods for calculating such a cell number index can be used. In the following, we illustrate several methods for calculating such cell number index based on the change in resistance or reactance when cells are attached to the electrode structure with respect to the cells not attached to the electrode structure. The impedance (resistance and reactance) of the electrode structures with no cell attached but with same cell culture medium over the electrode structures is sometimes referred as baseline impedance. The baseline impedance may be obtained by one or more of the following ways: (1) the impedance measured for the electrode structures with a cell-free culture medium introduced into the well containing the electrode structures, wherein the culture medium is the same as that used for the impedance measurements for the condition where the cell attachment is monitored; (2) the impedance measured shortly (e.g. 10 minutes) after the cell-containing medium was applied to the wells comprising the electrode structures on the well bottom (during the short period after cell-containing medium addition, cells do not have enough time to attach to the electrode surfaces. The length of this short-period may depend on cell type and/or surface treatment or modification on the electrode surfaces); (3) the impedance measured for the electrode structures when all the cells in the well were killed by certain treatment (e.g. high-temperature treatment) and/or reagents (e.g. detergent) (for this method to be used, the treatment and/or reagents should not affect the dielectric property of the medium which is over the electrodes).

In one example, the cell number index can be calculated by:
(1) at each measured frequency, calculating the resistance ratio by dividing the measured resistance (when cells are attached to the electrodes) by the baseline resistance,
(2) finding or determining the maximum value in the resistance ratio over the frequency spectrum
(3) and subtracting one from the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In another example, the cell number index can be calculated by:
(1) At each measured frequency, calculating the resistance ratio by dividing the measured resistance (when cells are attached to the electrodes) to the baseline resistance,
(2) finding or determining the maximum value in the resistance ratio over the frequency spectrum
(3) and taking a log-value (e.g., based on 10 or e=2.718) of the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In one example, the cell number index can be calculated by:
(1) At each measured frequency, calculating the reactance ratio by dividing the measured reactance (when cells are attached to the electrodes) to the baseline reactance,
(2) finding or determining the maximum value in the reactance ratio over the frequency spectrum
(3) and subtracting one from the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In yet another example, the index can be calculated by
(1) At each measured frequency, calculating the resistance ratio by dividing the measured resistance (when cells are attached to the electrodes) to the baseline resistance,
(2) then calculating the relative change in resistance in each measured frequency by subtracting one from the resistance ratio,
(3) then integrating all the relative-change value.

In this case, "cell-number index" is derived based on multiple-frequency points, instead of single peak-frequency like above examples. Again, a zero or near-zero "cell number index" indicates that on cells are present on the electrodes. A higher value of "cell number index" indicates that, for same type of the cells and cells under similar physiological conditions, more cells are attached to the electrodes.

It is worthwhile to point out that it is not necessary to derive such a "cell number index" for utilizing the impedance information for monitoring cell conditions over the electrodes. Actually, one may choose to directly use impedance values (e.g., at a single fixed frequency; or at a maximum relative-change frequency, or at multiple frequencies) as an indicator of cell conditions.

Still, it is preferred for the present invention to derive "cell number index" and use such index to monitor cell conditions. There are several advantages of using "cell number index" to monitor attachment and/or viability conditions.

First, one can compare the performance of different electrode geometries by utilizing such cell number index.

Secondly, for a given electrode geometry, it is possible to construct "calibration curve" for depicting the relationship between the cell number and the cell number index by performing impedance measurements for different number of cells added to the electrodes (in such an experiment, it is important to make sure that the seeded cells have well-attached to the electrode surfaces). With such a calibration curve, when a new impedance measurement is performed, it is then possible to estimate cell number from the newly-measured cell number index.

Thirdly, cell number index can also be used to compare different surface conditions. For the same electrode geometry and same number of cells, a surface treatment given a larger cell number index indicates a better attachment for the cells to the electrode surface and/or better surface for cell attachment.

C. EXAMPLES

The following examples are intended to illustrate but not to limit the invention.

Example 1

Figure 3B:
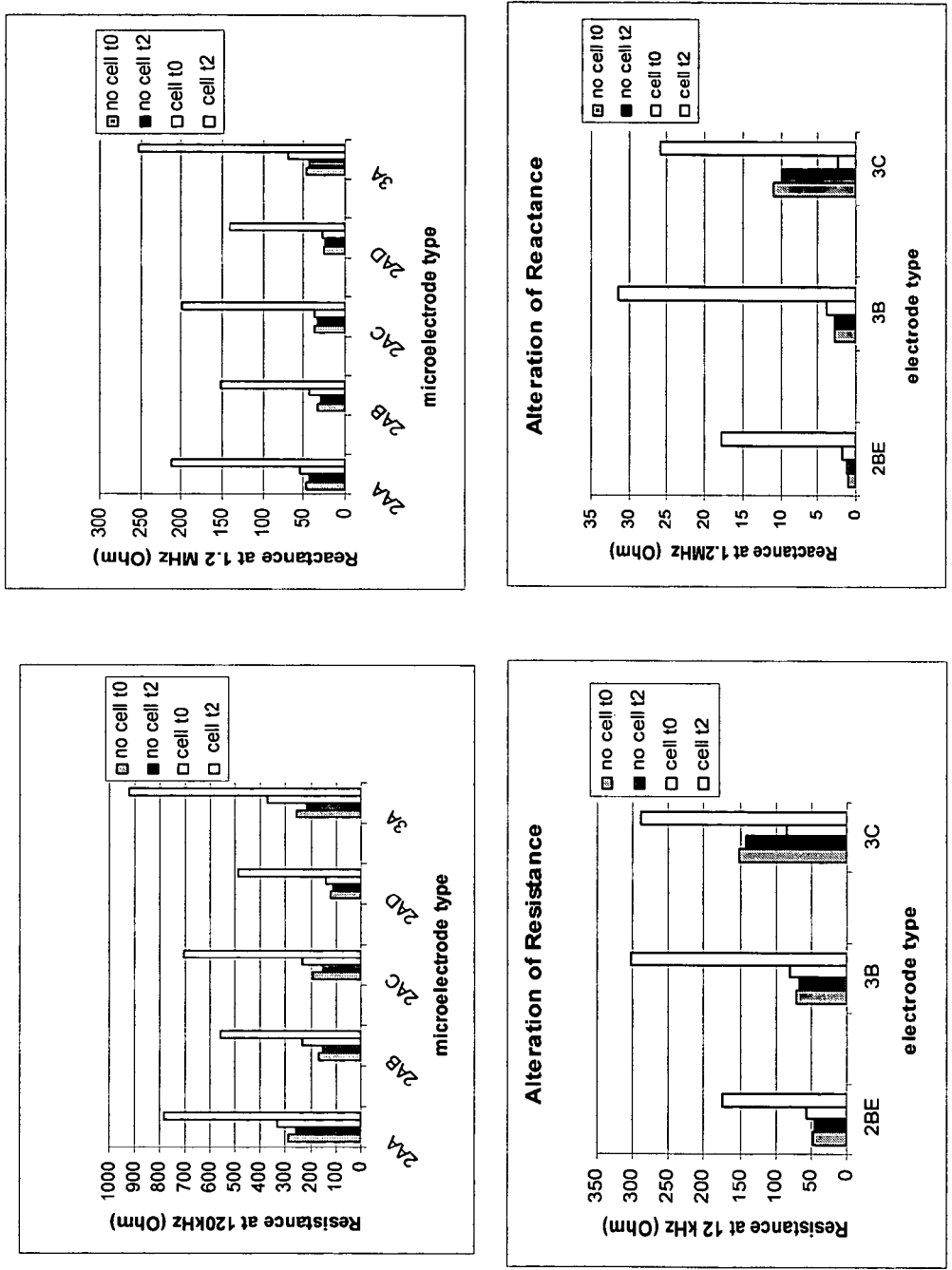
FIG. 3 illustrates resistance and capacitive reactance for 8 different types of electrodes attached with or without NIH 3T3 cells. The impedance indicated in the Y direction of FIGS. 3-7, 10, 11 is resistance and the capacitance indicated in the Y direction of FIGS. 16 through 29 is capacitive reactance. The unit for both resistance and capacitive reactance is Ohm.

Resistance and Capacitive Reactance for 8 Different Types of Electrodes Attached with or without Cells FIG. 3 illustrates impedance and capacitive reactance for 8 different types of electrodes attached with or without NIH 3T3 cells. The diameter of the electrode for 2AA, 2AB, 2AC, 2AD, and 3A is 1 mm; the diameter of the electrode for 2BE, 3B and 3C is 3 mm. The features of each electrode types are different and are provided in Table 2. The surfaces of electrodes were coated with chemical and biological molecules. In this experiment, fibronectin was used. After coating, NIH 3T3 cells were then seeded onto the surfaces of the electrodes. The resistance and reactance (capacitive reactance) were measured at 0 hour (immediately after seeding the cells) and at two hours after the seeding. (A, B) Resistance and capacitive reactance as a function of frequency for eight different types of electrodes. Increase in resistance and decrease in capacitive reactance were seen in all five electrode types attached with NIH 3T3 (2 hours after seeding the cells), compared with their corresponding microelectrodes on which cells were not attached (0 hour after seeding the cells) as indicated. (B) The bar graph summarizes the resistance and capacitive reactance changes at a given frequency as indicated. Here, the capacitive reactance value is the absolute value. Changes of resistance and capacitive reactance were only seen in the electrodes attached with NIH 3T3 cells.

TABLE 2 summary of some of the electrodes that have been tested.

| Electrode Structure Name | Substrate Material | Electrode Structure Type | Dimension (micron) | Diameter of active area |
|---|---|---|---|---|
| 2CF | Glass | Interdigitated | 48/28 | 6 mm |
| 2BE | Glass | Interdigitated | 48/18 | 3 mm |
| 2AA | Glass | Interdigitated | 80/50 | 1 mm |
| 2AB | Glass | Interdigitated | 80/15 | 1 mm |
| 2AC | Glass | Interdigitated | 50/30 | 1 mm |
| 2AD | Glass | Interdigitated | 50/10 | 1 mm |
| 3C | Glass | Circle-on-line | 60/160/180 | 3 mm |
| 3B | Glass | Circle-on-line | 30/80/90 | 3 mm |
| 3A | Glass | Circle-on-line | 30/80/90 | 1 mm |
| | Plastics (Kapton) | Interdigitated | 50/50 | |

Electrodes 2AA, 2AB, 2AC, 2AD, 2BE and 2CF are interdigitated electrodes and have values 80/50, 80/15, 80/30, 50/10, 48/18 and 48/28 for electrode width and gap width, respectively.

Electrodes 3A, 3B and 3C are circle-on-stick (or circle on a line) electrodes having 30/80/90, 30/80/90 and 60/160/180 for the stick (i.e. line) width and stick (i.e. line) gap, electrode circle diameter, respectively.

Example 2

Quantitative Measurement of Cells Using the 3B Electrode

Figure 4:
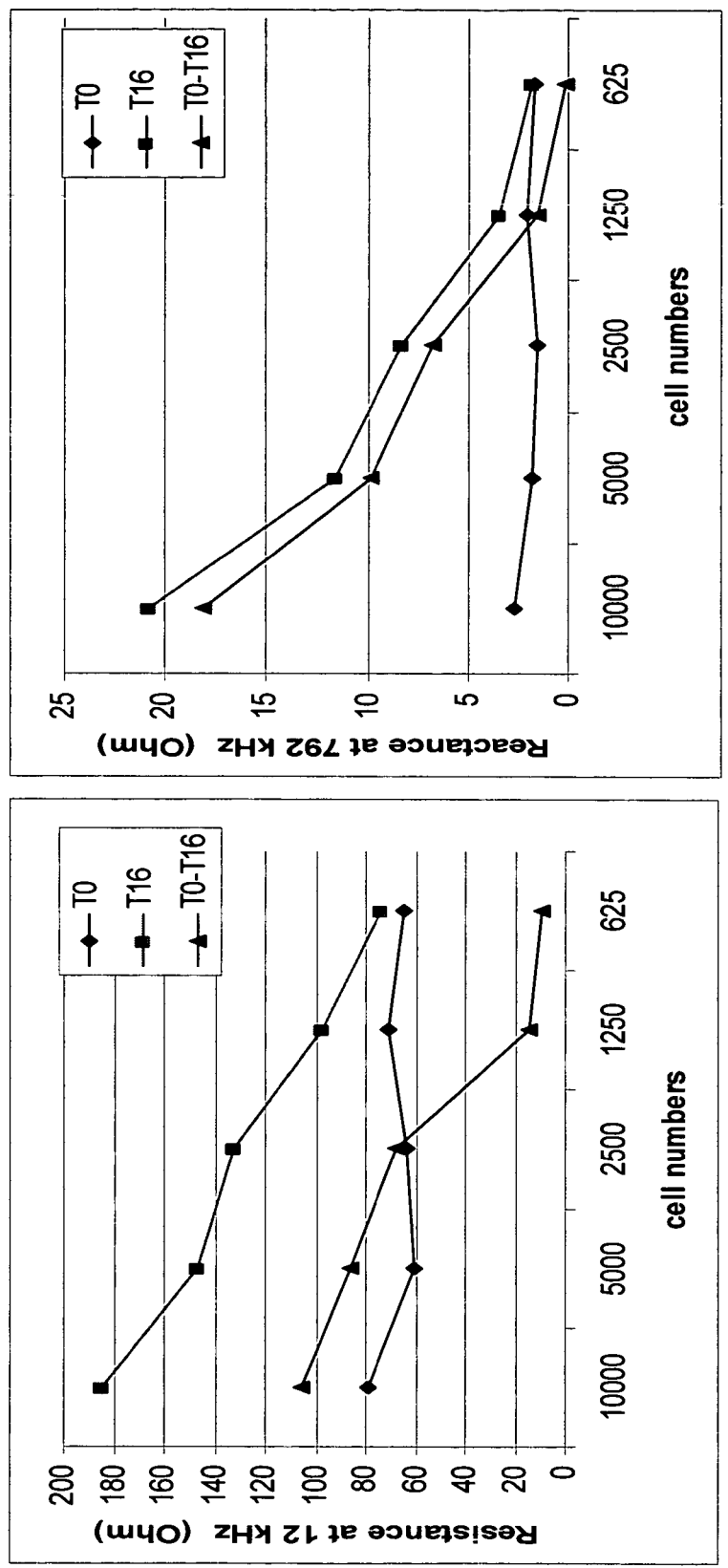
FIG. 4 illustrates quantitative measurement of cells using the 3B electrode.

FIG. 4 illustrates quantitative measurement of cells using the 3B electrode. Serial diluted NIH 3T3 cells (10,000 cells, 5,000 cells, 2,500 cells, 1,250 cells and 625 cells) were added onto the surface of the 3B electrode coated with fibronectin. Resistance and capacitive reactance were measured at 0 hour (immediately after seeding), and at 16 hours after seeding. The curves represent resistance and capacitive reactance data from a given frequency as indicated. T0 curve indicates the baseline resistance and capacitive reactance for the electrodes onto which cells had not been attached. T0-T16 curve indicates the resistance and capacitive reactance changes after cell attached to the electrodes. The current 3B electrode is able to sense less than 600 cells. The dynamic quantification range of the current 3B electrode is between 10,000 and 500 for NIH 3T3 cells.

Example 3

Figure 5:
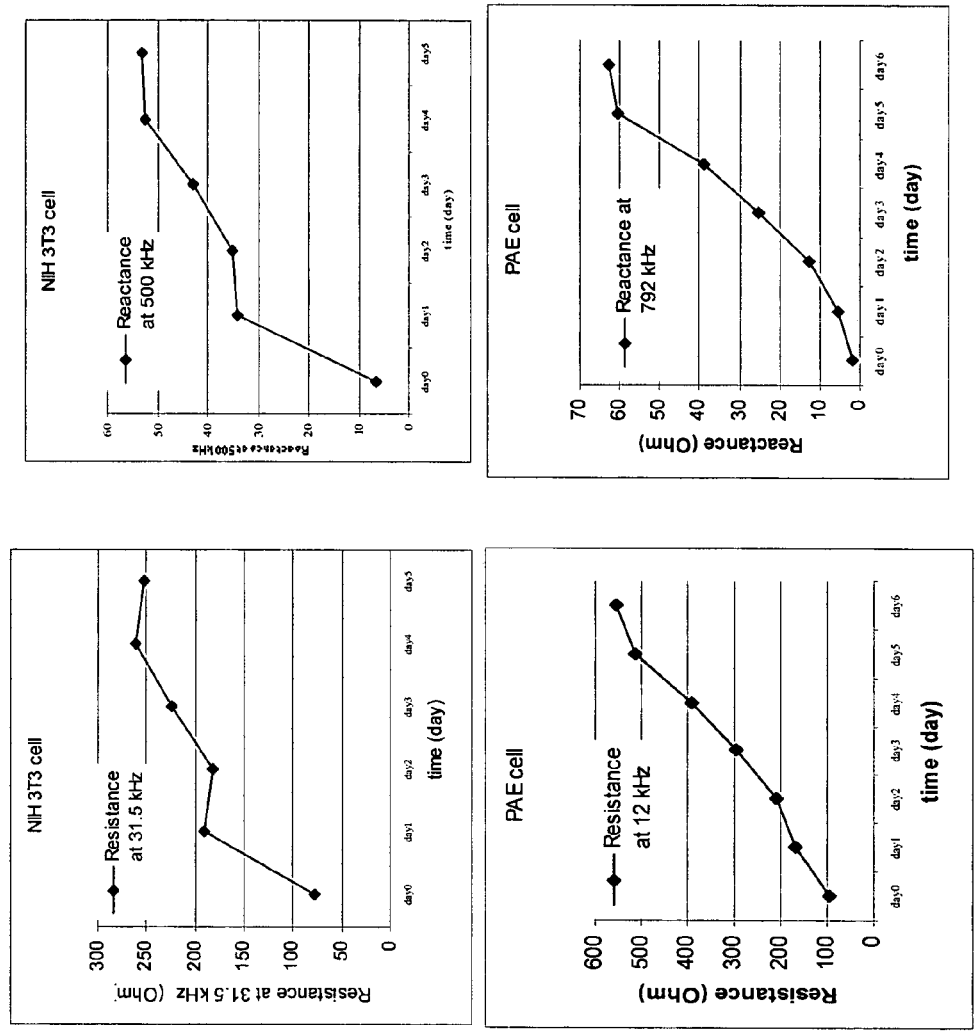
FIG. 5 illustrates real time monitoring of NIH 3T3 and PAE cell proliferation using the 3C and 3B electrodes.

Real Time Monitoring of NIH 3T3 and PAE Cell Proliferation Using the 3C and 3B Electrodes FIG. 5 illustrates real time monitoring of NIH 3T3 and porcine aortic endothelia (PAE) cell proliferation using the 3C and 3B electrodes. Two thousand five hundred NIH 3T3 cells and 2,500 PAE cells were seeded onto the coated electrodes. For NIH 3T3 cells, the electrode was coated with fibronectin; for PAE cells, the electrode was coated with gelatin. Resistance and capacitive reactance were measured daily to monitor the cell proliferation. Day 0 indicates the measurement immediately after seeding of the cells. Here, the capacitive reactance value shown in the figure is the absolute value. The resistance and capacitive reactance increase with the cultivation time (days) in both cell types, indicating cell proliferation. The NIH 3T3 cell growth plateaued at day 4, while PAE cell growth plateaued at day 5, suggesting the NIH 3T3 cells proliferate faster than PAE.

Example 4

Figure 6:
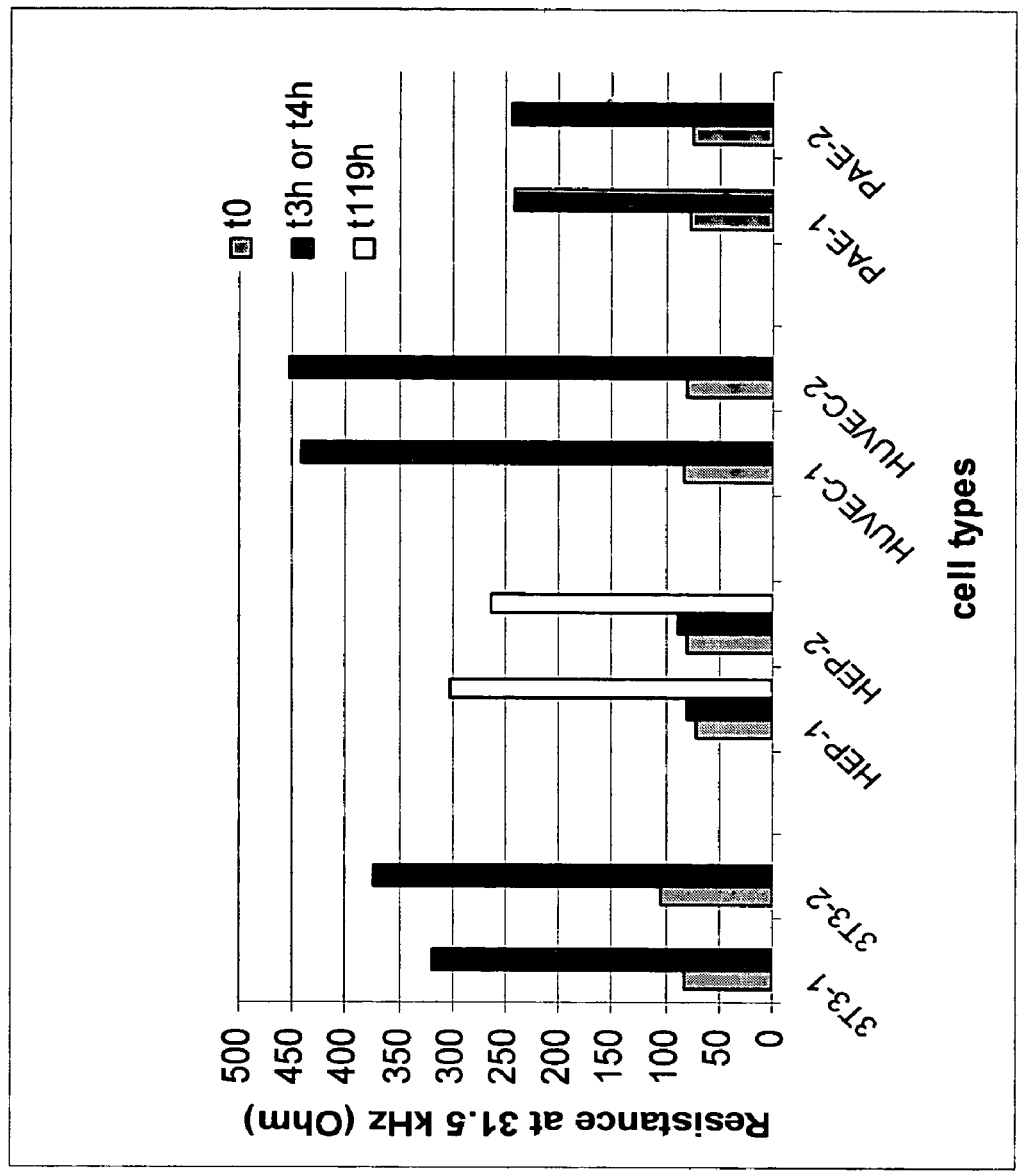
FIG. 6 illustrates impedance comparison among four different cell types using the 3C electrode.

Resistance Comparison Among Four Different Cell Types Using the 3C Electrode FIG. 6 illustrates resistance comparison among four different cell types using the 3C electrode. Resistance for four cell types were measured using the 3C electrode. The four cell types were the NIH 3T3 cells (mouse fibroblasts), the HEP-G2 cells (human hepatocytes), the PAE cells (pig endothelia cells) and the HUVEC (human endothelia cells). For the NIH 3T3 and the HEP-G2, the electrode was coated with fibronectin; for the PAE and HUVEC, the electrode was coated with gelatin. Two electrodes were used for each cell type as indicated. For NIH 3T3 and HEP-G2, 10,000 cells were seeded onto each electrode; for HUVEC and PAE, 20000 cells were seeded onto each electrode. The resistance and capacitive reactance were measured (only resistance data were shown here) at time 0 and 3 or 4 hours after seeding. For HEP-G2, resistance was measured at 119 hours after seeding. Significant increases in resistance were seen in NIH 3T3 cells, HUVEC and PAE cells at 3 or 4 hours. In contrast, subtle increase in resistance was seen in HEP-G2 at 4 hours after seeding, indicating the slow attachment of hepatocytes to the electrodes. The resistance for HEP-G2 increased steadily after overnight incubation (data not shown) and reached to plateau at 119 hour after seeding.

Example 5

Reproducibility of Resistance Measurement

Figure 7:
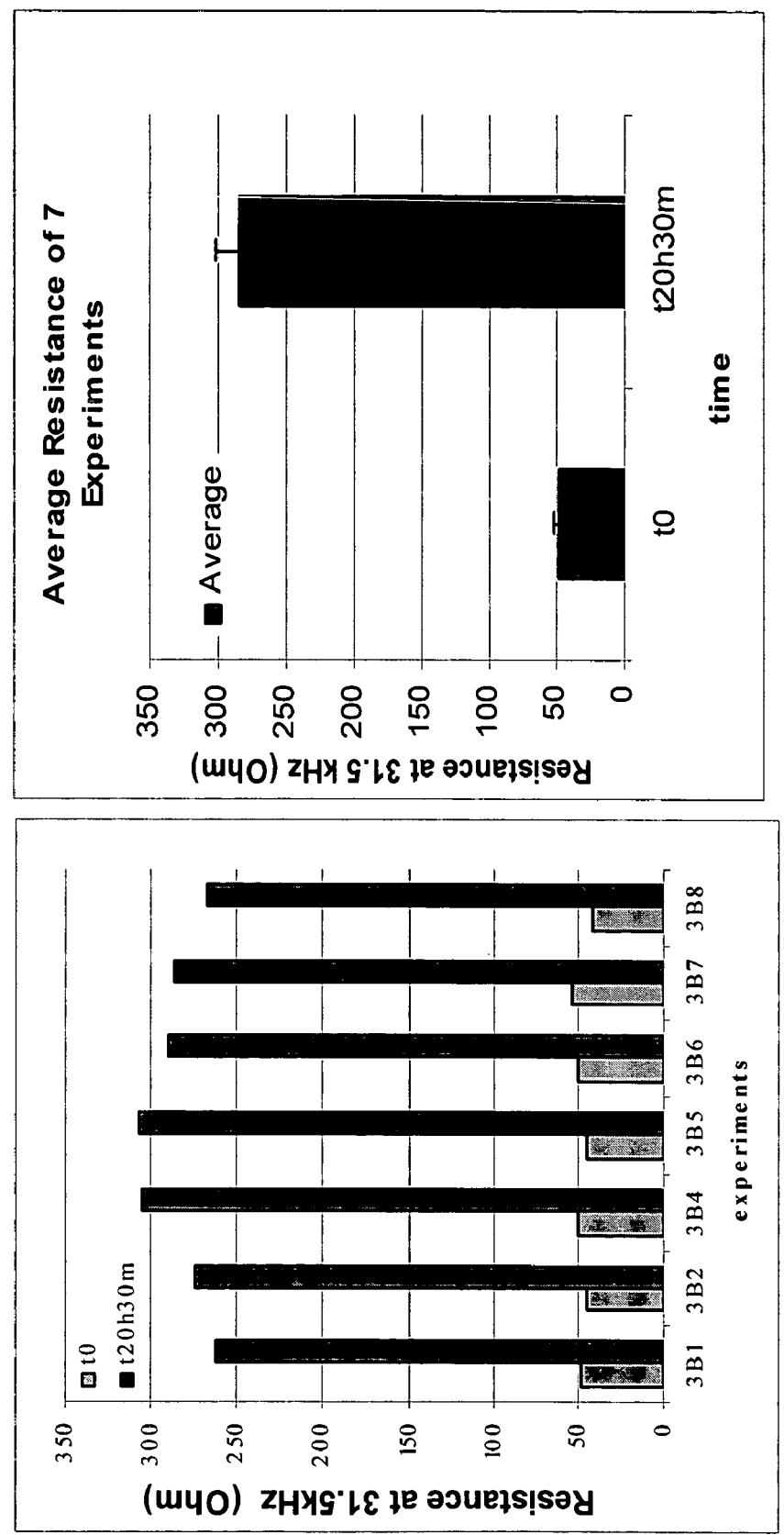
FIG. 7 illustrates reproducibility of impedance measurement.

FIG. 7 illustrates reproducibility of resistance measurement. The reproducibility was tested on seven electrodes (3B) seeded with HUVEC. The electrodes were coated with gelatin and seeded with 15,000 HUVEC cells per electrode. The resistance for each electrode was measure immediately after seeding (t0), and 20 hours and 30 minutes after seeding. Significant increase in resistance was seen after 20 hour incubation indicating the cell attachment onto electrode. The average resistance for t0 is 47.4 with standard deviation of 3.9; for t20 h30 m, the average resistance is 284.8 with standard deviation of 17.2. The coefficient of variance for t0 is 8.3%, and for t20 h30 m is 6.1.

Example 6

Figure 22:
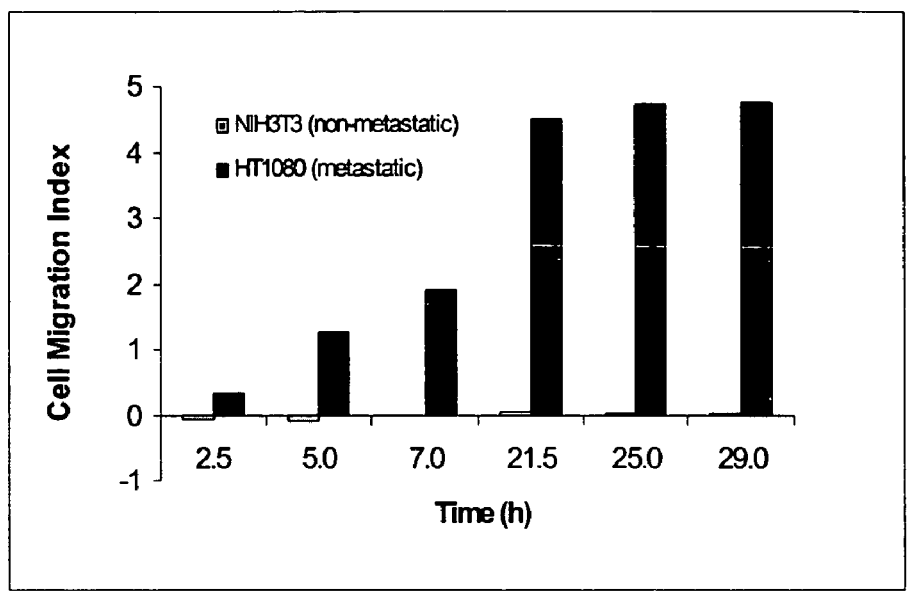
FIG. 22 shows comparison in invasion and migration activities between noninvasive NIH 3T3 cells and invasive HT1080 cells on cell migration devices where the electrode structures were incorporated onto the bottom surface of the lower chamber, as illustrated in FIG. 8.

Comparison in Invasion and Migration Activities between Noninvasive NIH 3T3 Cells and Invasive HT1080 Cells as Determined in a Cell Migration Apparatus with Electrode Structures Incorporated onto the Bottom Surface of the Lower Chamber FIG. 22 shows comparison in invasion and migration activities between noninvasive NIH 3T3 cells and invasive HT1080 cells on our electronic cell migration apparatuses where the electrode structures were incorporated onto the bottom surface of the lower chamber, as illustrated in FIG. 1. In experiment, the cell migration apparatuses keep the conventional trans-well migration apparatus format, while an electrode sensor chip (i.e., a glass substrate on which electrode structures were fabricated) was mounted onto the bottom surface of each lower chamber. When cells migrate across the microporous membrane, drop onto and attach to the electrode structures, the cell-substrate impedance is detected and quantified by an impedance analyzer. Two cell lines, the NIH 3T3 line and the HT1080 line, were used to test the cell migration devices. NIH 3T3 cell line is a noninvasive cell line, whereas HT1080 cell line has been well characterized as an invasive cell line showing a high invasion and migration activities both in in vitro migration assays and in vivo migration assays. Both NIH 3T3 cells (purchased from ATCC) and HT1080 cells (purchased from ATCC) were cultivated in DMEM containing 10% FBS. In the migration experiment, cells of both types were trypsinized and counted. The cell suspension was made. Since the electrode sensor chips (i.e., glass substrates on which electrode structures were fabricated) were integrated or incorporated into a 24-well trans-well migration apparatus, the standard trans-well migration assay was performed on our electronic cell migration apparatuses. Briefly, the electrode sensor in the lower chamber and microporous membrane of the insert were first coated with an extracellular matrix protein. In this experiment, both electrode sensors and microporous membrane were coated with 50 µg/ml fibronectin in room temperature for one hour. After wash with phosphate buffed saline, cell culture media (10% FBS DMEM) were added into the lower chambers where the precoated electrode sensors were mounted. Then, an insert was placed in a low chamber. In each insert, $2 \times 10^5$ cells of either NIH 3T3 or HT1080 cells were added. The electrode structures were then connected to the impedance analyzer via connection pads on the electrode sensor chips. The invasion and migration activities were measured in real time without disturbing the experiment. In the figure, the Y axis represents cell migration index, which was calculated based on measured resistance of electrode structures at different times of experiment and at the beginning (baseline resistance, no cells were attached, of the experiment) at different frequencies. The cell migration index was calculated in a similar way to that used for calculating "cell number index" based on the maximum ratio of the measured resistance at a given time to the baseline resistance. The cell migration index correlates well with the number of cells arrived in the bottom chamber and correlates well with cell invasion and migration activities. The X axis represents the time intervals of each measurement. As indicated, the invasion and migration activities of HT1080 cells were steadily increased with time. In contrast, the noninvasive NIH 3T3 cells have shown undetectable invasion activity during the entire experiment. This result is consistent with previous reports lines using the conventional transwell apparatus. Moreover, the cell migration apparatuses of the present invention and used here provide real time, continuous and labeling free measurement of cancer cell invasion and migration activities.

Example 7

Figure 23:
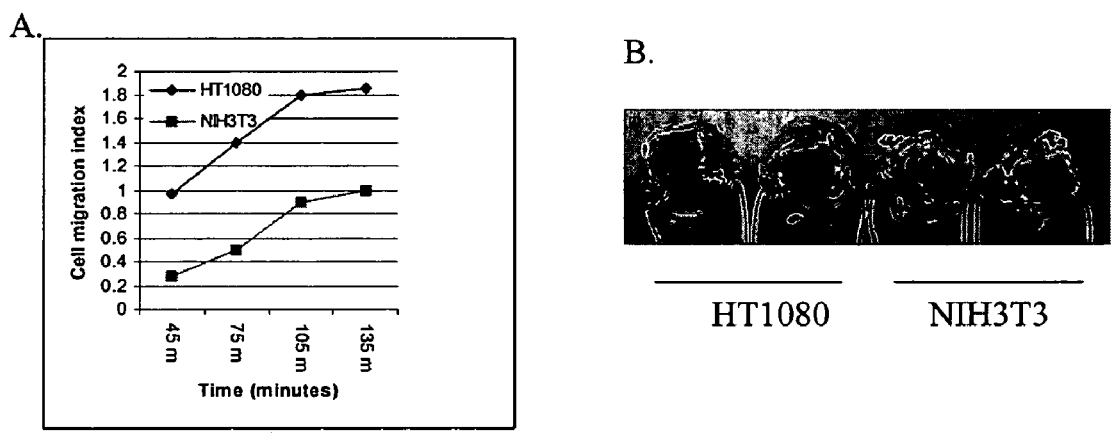
FIG. 23(A) shows the comparison in invasion and migration activity between noninvasive NIH 3T3 cells and invasive HT1080 cells on cell migration devices (FIG. 23(B)) where the electrode structures were built onto the microporous membrane of the insert (similar to the structures shown in FIG. 16).

Comparison in Invasion and Migration Activities between Noninvasive NIH 3T3 Cells and Invasive HT1080 Cells as Determined in a Cell Migration Apparatus where Electrode Structures Were Built onto the Microporous Membrane of the Insert FIG. 23(A) shows the comparison in invasion and migration activity between noninvasive NIH 3T3 cells and invasive HT1080 cells on cell migration devices (Figure 40(B)) where the electrode structures were built onto the microporous membrane of the insert (similar to the structures shown in FIG. 17). In this cell migration apparatus, an electrode structure unit was built onto an bottom side of the insert (FIG. 23(B)). Therefore, when cells invade through an extracellular matrix layer, migrate across the microporous membrane, the invaded cells directly attach onto the electrode structures, and such cell-electrode interaction are sensed and the impedance between the electrode structures were measured and quantified. Two cell lines, the NIH 3T3 line and the HT1080 line, were used for testing such cell migration apparatuses. NIH 3T3 cell line is a noninvasive cell line, whereas HT1080 cell line has been well characterized as an invasive cell line showing a high invasion and migration activities both in in vitro migration assays and in vivo migration assays. Both NIH 3T3 cells (purchased from ATCC) and HT1080 cells (purchased from ATCC) were cultivated in DMEM containing 10% FBS. In the migration experiment, both cells were trypsinized and counted. The cell suspension was made. Since microporous membranes with fabricated electrode structures were bonded to insert wells suitable for a commercial 24-well migration apparatus, the standard trans-well migration assay was performed on our cell migration apparatuses. Briefly, the microporous membrane and the built-in membrane electrode sensor array of the insert were first coated with an extracellular matrix protein. In this experiment, both membrane electrode sensors and microporous membranes were coated with 50 μg/ml fibronectin in room temperature for one hour. After wash with phosphate buffed saline, cell culture media (10% FBS DMEM) were added into the lower chambers where the precoated electrode sensors were mounted. Then, an insert was placed in a low chamber. In each insert, $2\times10^5$ cells of either NIH 3T3 or HT1080 cells were added. As shown in FIG. 23(B), electrical wires were bonded to the connection pads on the membrane with conductive adhesive and they were then connected to the impedance analyzer. The area where the connection pads bonded to electrical wires were covered with biocompatible silicone-based adhesive. The invasion and migration activities were measured in real time without disturbing the experiment. To validate the sensor measurement, at the end of the experiment, the cells migrate across the membrane and attached onto the electrode sensors on the microporous membrane were fixed with 100% methanol for 5 min followed by staining with Giemsa stain (Sigma Diagnostics) for 30 min. (A) measurement of invasion and migration activities of NIH 3T3 cells and HT1080 cells. The Y axis represents cell migration index, which was calculated based on measured resistance of electrode structures at different times of experiment and at the beginning (baseline resistance, no cells were attached, of the experiment) at different frequencies. The cell migration index is calculated in a similar way to that used for calculating "cell number index" based on the maximum ratio of the measured resistance at a given time to the baseline resistance. The cell migration index correlates well with the number of cells arrived in the bottom chamber and correlates well with cell invasion and migration activities. The X axis represents the time intervals of each measurement. As indicated, the migration activities of HT1080 cells were increased with time. The migration activity of the noninvasive NIH 3T3 cells is weaker than that of the HT1080. (B) Gimsa staining of the migrated cells on the electrode sensor arrays on the opposite side of the microporous membrane. As indicated in the figure, the color density of the HT1080was much higher than that of the NIH 3T3 cells, which was consistent with the result obtained from the measurement of the impedance between electrode structures on the microporous membrane. Unlike the apparatuses described in the FIG. 22, where the electrode structures detected the cells migrated and dropped onto the bottom surface of the lower chamber, the apparatus here can detect and measure the cell migration once cells migrate across the microporous membrane. Therefore, this cell migration apparatus having electrode structures fabricated on the membrane can detect the cell migration more directly and rapidly than the apparatuses described FIG. 22.

Example 8

Real Time Monitoring of the Inhibitory Effect of Doxycycline on Cancer Cell Invasion and Migration Using Cell Migration Apparatuses where Electrode Structures Were Built onto the Microporous Membrane of the Insert FIG. 24 shows results of real time monitoring of the inhibitory effect of doxycycline on cancer cell invasion and migration using cell migration devices where the the electrode structures were built onto the microporous membrane of the insert (similar to the structures shown in FIG. 17). (A) A time and dose-dependent inhibition of HT1080 cell invasion and migration by doxycycline. (B) Real-time monitoring of the dynamic inhibitory effect of doxycycline on HT1080 cell invasion and migration using a fully automated instrment with software controlled data acquisition for impedance measurement. As indicated in FIG. 24(B), the migration process was continuously monitored every 15 min. The cell migration apparatus (described in FIG. 23) with electrode structures fabricated on microporous membranes of the insert well was used to kinetically monitor drug inhibitory effect on cancer cell invasion and migration. A dose and time-dependent inhibitory effect of doxycycline (Sigma) on HT1080 cell invasion and migration was measured on the cell migration apparatus. Briefly, the microporous membrane (10 um in diameter) and the electrode structures were coated with 50 μg/ml fibronectin at room temperature for one hour followed by wash with phosphate buffed saline. HT1080 cells were trypsinized and a $10^6$ cells/ml suspension was made. In the lower chamber, 1 ml of culture media containing different concentrations of doxycycline was added. DMSO, the solvent for doxycycline was used as a vehicle control. In each insert, 200 μs of HT1080 cell suspension ($2\times10^5$ cells) containing either doxycycline or the vehicle were added. An impedance analyzer was automatically and electronically switched to electrode structures of different insert wells. After connecting the electrode structures to cell invasion and migration activities in the presence or the absence of doxycycline were monitored at different time intervals without disturbing the experiment. The migration index (or cell migration index) was calculated in the same way as those shown in FIGS. 22 and 23.

Example 9

A Device for Monitoring Migration in Real Time

1. The Electronic Cell Chip Design

Figure 8:
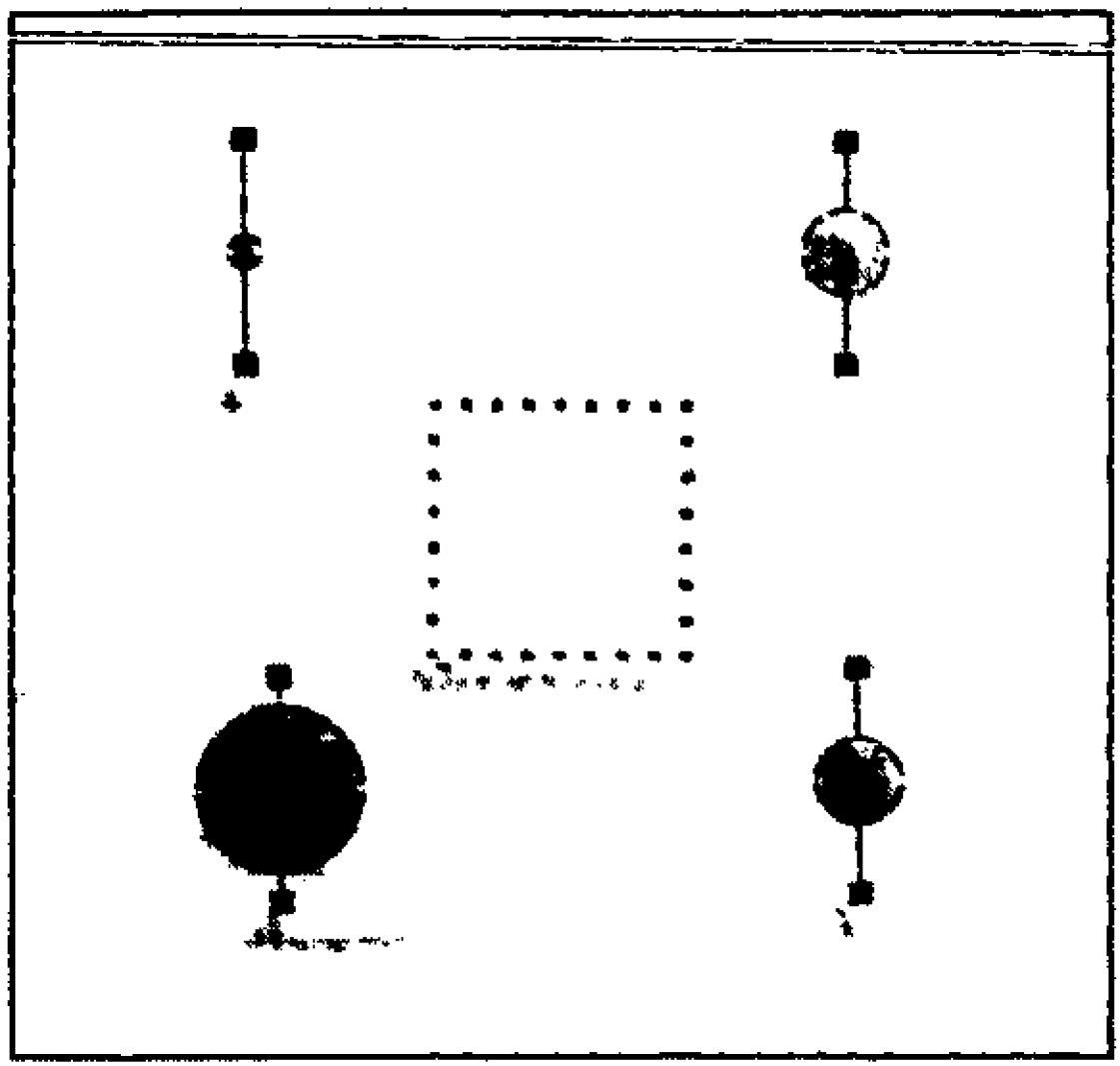
FIG. 8 illustrates an electronic cell chip design. The figure shows five representative designs of the electronic cell chips. The gold electrodes with different geometries and sizes are centered on the glass substrate. The size of the glass substrate is 1 cm×1 cm. The gold electrode can be connected to electric detection interface via connection electrode pads located on the sides of the glass substrate.

FIG. 8 illustrates an electronic cell chip design. The figure shows five representative designs of the electronic cell chips. The gold electrodes with different geometries and sizes are centered on the glass substrate. The size of the glass substrate is 1 cm×1 cm. The gold electrode can be connected to electric detection interface via connection electrode pads located on the sides of the glass substrate.

2. The Mechanisms of Detecting Cells on Electronic Cell Chips

An electrode can be represented as a series RC circuit (Warburg, E. Ann. Phys. 1901, 6, 125-135.) and both resistance and the capacitance of a conductor electrolyte vary as f-κ, where 0<κ<1 and f is the frequency. For a bare electrode in the absence of the cells (FIG. 9), the numerical value of $R_{sol}$ or the constriction resistance is simply equal to the asymptotic value at high frequency of the measured resistance (Z=Z0). The resistance or impedance is almost identical for cell free electrodes coated with chemicals or proteins (Luong, J. H. T., M. Habibi-Rezaei, J. Meghrous, C. Xiao, and A. Kamen. 2001. Monitoring motility, spreading and mortality of adherent insect cells using an impedance sensor. Anal. Chem. 73, 1844-1848.). In contrast, the impedance value of an electrode increases significantly after a cell attaches to the electrode and spreads (Z=Zcell). The increase in impedance values is correlated with the cell-electrode adhesion and the covered area of the electrode. Accordingly, for a given cell type (adherent cells), changes in cell numbers can be represented by corresponding changes in impedance values.

3. Detection of Cells on Electrodes by Measuring Impedance

As a basis for comparative studies, a testing device was developed, which contains an electronic cell chip (FIG. 8), an electronic interface, built on a printed-circuit-board, and a culture well mounted onto the chip. Therefore, the base testing device contains only one test unit.

Two chip designs with different geometries were first tested. The design 1 contains an electrode of 1 mm in diameter and the design 2 contains an electrode of 3 mm in diameter. The detecting area is different between two designs. NIH 3T3 cells (obtained from ATCC) were used for the test. For each test, two devices were used, one for media and the other for the cells. Electrodes on the testing device were coated with fibronectin (50μ/ml) for 1 h at room temperature. After coating, either 100 μl of NIH 3T3 cell suspension (10,000 cells) or 100 μl of media was added to a device. Resistance and capacitive reactance at different frequencies were measured by 1,260 Impedance Analyzer (Solartron Inc. UK) immediately after seeding (t0) and at 2 h after the seeding (t2). At t0, resistance and capacitive reactance were similar between the devices with cells and without cells. At t2, a significant increase in resistance values at different frequencies was seen in the device with cells, whereas no changes were seen in the device without cells, indicating cell attaching and spreading on the electrodes. Both design showed a similar result (data not shown).

4. Detecting Different Cell Types on the Testing Devices

The device was further tested using four cell types including two primary human cell types, HUVEC (obtained from ATCC) and primary human hepatocytes (obtained from SciеnCell Inc. San Diego, Calif.) and two cell lines, the NIH 3T3 line and the PAE line (porcine aortic endothelia cell, obtained from ATCC). Significant increase in resistance was seen for all cell types at 3 or 4 hours after seeding, as shown in FIG. 6.

5. Cell Proliferation

Figure 10:
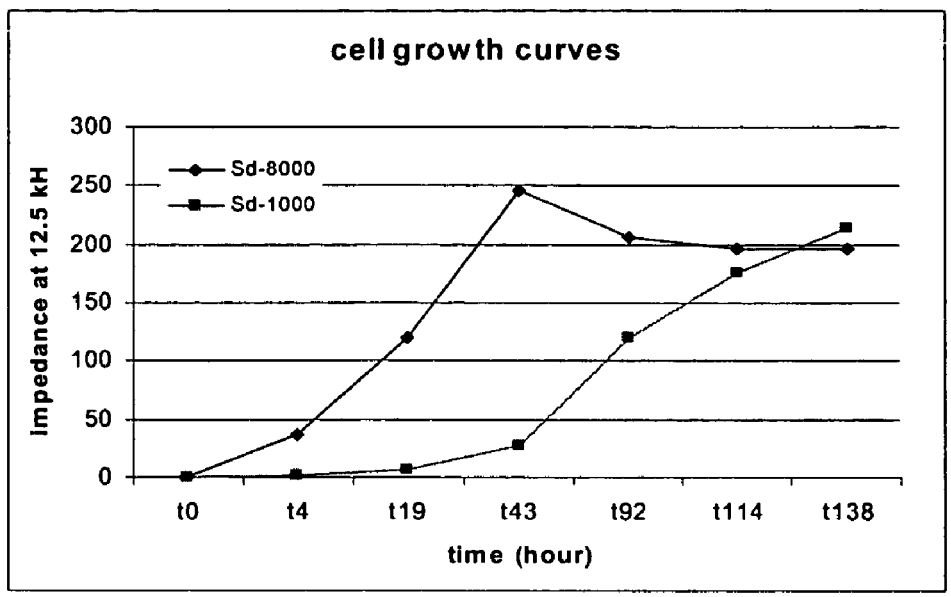
FIG. 10 illustrates real time monitoring of PAE cell proliferation on the testing devices. Cells were seeded onto the coated electrodes at different densities (8,000 cells and 1,000 cells). Resistance (shown in Figure as impedance) and reactance (not shown) were measured at different time intervals as indicated to monitor the cell proliferation. "t0" indicates the measurement immediately after seeding of the cells. The impedance (i.e., resistance) value increases with the cultivation time at both cell seeding densities, indicating cell proliferation. The cells with a high seeding density proliferated much faster than cells with a lower seeding density. Sd: seeding density.

The cell proliferation was tested on the testing device using the PAE cells. In this study, PAE cells were seeded at different densities (8,000 cells and 1,000 cells) to continuously monitor cell proliferation rates at different cell seeding densities. Resistance was then measured at different time intervals without destructing the culture. As shown in FIG. 10, steadily increase in resistance values was seen with cultivating time from both devices, indicating increase in cell numbers over cultivating time. Notably, resistance increased much faster in the device with high cell seeding density than with low cell seeding density, indicating the cell proliferated much faster with higher cell seeding density. This was confirmed by observation under a light microscope (data not shown). These results indicate that the device is able to continuously monitor cell proliferation in real time, and no labeling is required for such measurement.

6. Quantitation and Sensitivity of Measuring Cells on the Testing Device

Figure 11:
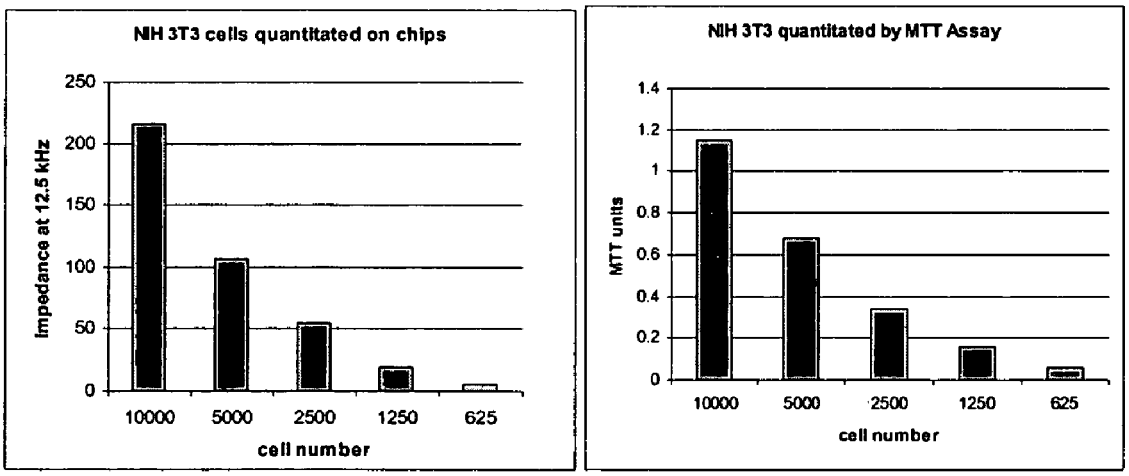
FIG. 11 illustrates quantitative measurement of cells on the testing devices and by MTT assay. Serially diluted NIH 3T3 cells (10,000 cells, 5,000 cells, 2,500 cells, 1,250 cells and 625 cells) were added either to the testing devices coated with fibronectin or a 96-well plate. For the assay using devices, impedance (i.e. resistance for this Figure) was measured at 16 hours after seeding. For MTT assay, cells were stained with MTT dye at 16 hours after seeding and then read on an ELISA plate reader at 540 nm. As shown in the figure, the device can quantitatively measure cell number changes. The results from both methods are almost identical. Moreover, the current chip design is able to detect less than 600 cells, which is also comparable with MTT assay.
Figure 12:
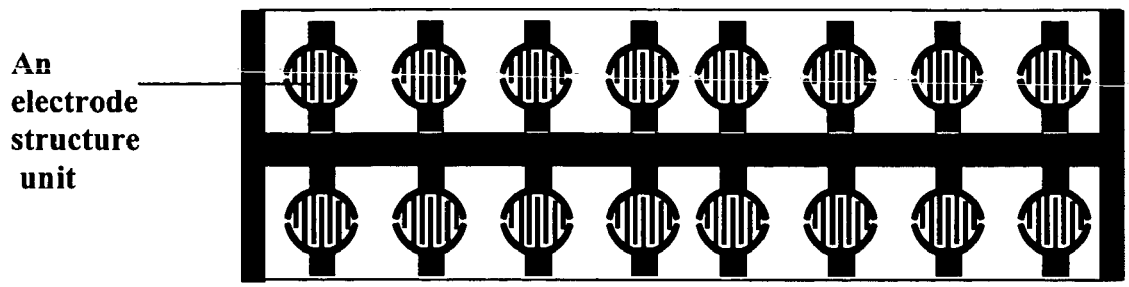
FIG. 12 illustrates a 16-unit electronic cell chip used for migration assay.
Figure 13:
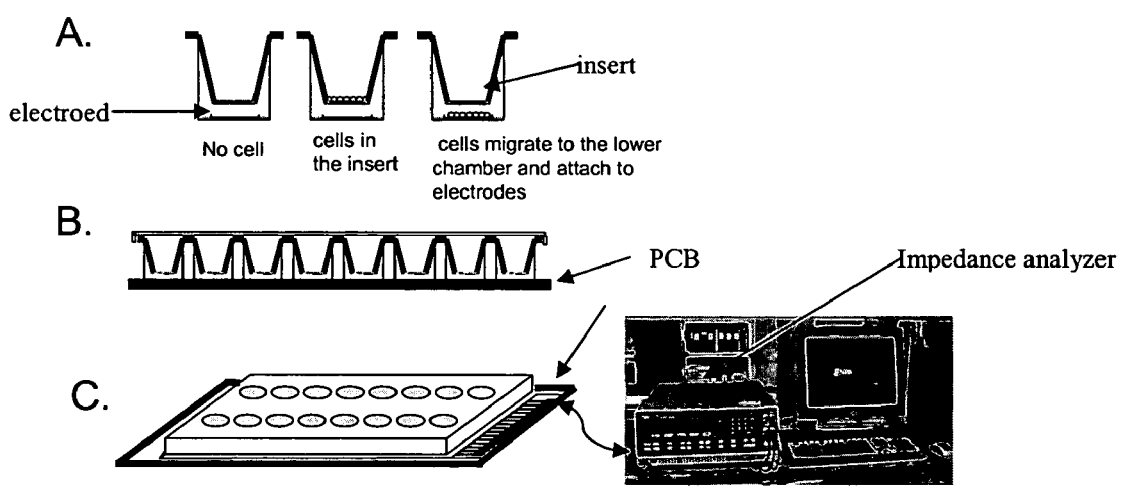
FIG. 13 illustrates an exemplary device for migration assay. (A) shows a test unit contains an electronic cell chip chamber (lower chamber), an insert with a microporous membrane. Cells are seeded into the insert and then incubated. The invasive cells invaded and migrated across the membrane and attached to the electrode on the chip, which can be detected by the impedance analyzer. (B) shows a cross section of the device containing 8 units in a row. (C) shows a 16-unite device and connection with an impedance analyzer.
Figure 14:
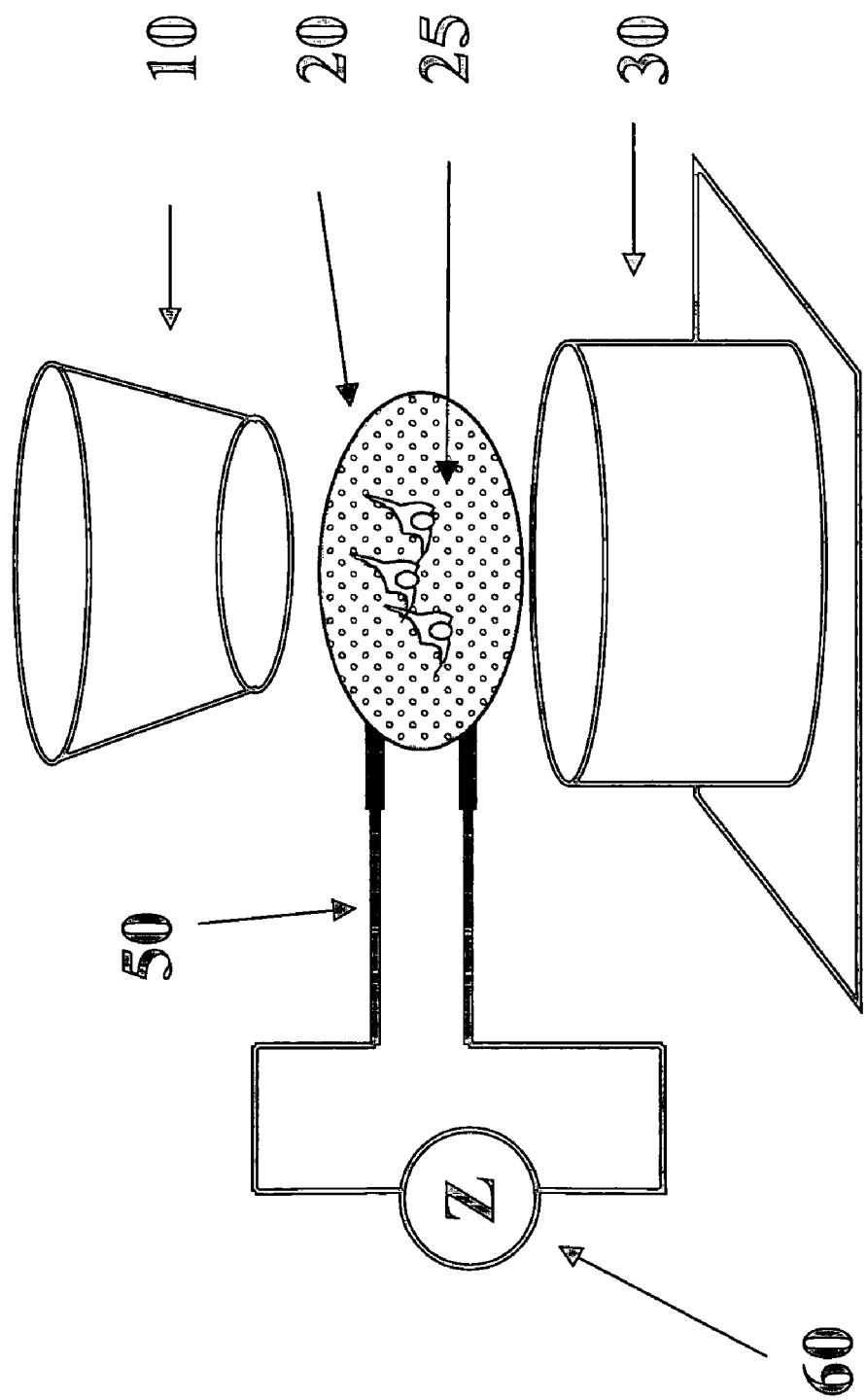
FIG. 14 is a schematic representation of cell migration/invasion measurement device, including, top chamber 10, trans-well membrane 20 with impedance-based counting electrodes or electrode arrays 25, and bottom chamber 30. Electrode arrays 25 are on the bottom surface of the trans-well membrane 20, facing the bottom chamber 30. Impedance analyzer or impedance measurement circuits 60 are operatively connected to the electrodes 25 through certain electric connection cables/wires or other methods for monitoring cell numbers on the electrodes. The impedance change of the electrodes as a result of adhesion of cells that have migrated from the top chamber reflects the number of the cells migrated from the top chamber.

The quantitative capacity and sensitivity of the device for cell measurement were tested in comparison with MTT assay, which is commonly used for cell quantitation[48]. Serially diluted NIH 3T3 cells were added to the testing devices or a 96-well microtiter plate (FIG. 11). The measurement was done after overnight incubation at 37° C., 5% $CO_2$ either by the resistance measurement or by MTT staining. As shown in FIG. 28, data obtained from both methods are very comparable. A linear quantitation can be achieved by the resistance measurement on the device. Indeed, the device displayed a sensitivity level comparable to the MTT assay (less than 600 cells).

7. Reproducibility of the Testing Device

Reproducibility of the resistance measurement on the testing device was tested using three different cell types. Here, a representative result indicating the performance capabilities of the device was achieved using primary human hepatocytes. For the test, 6 devices were used and resistance was measured immediately after seeding cells (t0) and at 4 hours after the seeding (t4). The CVs for t0 and t4 were calculated (FIG. 7). The CV_t0 represents the variation of the devices, while the CV_t4 represents the variation of devices plus cell adhesion and spreading. As shown in FIG. 7, the resistance measurement on the testing device is very reproducible with low CVs both at t0 and t4. The CV can be further reduced by using a modified device as described below.

D. Methods

For a migration assay, plastic wells on a multi-well substrate were pre-filled with buffer solutions containing chemoattractants. A trans-membrane well containing plastic plate (available from BD Biosciences) is then inserted into the plastic well of the measurement cartridge. After cells are loaded onto the trans-membrane wells, electrode impedances are monitored in the frequency range between 1 kHz and 1 MHz. To ensure no or minimal effects of electric field application to the cells, a 5 or 10 mV is applied to the electrodes. Detailed protocol is described below.

Protocol for the Migration Analysis on the Electronic Device
1. Electrode Coating:

Cell adhesion molecules are used for coating. For fibronectin, 50 ul of 50 ug/ml fibronectin was added to each unit at room temperature for 1 hour followed by wash with PBS for three times. For gelatin, 50 ul of 1% gelatin was added to each unit at 37° C. for 30 min, and 50 ul of 0.5% glutaraldehyde was added for 25 min at room temperature to fix the coated gelatin, which was washed with PBS before additiona of 50 ul of 0.1 M glycine for 30 min at room temperature to block the free aldehydes. Washing with PBS was performed again for 3 times. Precoated devices may alternatively be provided.

2. ECM Coating:

50 ul of ECM solution was added to an insert and incubated for overnight at room temperature. Depending on the assay requirements, ECM materials useful in the assay include BD Magtrgel matix (BD Biosciences), fibronectin (Sigma), collagens (Sigma or BD Biosciences), and laminin (BD Biosciences). The insert is washed with PBS. Precoated inserts may also be provided.

3. Seeding Cells:

100 ul of cell suspension ($10^5$ cells) was added to a precoated insert, while 100 ul of conditioned media containing a chemoattractant was added to the electronic cell chip chamber. After placement of the insert into the chamber, impedance was measured as t0. The device was incubated at 37° C., 5% $CO_2$, in a 100% humidity chamber. Migration was monitored in real time by measuring impedance at different time intervals.

4. Data Acquisition:

Data was stored in and analyzed using a software program (125505S Z plot) bundled with the purchased 1260 Impedance Analyzer (Solartron Analytical).

E. LITERATURE

The following references are cited and incorporated herein by this reference:

1. Perou, C. M., P. O. Brown and D. Botstein. 2000. Tumor classification using gene expression patterns from DNA microarrays. Molecular Medicine Today. December, 67-72.
2. Muller, A., B. Homey, H. Soto, N. Ge, and A. Zlotnik. 2001. Involvement of chemokine receptors in breast cancer metastasis. Nature. 410, 50-56.
3. Ohtaki, T., Y. Shintani, S. Honda, H. Matsumoto, and M. Fujino. 2001. Metastasis suppressor gene KiSS-1 encodes peptide ligand of a G-protein-coupled receptor. Nature. 411, 613-617.
4. Lee, J. H. and D. R. Welch. 1997. Suppression of metastasis in human breast carcinoma MDA-MB-435 cells after transfection with the metastasis suppressor gene, KiSS-1. Cancer Research. 57, 2384-2387.
5. Kamath, L., A. Meydani, F. Foss, and A. Kuliopulos. 2001. Signaling from protease-activated receptor-1 inhibits migration and growth of breast cancer cells. Cancer Res. 6, 5933-5940.
6. Van Golen, K. L., L. W. Bao, Q. Pan, F. R. Miller, and Z. F. Wu. 2002. Mitogen activated protein kinase pathway is involved in RhoC GTPase induced motility, growth and angiogenesis in inflammatory breast cancer. Clin. Exp. Metastasis. 19, 301-311.
7. Papetti M., and I. M. Herman. 2002. Mechanisms of normal and tumor-derived angiogenesis. Am. J. Physiol. Cell Physiol. 282, C947-970.
8. Paley, P. J. 2002. Angiogenesis in ovarian cancer: molecular pathology and therapeutic strategies. Curr. Oncol. Rep. 4, 165-174.
9. Chesney, J., C. Metz, M. Bacher, T. Peng, A. Meinhardt, and R. Bucala: 1999. An essential role for macrophage migration inhibitory factor (MIF) in angiogenesis and the growth of a murine lymphoma. Mol Med. 5, 181-191
10. Pepper, M. S., N. Ferrara, L. Orci, and R. Montesano. 1995. Leukemia inhibitory factor (LIF) inhibits angiogenesis in vitro. J Cell Sci. 108, 73-83.
11. Rosen, L. S. 2002. Clinical experience with angiogenesis signaling inhibitors: focus on vascular endothelial growth factor (VEGF) blockers. Cancer Control. 9(Suppl), 36-44.
12. Cross, M. J., and L. Claesson-Welsh. 2001. FGF and VEGF function in angiogenesis: signaling pathways, biological responses and therapeutic inhibition. Trends Pharmacol. Sci. 22.201-207.
13. Bandyopadhyay, A., Y. Zhu, S. N. Malik, J. Kreisberg, L. Z. Sun. et al. 2002. Extracellular domain of TGFbeta type III receptor inhibits angiogenesis and tumor growth in human cancer cells. Oncogene. 21, 3541-3551.
14. Mazurek, A., P. Pierzynski, W. Niklinska, L. Chyczewski, and T. Laudanski. 2002. Angiogenesis and Bcl-2 protein expression in patients with endometrial carcinoma. Neoplasma. 49, 149-154.
15. Costa, C., R. Soares, J. S. Reis-Filho, D. Leitao, and F. C. Schmitt. 2002. Cyclo-oxygenase 2 expression is associated with angiogenesis and lymph node metastasis in human breast cancer. J. Clin. Pathol. 55, 429-434.
16. Bremnes, R. M., R. Veve, F. R. Hirsch, F. R. Hirsch, and W. A. Franklin. 2002. The E-cadherin cell-cell adhesion complex and lung cancer growth, metastasis, and prognosis. Lung Cancer. 36, 115-124.
17. Yana, I., and M. Seiki. 2002. MT-MMPs play pivotal roles in cancer dissemination. Clin. Exp. Metastasis. 19, 209-215.
18. Moon, R. T., B. Bowerman, M. Boutros, and N. Perrimon. 2002. The promise and perils of Wnt signaling through beta-catenin. Science. 296, 1644-1646.
19. Falk, Goodwin, and Leonard. "A 48 Well Micro Chemotaxis Assembly for Rapid and Accurate Measurement of Leukocyte Migration." 1980, Journal of Immunological Methods, 33, 239-247.
20. Richards and McCullough. 1984. "A Modified Microchamber Method for Chemotaxis and Chemokinesis." Immunological Communications, 13, 49-62.
21. Neuroprobe Inc. www.Neuroprobe.com/protocol/pt_96a.html
22. Ilsley, S. R. 1996. MATRIGEL® Basement Membrane Cell Growth Chamber. Becton Dickinson Technical Bulletin #422.
www.bdbiosciences.com/discovery_labware/technical_resources/techbulletins.html
23. BD BioCoat™ FluoroBlok™ Tumor Cell Growth System www.bdbiosciences.com/discovery_labware/Products/drug_discovery/insert_systems/fluoroblok_growth/
24. TECAN. www.tecan.com/migration_introl.pdf
25. Berens, M. E., M. D. Rief, M. A. Loo, and A. Giese. 1994. The role of extracellular matrix in human astrocytoma migration and proliferation studied in a microliter scale assay. Clinical and Experimental Metastasis. 12, 405-415.
26. Creative Scientific Methods. www.cre8ive-sci.com/process.html.
27. Miyata K., M. Sawa, T. Tanishima. 1990. New woundhealing model using cultured corneal endothelial cells. 1. Quantitative study of healing process. Jpn J Ophthalmol. 34, 257-266.
28. Graves, R., M. P. Rosser, M. Adam, R. M. Snicler and L. Howells. A novel assay for cell growth using Cytostra-T scintillating microplates. Scientific poster. www1.amershambiosciences.com
29. Neher, E. 2001. Molecular biology meets microelectronics. Nature Biotechnology. 19, 114.

30. Stenger, D. A., G. W. Gross, E. W. Keefer, K. M. Shaffer, and J. J. Pancrazio. 2001. Detection of physiologically active compounds using cell based biosensors. Trends in Biotechnology 19(8):304-309.
31. Becker F F, Wang X-B, Huang Y, Pethig R, Vykoukal J and Gascoyne P R C. 1995. Separation of human breast cancer cells from blood by differential dielectric affinity. Proc. Nat. Academ. Sci. (USA). 29, 860-864,.
32. Wang, X., F. F. Becker, and P, R, C, Gascoyne. 1997. Dielectrophoretic manipulation of cells using spiral electrodes. Biophys. J. 72, 1887-1899.
33. Wang, X-B, J. Vykoukal, F. F. Becker, and P. R. C. Gascoyne. 1998. Separation of polystyrene beads using delectrophoretic/gravitational field-flow-fractionation. Biophys. J. 74, 2689-2701.
34. Yang, J., Y. Huang, X-B. Wang, F. F. Becker, and P. R. C. Gascoyne. 1999. Cell separation on microfabricated electrodes using dielectrophoretic/gravitational field-flow-fractionation. Anal. Chem. 71, 911-918.
35. Wang, X-B, J. Yang, Y. Huang, J. Vykoukal, F. F. Becker, P. R. C. Gascoyne. 2000. Cell separation by dielectrophoretic field-flow-fractionation. Anal. Chem. 72, 832-839.
36. Wang, X-B, and J. Cheng. 2001. Electronic manipulation of cells on microchip-based devices. In Biochip Technology (eds.) Harwood Academic Publishers, PA, U.S.A, pp 135-159.
37. Huang, Y., S. Joo, M. Duhon, M. Heller, B. Wallace, and X. Xu. 2002. Dielectrophoretic Cell Separation and Gene Expression Profiling on Microelectronic Chip Arrays. 74, 3362-3371.
38. Connolly, P., P. Clark, A. S. G. Curtis, J. A. T. Dow and C. D. W. Wilinson. 1990. An extracellular microelectrode array for monitoring electrogenic cells in culture. Biosensors & Bioelectronics. 5, 223-234.
39. Giaever, Ivar and C. R. Keese. 1991. Micromotion of Mammalian cells measured electrically. Proc. Natl. Acad. Sci. USA. 88:7896-7900.
40. Kowolenko, M., C. R. Keese, D. A. Lawrence and I.Giaever. 1990. Measurement of macrophage adherence and spreading with weak electric fields. Journal of Immunological Methods, 127(1990)71-77.
41. Lo, Chun Min, C. R. Keese and I. Giaever. 1993. Monitoring motion of confluent cell in tissue culture. Experimental cell research 204, 102-109.
42. Lo, Chun Min, C. R. Keese and I. Giaever. 1994. pH change in pulsed CO2 incubators causes periodic changes in cell morphology. Experimental cell research 213, 391-397.
43. Lo, Chun-Min, C. R. Keese, and I. Giaever. 1995. Impedance analysis of MDCK cells measured by electric cell-substrate impedance sensing. Biophysical Journal 69:2800-2807.
44. Mitra, Paramita, C. R. Keese and I. Giaever. 1991. Electric Measurements can be used to monitor the attachment and spreading of cells in tissure culture. Biotechniques. 11(4): 504-510.
45. Simpson, M. L., G. S. Sayler, J. T. Fleming and B. Applegate. 2001. Whole-cell biocomputering. Trends in Biotechnology. 19, 317-323.
46. Warburg, E. Ann. Phys. 1901, 6, 125-135.
47. Luong, J. H. T., M. Habibi-Rezaei, J. Meghrous, C. Xiao, and A. Kamen. 2001. Monitoring motility, spreading and mortality of adherent insect cells using an impedance sensor. Anal. Chem. 73, 1844-1848.
48. Berg, K., M. B. Hansen, S. E. Nielsen. 1990. A new sensitive bioassay for precise quantification of interferon activity as measured via the mitochondrial dehydrogenase function in cells (MTT-method). 98, 156-162.
49. Kleinman, H. K., M. L. McGarvey, J. R. Hassell, V. L. Star, G. R. Martin et al. 1986. Basement membrane complexes with biological activity. Biochemistry 25:312-8.
50. Burns, A. R., D. C. Walker, E. S. Brown, L. T. Thurmon, and R. A. Bowden 1997. Neutrophil Transendothelial Migration is independent of Tight hjunctions and Occurs preferentially at Tricellular Corners. The Journal of Immunology. 2893-2903.
51. Xiao, C., B. Lachance, G. Sunahara, and J. H. T. Luong. 2002. An in-depth analysis of electric cell-substrate impedance sensing to study the attachment and spreading of mammalian cells. Anal. Chem. 74, 1333-1339.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

We claim:

1. A device for monitoring the migration or invasion of a biological particle such as a cell, which device comprises:
   a) an upper chamber adapted to receive and retain a cell sample;
   b) a lower chamber comprising at least two electrodes; and,
   c) a biocompatible porous membrane having a porosity sufficient to allow cells to migrate therethrough from said upper chamber to said lower chamber, wherein said membrane is disposed in the device so as to separate the upper and lower chambers from one another, wherein said at least two electrodes are disposed on said membrane and are partially exposed through pores of said porous membrane;
   wherein migration of cells through the porous membrane permits attachment of cells that have migrated to said lower chamber on one or more of at least two electrodes of said lower chamber, wherein said at least two electrodes have substantially the same surface area, and further wherein said attachment at any one or more of said at least two electrodes provides a detectable change in impedance between or among the electrodes.

2. The device according to claim 1, further comprising an impedance analyzer in electrical communication with the at least two electrodes.

3. The device according to claim 1, wherein the biocompatible porous membrane comprises one or more polymers and further wherein the thickness of said membrane has a thickness from 5 microns to 50 microns.

4. The device according to claim 1, wherein the biocompatible porous membrane further comprises a coating for promoting the attachment of one or more cells thereto.

5. The device according to claim 1, further comprising
   a) electrically conductive traces extending from, and in electrical communication with, the at least two electrodes; and,
   b) connection means for establishing electrical communication between the electrically conductive traces and an impedance analyzer.

6. A method for monitoring the migration or invasion of a cell, the method comprising:
   a) providing a device comprising:
      i) an upper chamber adapted to receive and retain a cell sample;
      ii) a lower chamber comprising at least two electrodes;

iii) a biocompatible porous membrane having a porosity sufficient to allow cells to migrate therethrough, wherein said membrane is disposed in the device so as to separate the upper and lower chambers from one another, wherein said at least two electrodes are disposed on said membrane;

wherein migration of cells through the porous membrane permits contact between the migrating cells and one or more of at least two electrodes of said lower chamber, wherein said at least two electrodes have substantially the same surface area, and further wherein said contact at any one or more of said at least two electrodes provides a detectable change in impedance between or among the electrodes;

b) introducing the cells into the upper chamber of the device; and, c) determining whether a change in impedance between or among the electrodes occurs, where a change in impedance between or among the electrodes is indicative of the invasion of, or migration of cells into or through, the biocompatible porous membrane.

7. The method according to claim 6, further comprising the step of introducing a known or suspected modulator of cell migration to the lower chamber of the device.

8. The method according to claim 6, further comprising the step of introducing a known or suspected modulator of cell migration to the upper chamber of the device.

9. The method according to claim 6, wherein the cells are mammalian cells.

10. The method according to claim 9, wherein the mammalian cells are cells known to be or suspected of being malignant.

11. The method according to claim 9, wherein the mammalian cells are neuronal cells.

12. A device for measuring electrical impedance, resistance, or capacitance of a cell/substrate interface, comprising two or more electrodes having substantially the same surface area fabricated on one side of a flexible biocompatible membrane that comprises at least one pore, wherein said two or more electrodes are partially exposed through pores of said porous membrane, wherein said device has a surface suitable for cell attachment or growth, further wherein cell attachment or growth results in cellular contact with at least one of said two or more electrodes further resulting in a detectable change in electrical impedance, resistance or capacitance.

13. The device according to claim 12, wherein said biocompatible membrane comprises one or more plastics or one or more polymers and further wherein the thickness of said membrane is from 5 microns to 50 microns.

14. The device according to claim 13, wherein said biocompatible membrane comprises a coating that allows the attachment of one or more cells.

15. The device according to claim 14, wherein said coating comprises an extracellular matrix component.

16. The device according to claim 12 situated in a fluid container, wherein the device separates an upper chamber from a lower chamber of the fluid container.

17. The device according to claim 16, wherein said at least two electrodes are fabricated on the lower side of said membrane, wherein said at least one pore has a diameter of between 1 micron and 30 microns.

18. The device according to claim 17, wherein said membrane comprises at least one biomolecular coating, at least one extracellular matrix component, a layer of epithelial or endothelial cells, or a combination thereof, on the upper side of said membrane.

19. The device according to claim 17, wherein said device is used to assay the migration or invasiveness of one or more cells and wherein said lower chamber comprises at least one compound known to modulate the migration or invasiveness of cells, or at least one compound suspected of modulating the migration or invasiveness of cells.

20. The device according to claim 17, wherein said device is used to assay the migration or invasiveness of one or more cells and said upper chamber comprises at least one compound known to modulate the migration or invasiveness of cells, or at least one compound suspected of modulating the migration or invasiveness of cells.

21. The device according to claim 12, wherein said two or more electrodes comprise at least four electrodes and the at least four electrodes are arranged in an electrode structure array of two or more interdigitated electrode structure units (IDES) or concentric electrode structure units (CCES), each of which comprises at least two electrodes.

22. A device comprising a device for measuring electrical impedance, resistance, or capacitance of a cell/substrate interface, comprising at least four electrodes having substantially the same surface area fabricated on one side of a flexible biocompatible membrane that comprises at least one pore, wherein said at least four electrodes are arranged in an electrode structure array of two or more interdigitated electrode structure units (IDES) or concentric electrode structure units (CCES), each of which comprises at least two electrodes, further wherein said device has a surface suitable for cell attachment or growth, further wherein cell attachment or growth results in cellular contact with at least one of said at least two electrodes further resulting in a detectable change in electrical impedance, resistance or capacitance, further wherein said biocompatible membrane is reversibly or irreversibly attached to a structure that provides a plurality of isolated fluid containers such that at least one of the fluid containers comprises a single IDES or CCES structure unit, wherein for each of said plurality of isolated fluid containers that comprises a single IDES or CCES, the exposed surface area of said one side of said biocompatible membrane on which electrodes are fabricated comprises an approximately uniform distribution of electrodes or electrode elements.

23. The device according to claim 22, wherein the at least two electrodes that have substantially the same surface area are in an interdigitated configuration.

24. The device according to claim 22, wherein the at least two electrodes have a geometry selected from the group consisting of circle-on-line, diamond-on-line, castellated, and sinusoidal geometries.

25. The device according to claim 22, wherein the width of the electrodes is from 20 microns to 500 microns; further wherein the gap between electrode elements is between 3 microns and 80 microns in width; further wherein the ratio of the gap width to the electrode element width ranges from about 1:20 to about 3:1; further wherein the gap between electrode elements is between about 0.2 time and about 3 times the width of cells used in the measuring electrical impedance, resistance or capacitance of a cell/substrate interface.

26. The device of claim 22, further comprising an impedance analyzer connected to the electrodes.

27. The device according to claim 22, wherein said biocompatible membrane comprises one or more plastics or one or more polymers and further wherein the thickness of said membrane is from 5 microns to 50 microns.

28. The device according to claim 22, wherein said biocompatible membrane comprises a coating that allows the attachment of one or more cells.

29. The device according to claim 28, wherein said coating comprises an extracellular matrix component.

30. The device according to claim 22, wherein for each of said plurality of isolated fluid containers that comprises a single IDES or CCES situated in a fluid container, the biocompatible membrane separates an upper chamber from a lower chamber of the fluid container.

31. The device according to claim 30, wherein said at least two electrodes are fabricated on the lower side of said membrane, wherein said at least one pore has a diameter of between 1 micron and 30 microns.

32. The device according to claim 31, wherein said membrane comprises at least one biomolecular coating, at least one extracellular matrix component, a layer of epithelial or endothelial cells, or a combination thereof, on the upper side of said membrane.

33. The device according to claim 31, wherein said device is used to assay the migration or invasiveness of one or more cells and wherein said lower chamber comprises at least one compound known to modulate the migration or invasiveness of cells, or at least one compound suspected of modulating the migration or invasiveness of cells.

34. The device according to claim 31, wherein said device is used to assay the migration or invasiveness of one or more cells and said upper chamber comprises at least one compound known to modulate the migration or invasiveness of cells, or at least one compound suspected of modulating the migration or invasiveness of cells.

35. An apparatus for measuring electrical impedance, resistance, or capacitance of a cell/substrate interface, comprising a plate that comprises one or more wells, at least one of which comprises a device comprising two or more electrodes having substantially the same surface area fabricated on one side of a flexible biocompatible membrane that comprises at least one pore, wherein said device has a surface suitable for cell attachment or growth, further wherein cell attachment or growth results in cellular contact with at least one of said two or more electrodes further resulting in a detectable change in electrical impedance, resistance or capacitance, further wherein each device separates each well into upper and lower chambers.

36. The apparatus according to claim 35, wherein the two or more electrodes are on the lower side of the membrane.

37. A method for monitoring cell migration or invasion, comprising:
a) providing an apparatus of claim 36;
b) placing cells in the upper chamber of said apparatus; and
c) monitoring a change of impedance between or among the electrodes to monitor migration or invasion of said cells.

38. The method according to claim 37, further comprising adding a known or suspected modulator of cell migration or cell invasion to the lower chamber of said apparatus.

39. The method according to claim 37, further comprising adding a known or suspected modulator of cell migration or cell invasion to the upper chamber of said apparatus.

40. The apparatus according to claim 35, wherein the two or more electrodes are on the upper side of the membrane.

41. The apparatus according to claim 40, wherein said membrane comprises a layer of cells on the upper side of the membrane, wherein said cells are epithelial cells or endothelial cells.

42. The apparatus according to claim 40, wherein said at least one pore of the biocompatible membrane has a diameter of less than 5 microns.

43. The apparatus according to claim 40, wherein said membrane comprises a layer of cells on the upper side of said membrane, wherein said cells are Caco-2 cells.

44. A method of measuring the integrity of a cell monolayer, comprising:
a) providing the apparatus of claim 40;
b) culturing cells in said upper chamber of said apparatus; and
c) monitoring the integrity of the cell monolayer in said upper chamber by monitoring the impedance.

45. The apparatus according to claim 35,
wherein said two or more electrodes comprise at least four electrodes and the at least four electrodes are arranged in an electrode structure array of two or more interdigitated electrode structure units (IDES) or concentric electrode structure units (CCES), each of which comprises at least two electrodes,
further wherein the biocompatible membrane is reversibly or irreversibly attached to a first plate that comprises two or more wells that provide lower chambers of cell migration units and is reversibly or irreversibly attached to a second plate that provides tube structures that provide upper chambers of cell migration units, such that each cell migration unit comprises a single IDES or CCES.

46. The apparatus according to claim 45, further comprising an impedance analyzer, interface electronics comprising electronic switches to control and switch said impedance analyzer to different electrode structure units of said apparatus, and a software that can enable real time measurement or monitoring of impedance between the electrodes or electrode structures of said apparatus.

47. The apparatus according to claim 46, wherein said software has at least one function selected from the group consisting of:
(a) controlling electronic switching for connecting said impedance analyzer to one of multiple electrode structure units of the present apparatuses;
(b) controlling impedance analyzer for measurement of impedance between or among electrode structures at one or multiple frequencies;
(c) processing the acquired impedance data to derive appropriate biologically relevant parameters (e.g., cell number index);
(d) displaying the results on a monitor or storing results; and
(e) automatically performing above functions (a) through (d) at regular or irregular time intervals.

48. An apparatus according to claim 35, further comprising an insert tray that comprises one or more insert chamber, each of which comprising:
(a) fluid impermeable walls, and
(b) wherein said device forms the bottom of each of said one or more insert chamber;
further wherein each insert chamber fits into a well of said plate such that the wells of the plate form a lower chamber and the insert forms an upper chamber of a cell invasion/migration unit.

* * * * *